United States Patent
Mao et al.

(10) Patent No.: US 12,378,277 B2
(45) Date of Patent: Aug. 5, 2025

(54) SGLTS/DPP4 INHIBITOR AND APPLICATION THEREOF

(71) Applicant: DONGBAO PURPLE STAR (HANGZHOU) BIOPHARMACEUTICAL CO., LTD., Zhejiang (CN)

(72) Inventors: Qinghua Mao, Shanghai (CN); Tao Yu, Shanghai (CN); Yi Li, Shanghai (CN); Chengde Wu, Shanghai (CN); Shuhui Chen, Shanghai (CN)

(73) Assignee: DONGBAO PURPLE STAR (HANGZHOU) BIOPHARMACEUTICAL CO., LTD., Zhejiang (CN)

( * ) Notice: Subject to any disclaimer, the term of this patent is extended or adjusted under 35 U.S.C. 154(b) by 705 days.

(21) Appl. No.: 17/629,618

(22) PCT Filed: Jul. 24, 2020

(86) PCT No.: PCT/CN2020/104534
§ 371 (c)(1),
(2) Date: Jan. 24, 2022

(87) PCT Pub. No.: WO2021/018046
PCT Pub. Date: Feb. 4, 2021

(65) Prior Publication Data
US 2022/0259247 A1 Aug. 18, 2022

(30) Foreign Application Priority Data
Jul. 26, 2019 (CN) .......................... 201910683107.3
Feb. 20, 2020 (CN) .......................... 202010105252.6

(51) Int. Cl.
C07H 7/06 (2006.01)
A61P 3/10 (2006.01)

(52) U.S. Cl.
CPC .................. C07H 7/06 (2013.01); *A61P 3/10* (2018.01)

(58) Field of Classification Search
CPC ........ C07H 7/04–06; A61K 31/35–351; A61K 31/7042; A61P 3/08–10
See application file for complete search history.

(56) References Cited

U.S. PATENT DOCUMENTS

| 7,683,160 B2 * | 3/2010 | Eckhardt .............. C07D 309/10 |
| | | 536/1.11 |
| 2005/0209166 A1 | 9/2005 | Eckhardt et al. |
| 2017/0037038 A1 * | 2/2017 | Gao ........................ A61K 45/06 |

FOREIGN PATENT DOCUMENTS

| CN | 105294694 | 2/2016 | |
| WO | WO2002083066 A2 | 10/2002 | |
| WO | WO 2005/092877 | 10/2005 | |
| WO | WO 2006/064033 | 6/2006 | |
| WO | WO 2007/093610 | 8/2007 | |
| WO | WO 2008/020011 | 2/2008 | |
| WO | WO 2008/042688 | 4/2008 | |
| WO | WO 2008/055940 | 5/2008 | |
| WO | WO 2008/109591 | 9/2008 | |
| WO | WO-2011070592 A2 * | 6/2011 | .......... C07D 309/10 |
| WO | WO 2012/094293 | 7/2012 | |
| WO | WO 2014/081660 A1 | 5/2014 | |

OTHER PUBLICATIONS

Extended European Search Report issued in European Patent Application No. 20847749.7, dated Aug. 4, 2023.
First Examination Report issued in Indian Patent Application No. 202217008034, dated May 5, 2022.
English translation of International Search Report issued in International Patent Application No. PCT/CN2020/104534, dated Oct. 28, 2020.

* cited by examiner

*Primary Examiner* — Leigh C Maier
(74) *Attorney, Agent, or Firm* — Parker Highlander PLLC

(57) ABSTRACT

A class of compounds as a SGLT1/SGLT2/DPP4 triple inhibitor, and an application in preparation of a drug serving as the SGLT1/SGLT2/DPP4 triple inhibitor. Compounds represented by formula (I), and isomers and pharmaceutically-acceptable salts thereof are specifically involved.

(I)

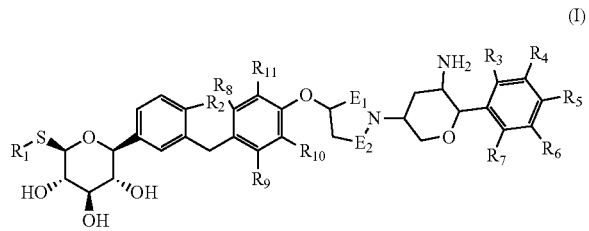

17 Claims, No Drawings

SGLTS/DPP4 INHIBITOR AND APPLICATION THEREOF

This application is a national phase application under 35 U.S.C. § 371 of International Application No. PCT/CN2020/104534, titled "SGLTS/DPP4 INHIBITOR AND APPLICATION THEREOF," filed on Jul. 24, 2020, which claims the priority to Chinese Patent Application No. 201910683107.3, titled "SGLTS/DPP4 INHIBITOR AND APPLICATION THEREOF," filed on Jul. 26, 2019, and Chinese Patent Application No. 202010105252.6, titled "SGLTS/DPP4 INHIBITOR AND APPLICATION THEREOF," filed on Feb. 20, 2020 with the China National Intellectual Property Administration, which are incorporated herein by reference in entirety.

FIELD

The present disclosure relates to a class of compounds that are SGLT1/SGLT2/DPP4 triple inhibitors, and use in the preparation of a medicament as SGLT1/SGLT2/DPP4 triple inhibitors, specifically relates to a compound represented by formula (I), an isomer or a pharmaceutically acceptable salt thereof.

BACKGROUND

Diabetes is a metabolic disease characterized by hyperglycemia. Hyperglycemia is caused by defective insulin secretion or impaired biological effects, or both. In diabetes, long-term abnormal blood glucose levels can lead to serious complications, including cardiovascular disease, chronic renal failure, retinal damage, nerve damage, microvascular damage, obesity and the like. In the early stage of the treatment of diabetes, diet control and exercise therapy are the first choice for the control of blood sugar. When these methods are difficult to control blood sugar, insulin or oral hypoglycemic drugs are needed for treatment. At present, there are a variety of hypoglycemic drugs used in clinical treatment, mainly including biguanides, sulfonylureas, insulin tolerance improvers, glinides, α-glucosidase inhibitors and dipeptidyl peptidase-IV inhibitors and the like. These drugs have good therapeutic effects, but there are still safety problems in long-term treatment. For example, biguanides are prone to cause lactic acidosis; sulfonylureas can cause symptoms of hypoglycemia; insulin tolerance improvers can cause edema, heart failure and gain of weight; α-glucosidase inhibitors can cause abdominal pain, bloating abdominal distension, diarrhea and other symptoms. Therefore, there is an urgent need to develop a safer and more effective new hypoglycemic drug to meet the needs of diabetes treatment.

Sodium-glucose cotransporters (SGLTs) are a family of glucose transporters found in the small intestinal mucosa and renal proximal tubules. The family members mainly include SGLT1 protein and SGLT2 protein. Their function is to mediate the transmembrane transport of glucose in the intestines and kidneys, which plays a key role in maintaining the stability of human blood sugar. Specifically, SGLT1 is mainly distributed in intestinal mucosal cells of the small intestine, and is also expressed in myocardium and kidney in a small amount. It mainly regulates the intestinal absorption of glucose. SGLT2 is expressed at a high level in the kidney and is mainly responsible for the regulation of the process of glucose reuptake in the kidney, that is, the glucose in the urine can be actively attached to the renal tubular epithelial cells when filtered by the glomerulus and be transported into the cell by the SGLT2 protein to be reused. In this process, SGLT2 is responsible for 90% of the reabsorption process, and the remaining 10% is completed by SGLT1. This process does not involve glucose metabolism, thereby avoiding or reducing the occurrence of adverse reactions of hypoglycemia and reducing the risk of causing cardiovascular diseases. Therefore, SGLTs have become one of the ideal potential targets for the treatment of diabetes.

In view of this, some SGLTs inhibitors, especially SGLT2 inhibitors of high selectivity have been developed one after another. By inhibiting the activity of SGLT2, they specifically inhibit the reabsorption of glucose by the kidneys, thereby increasing the excretion of glucose in the urine, and normalizing the plasma glucose of diabetic patients. Since 2012, six drugs such as Dapagliflozin, Canagliflozin, Luseogliflozin, Ipragliflozin, Tofogliflozin and Empagliflozin have been approved for marketing, and become effective drugs for the treatment of diabetes.

In addition to selective SGLT2 inhibitors, studies in recent years have found that while inhibiting SGLT2, partial inhibition of SGLT1 can not only inhibit renal glucose reuptake, but also control the intestinal glucose absorption without diarrhea or other gastrointestinal tracts. At the same time, by inhibiting intestinal SGLT1 to reduce the glucose entering the blood through the gastrointestinal tract, the levels of GLP-1 and PYY after a meal can be increased, thereby exerting a better hypoglycemic effect than selective SGLT2 inhibitors, and reducing risks of urinary tract infection and kidney function damage. Therefore, the development of SGLT1/SGLT2 dual inhibitors has become a new target and direction for diabetes treatment in recent years. At present, the SGLT1/SGLT2 dual inhibitor Sotagliflozin jointly developed by Lexicon and Sanofi has been marketed in the European Union (WO2008042688/WO2012094293).

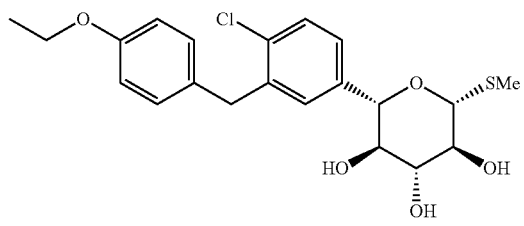

Soagliflozin

Dipeptidyl peptidase-IV (Dipeptidyl peptidase 4) is a serine protease on the cell surface, which can inactivate a variety of glucagon-like peptide-1 (GLP-1) and glucose-dependent insulinotropic polypeptide (GIP). DPP-4 inhibitors can inactivate DPP-4, and thus GLP-1 is not decomposed, and can control blood glucose by increasing the level of GLP-1. So far, a variety of DPP-4 inhibitors have been marketed worldwide: sitagliptin, vildagliptin, saxagliptin, alogliptin, linagliptin, gemigliptin and tenegliptin. The marketed DPP4 drug has weak hypoglycemic effect. Although there is no cardiovascular benefit, long-term data show that it is safe and reliable without obvious side effects.

SGLT1 and DPP4 target inhibitors have a synergistic effect, which can promote and prolong the secretion and concentration of endogenous GLP-1, stimulate the secretion of endogenous insulin and increase the application of overall sugar energy in the body. In addition, SGLT2 target inhibition can accelerate the excretion of glucose under the condition of high blood sugar level, which runs through the overall pathway of absorption, metabolism and excretion of glucose in the body, reduces blood sugar levels in all aspects and is less likely to cause the risk of hypoglycemia.

In summary, the SGLT1/SGLT2/DPP4 triple inhibitors have a good development prospect.

SUMMARY

The present disclosure provides a compound of formula (I), an isomer or a pharmaceutically acceptable salt thereof,

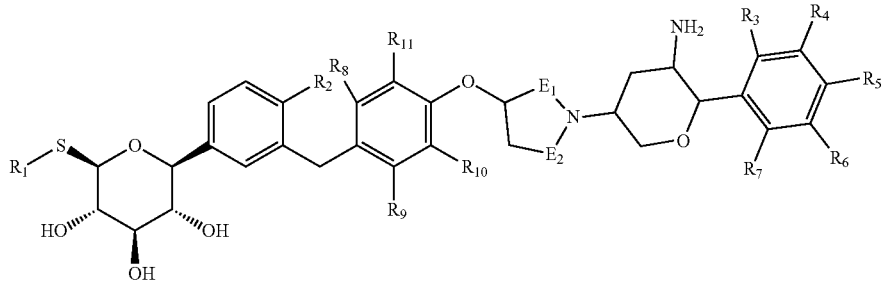

wherein,
$R_1$ is selected from $C_{1-3}$ alkyl, wherein the $C_{1-3}$ alkyl is optionally substituted by 1, 2 or 3 $R_a$;
$R_2$ is selected from Cl, Br, I, OH, $NH_2$ and $C_{1-3}$ alkyl, wherein the $C_{1-3}$ alkyl is optionally substituted by 1, 2 or 3 $R_b$;
$R_3$, $R_4$, $R_5$, $R_6$ and $R_7$ are each independently selected from H, F, Cl, Br, I, OH, $NH_2$ and $C_{1-3}$ alkyl, wherein the $C_{1-3}$ alkyl is optionally substituted by 1, 2 or 3 $R_c$;
$R_8$, $R_9$, $R_{10}$ and $R_{11}$ are each independently selected from H, F, Cl, Br, I, OH, $NH_2$ and $C_{1-3}$ alkyl, wherein the $C_{1-3}$ alkyl is optionally substituted by 1, 2 or 3 $R_d$;
$E_1$ is —$(CH_2)_m$—;
$E_2$ is —$(CH_2)_n$—;
m is 0, 1 or 2;
n is 0, 1 or 2;
$R_a$, $R_b$, $R_c$ and $R_d$ are each independently selected from F, Cl, Br, I, OH and $NH_2$.

The present disclosure also provides a compound of formula (I), an isomer or a pharmaceutically acceptable salt thereof,

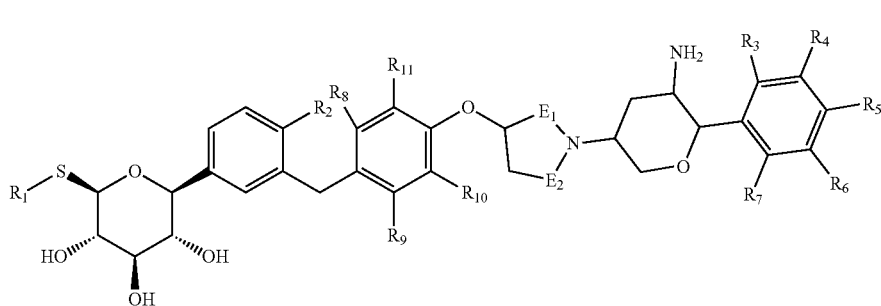

wherein,
$R_1$ is selected from $C_{1-3}$ alkyl, wherein the $C_{1-3}$ alkyl is optionally substituted by 1, 2 or 3 $R_a$;
$R_2$ is selected from Cl, Br, I, OH, $NH_2$ and $C_{1-3}$ alkyl, wherein the $C_{1-3}$ alkyl is optionally substituted by 1, 2 or 3 $R_b$;
$R_3$, $R_4$, $R_5$, $R_6$ and $R_7$ are each independently selected from H, F, Cl, Br, I, OH, $NH_2$ and $C_{1-3}$ alkyl, wherein the $C_{1-3}$ alkyl is optionally substituted by 1, 2 or 3 $R_c$;
$R_8$, $R_9$, $R_{10}$ and $R_{11}$ are each independently selected from H, F, Cl, Br, I, OH, $NH_2$ and $C_{1-3}$ alkyl, wherein the $C_{1-3}$ alkyl is optionally substituted by 1, 2 or 3 $R_d$;
$E_1$ is —$(CH_2)_m$—;
$E_2$ is —$(CH_2)_n$—;
m is 0, 1 or 2;
n is 0, 1 or 2;
$R_a$, $R_b$ and $R_c$ are each independently selected from F, Cl, Br, I, OH and $NH_2$.

In some embodiments of the present disclosure, the above-mentioned $R_1$ is selected from $CH_3$ and Et, and the $CH_3$ and Et are optionally substituted by 1, 2 or 3 $R_a$, and other variables are as defined in the present disclosure.

In some embodiments of the present disclosure, the above-mentioned $R_1$ is selected from $CH_3$, and other variables are as defined in the present disclosure.

In some embodiments of the present disclosure, the above-mentioned $R_2$ is selected from Cl, Br, I, OH, $NH_2$, $CH_3$ and Et, wherein the $CH_3$ and Et are optionally substituted by 1, 2 or 3 $R_b$, and other variables are as defined in the present disclosure.

In some embodiments of the present disclosure, the above-mentioned $R_2$ is selected from Cl, Br, I, OH, $NH_2$, $CH_3$, Et and

wherein the CH₃, Et and

are optionally substituted by 1, 2 or 3 R_b, and other variables are as defined in the present disclosure.

In some embodiments of the present disclosure, the above-mentioned R₂ is selected from Cl, Br, I, OH, NH₂, CH₃ and Et, and other variables are as defined in the present disclosure.

In some embodiments of the present disclosure, the above-mentioned R₂ is selected from Cl, Br, I, OH, NH₂, CH₃, Et and

and other variables are as defined in the present disclosure.

In some embodiments of the present disclosure, the above-mentioned R₃, R₄, R₅, R₆, and R₇ are independently selected from H, F, Cl, Br, I, OH, NH₂, CH₃ and Et, wherein the CH₃ and Et are optionally substituted by 1, 2 or 3 R_c, and other variables are as defined in the present disclosure.

In some embodiments of the present disclosure, the above-mentioned R₃, R₄, R₅, R₆ and R₇ are independently selected from H, F, Cl, Br, I, OH and NH₂, and other variables are as defined in the present disclosure.

In some embodiments of the present disclosure, the above-mentioned R₈, R₉, R₁₀ and R₁₁ are independently selected from H, F, Cl, Br, I, OH, NH₂, CH₃ and Et, wherein the CH₃ and Et are optionally substituted by 1, 2 or 3 R_d, and other variables are as defined in the present disclosure.

In some embodiments of the present disclosure, the above-mentioned R₈, R₉, R₁₀, and R₁₁ are independently selected from H, F, Cl, Br, I, OH, NH₂, CH₃, and Et, and other variables are as defined in the present disclosure.

In some embodiments of the present disclosure, the above-mentioned E₁ is —CH₂— or —CH₂—CH₂—, and other variables are as defined in the present disclosure.

In some embodiments of the present disclosure, the above E₁ is —CH₂—, and other variables are as defined in the present disclosure.

In some embodiments of the present disclosure, the above E₂ is a single bond or —CH₂—, and other variables are as defined in the present disclosure.

In some embodiments of the present disclosure, the above E₂ is —CH₂—, and other variables are as defined in the present disclosure.

There are also some embodiments of the present disclosure that come from any combination of the above-mentioned variables.

In some embodiments of the present disclosure, the above-mentioned compound, the isomer, or the pharmaceutically acceptable salt thereof, wherein the compound is selected from

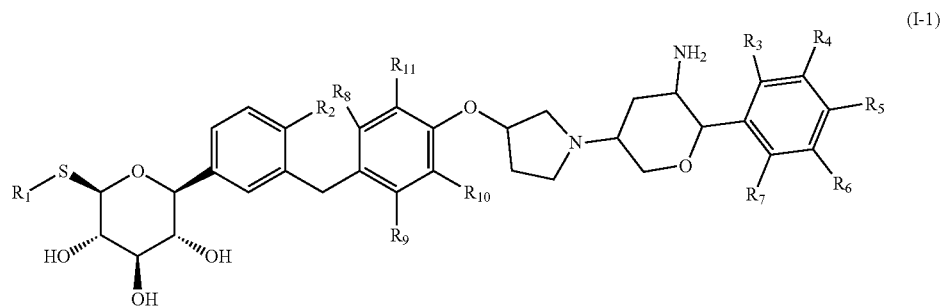

(I-1)

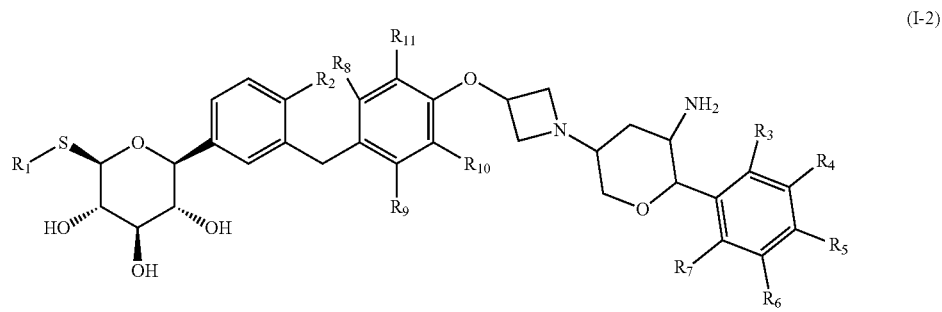

(I-2)

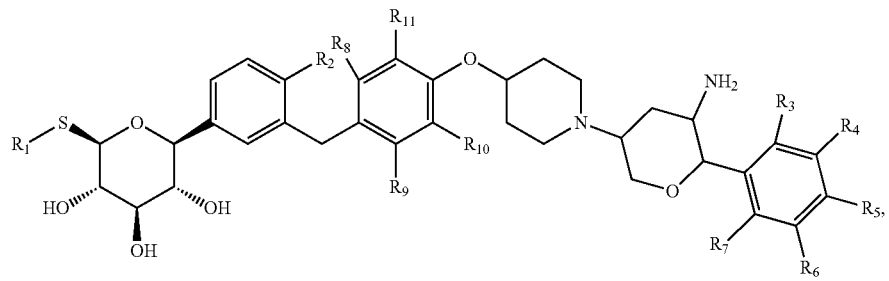
(I-3)
wherein,
$R_1$, $R_2$, $R_3$, $R_4$, $R_5$, $R_6$, $R_7$, $R_8$, $R_9$, $R_{10}$ and $R_{11}$ are as defined in the present disclosure.
In some embodiments of the present disclosure, the above-mentioned compound, the isomer, or the pharmaceutically acceptable salt thereof is selected from
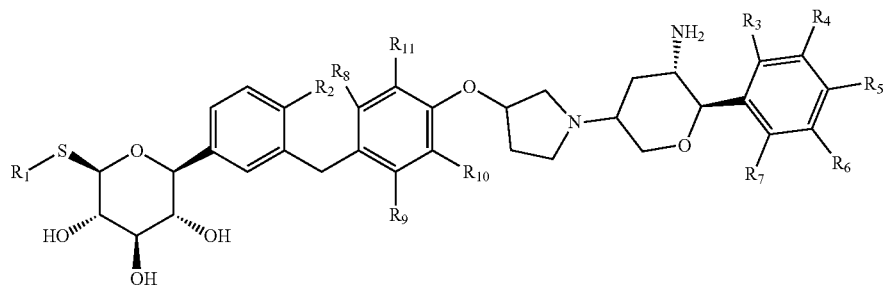
(I-1A)
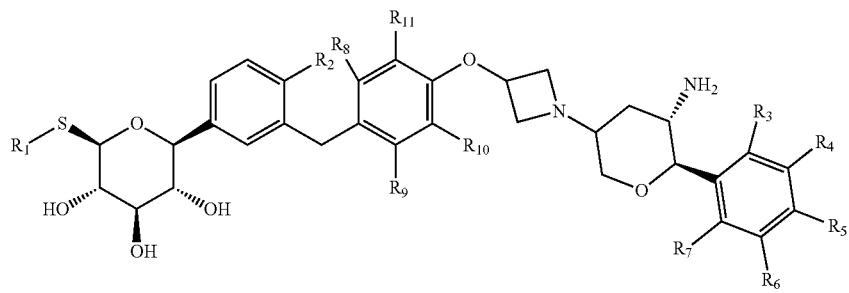
(I-2A)
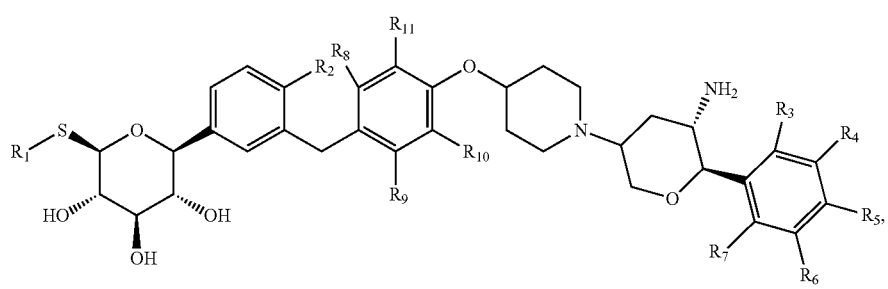
(I-3A)
wherein,
$R_1$, $R_2$, $R_3$, $R_4$, $R_5$, $R_6$, $R_7$, $R_8$, $R_9$, $R_{10}$ and $R_{11}$ are as defined in the present disclosure.

The present disclosure also provides the following compounds, the isomer, or the pharmaceutically acceptable salt thereof,
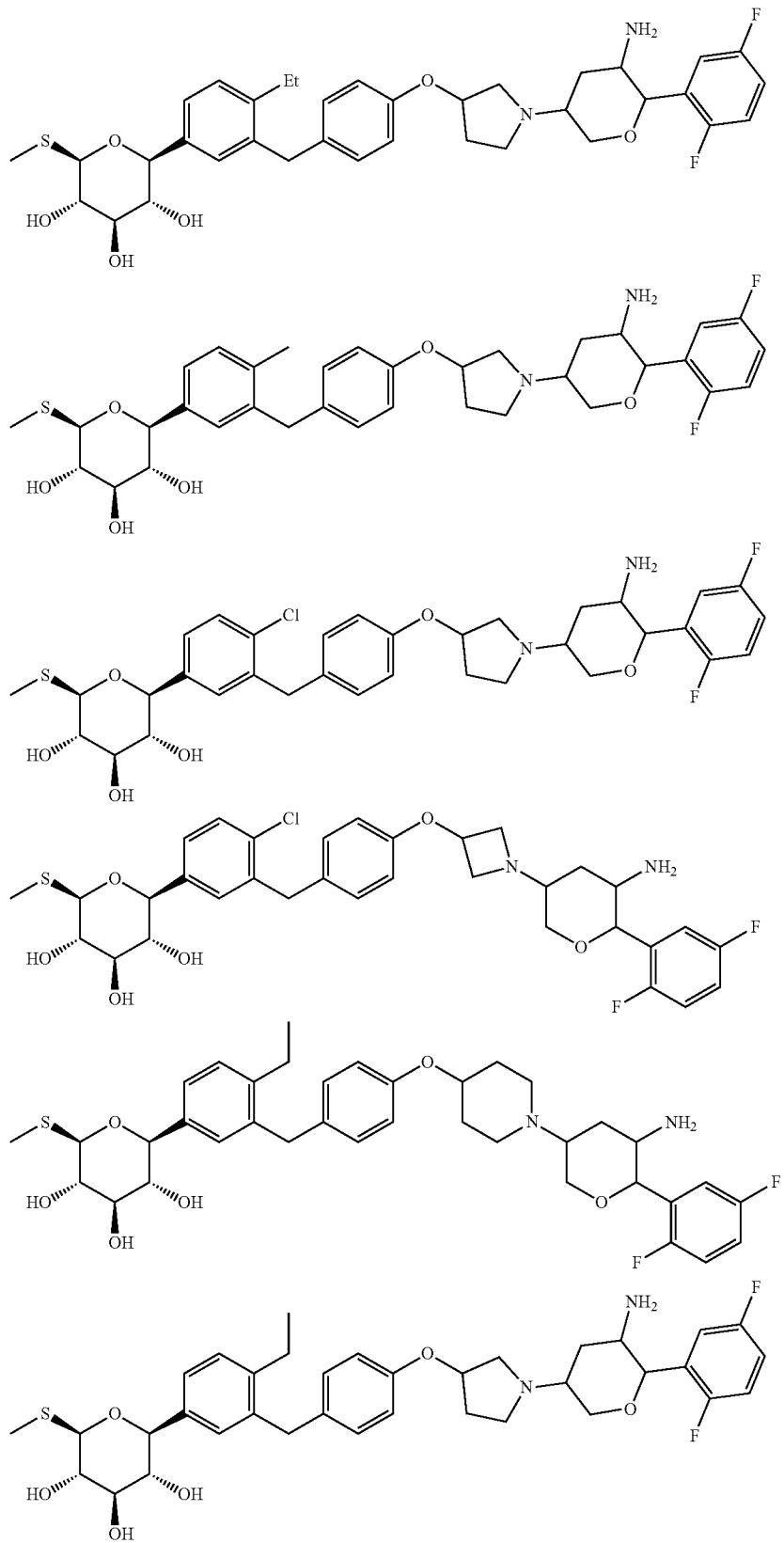

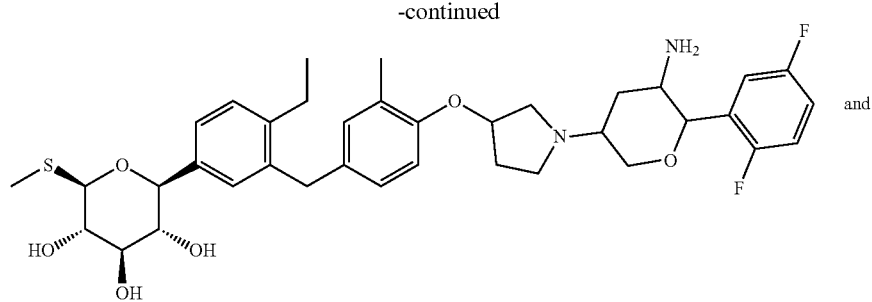
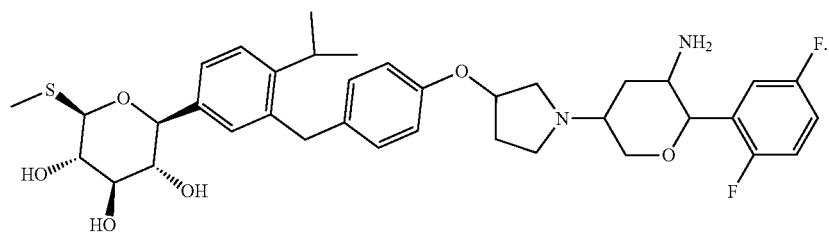
In some embodiments of the present disclosure, the above compound, the isomer, or the pharmaceutically acceptable salt thereof is selected from
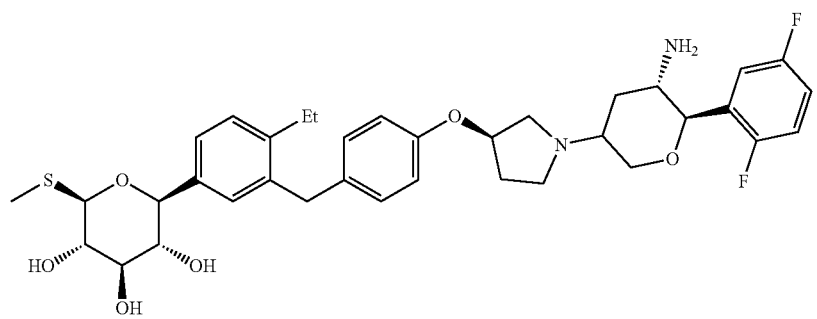
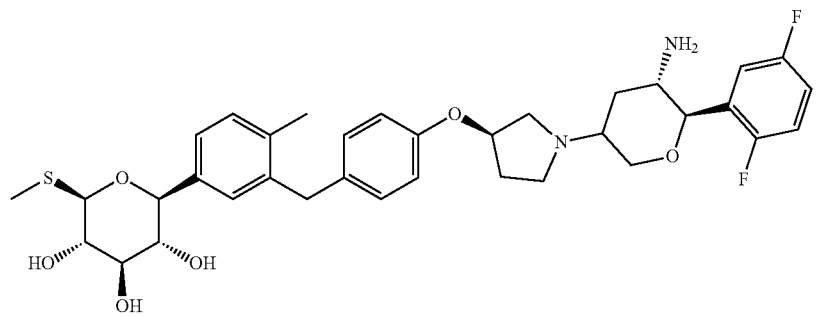
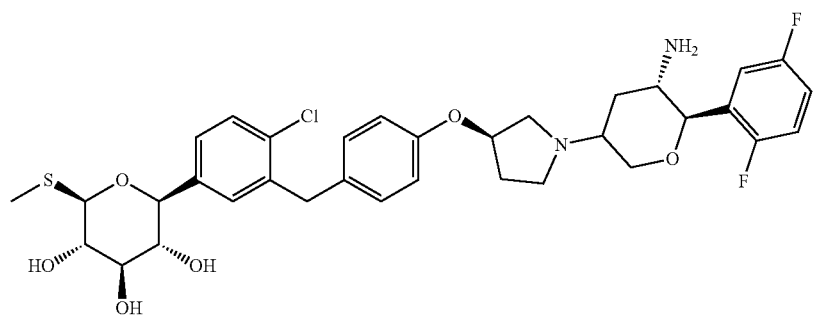

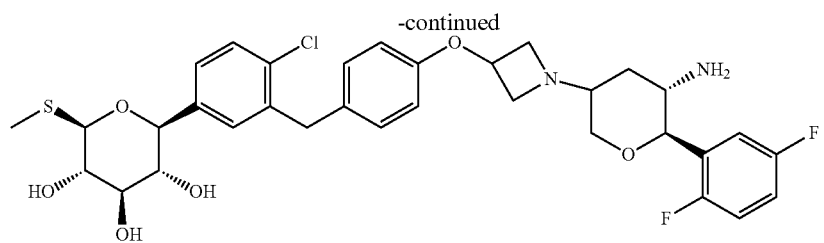
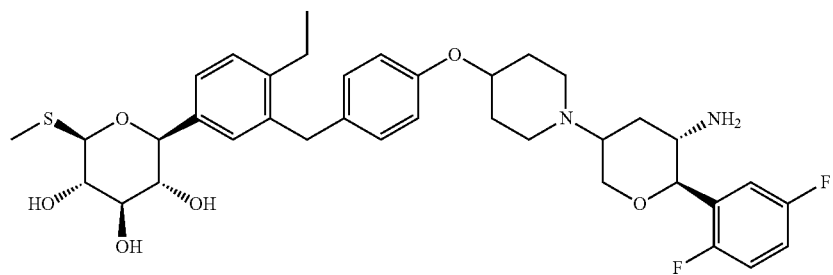
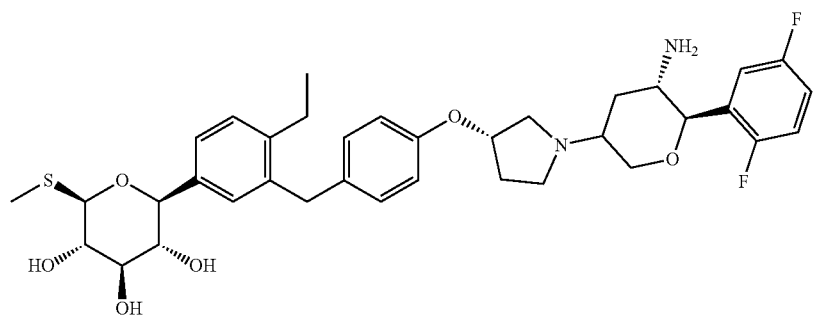
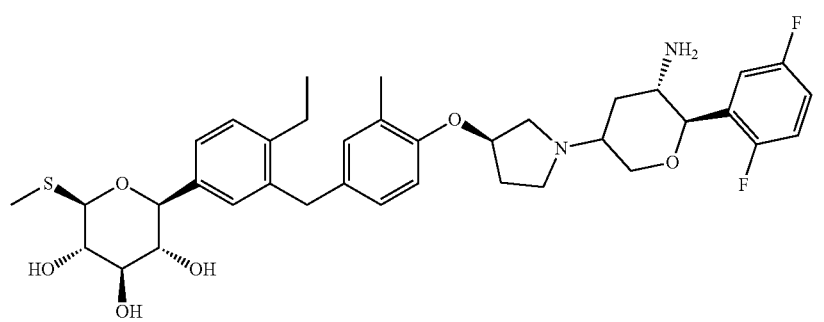
and
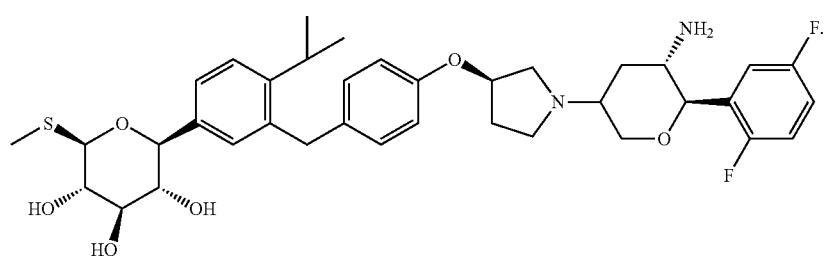

In some embodiments of the present disclosure, the above compound, the isomer, or the pharmaceutically acceptable salt thereof is selected from
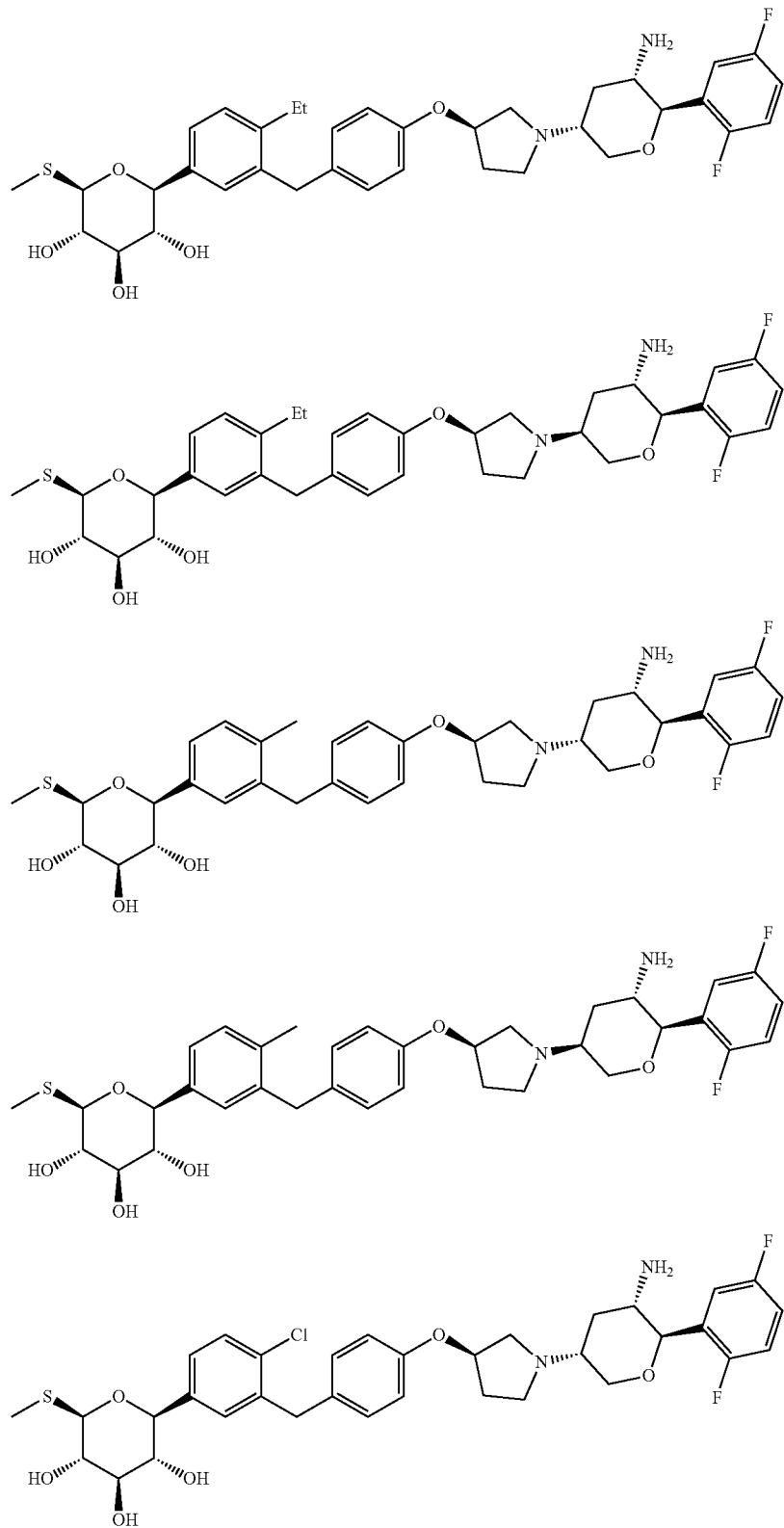

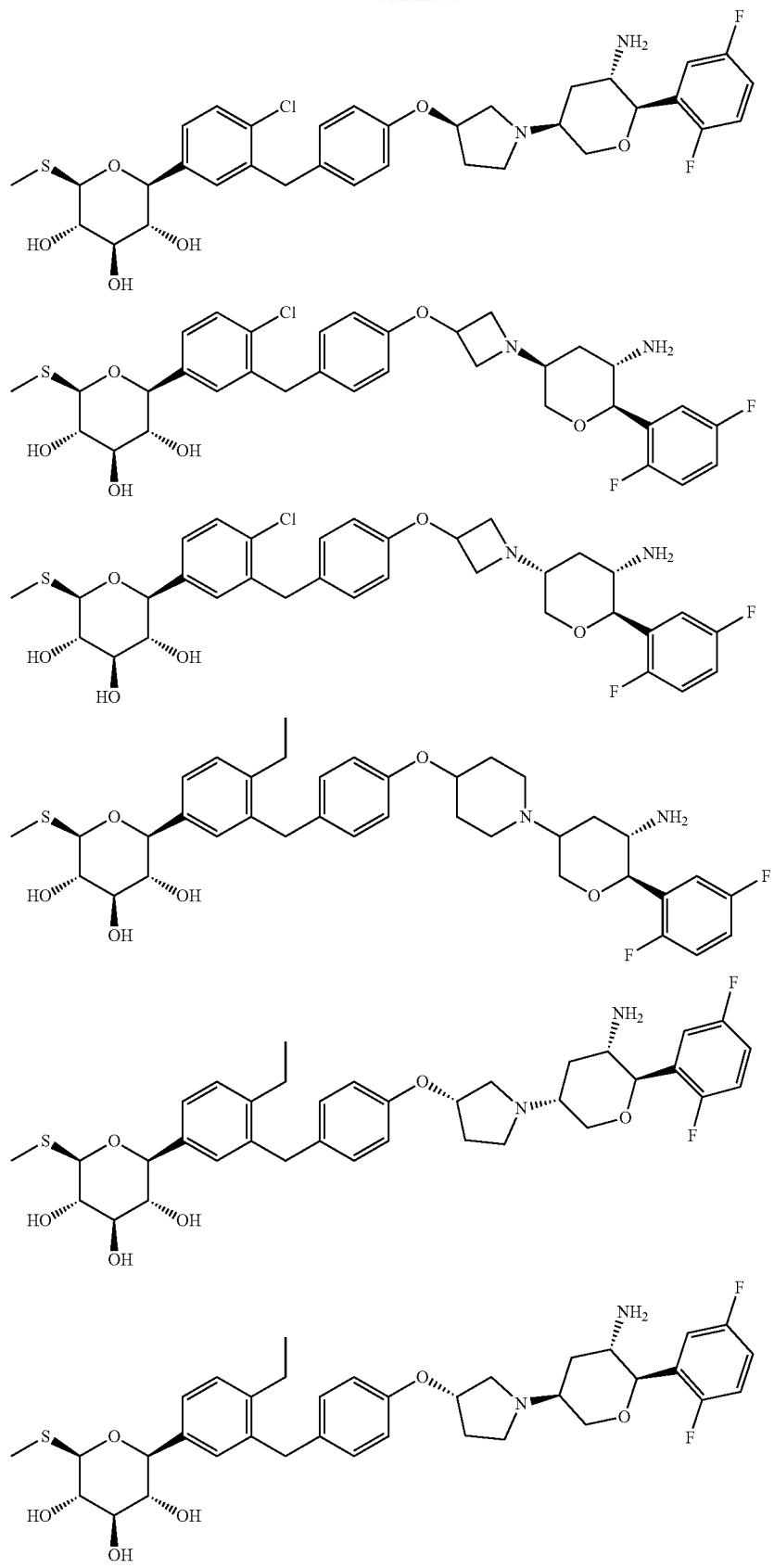

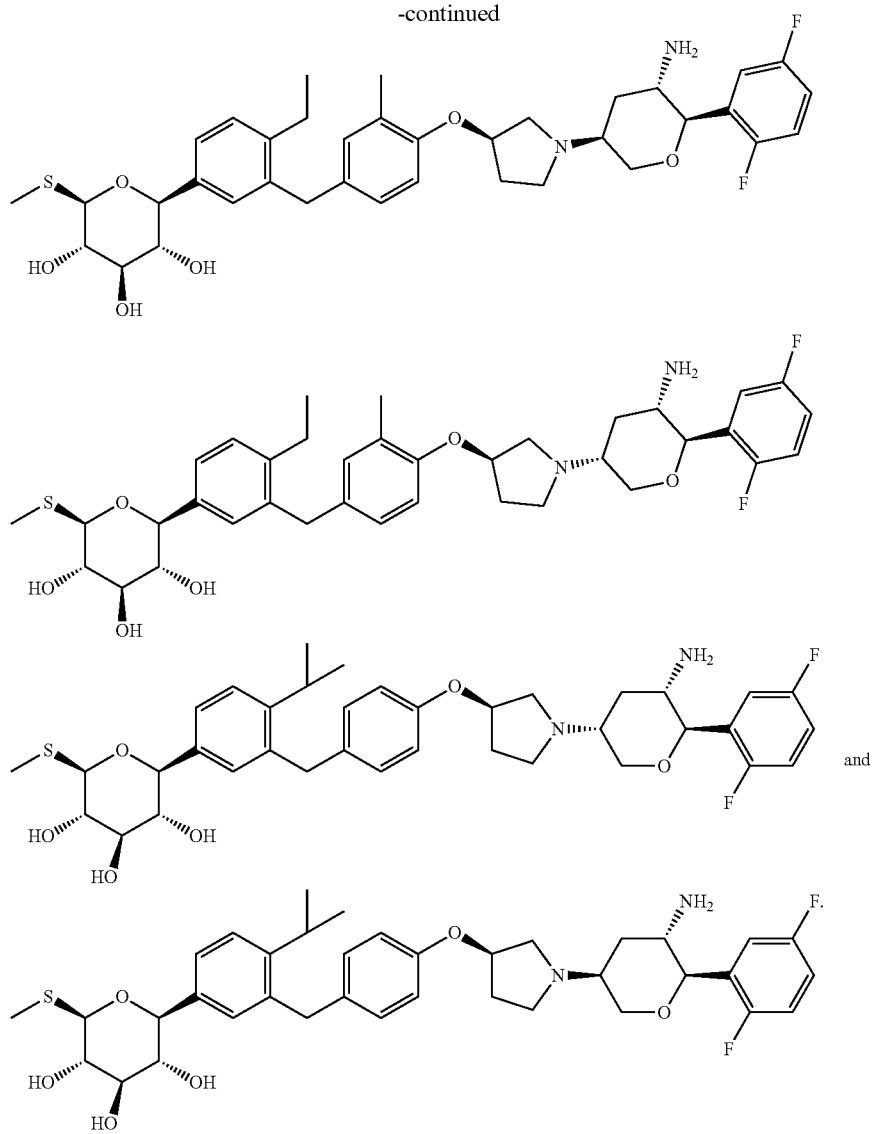

and

The present disclosure also provides use of the above compound or the pharmaceutically acceptable salt thereof in the manufacture of a medicament related to SGLT1/SGLT2/DPP4 triple inhibitors.

Technical Effect

The compound of the present disclosure exhibits excellent inhibitory activity on Human-SGLT1, Human-SGLT2 and rhDPP4 in vitro; it shows a certain oral exposure and bioavailability; compared with the solvent control group, the compound of the present disclosure can significantly reduce blood glucose AUC level within 2 hours in animals; 24-hour urine glucose excretion level of the animals was lower than that of the positive compound.

Definition and Description

Unless otherwise specified, the following terms and phrases used herein are intended to have the following meanings. A specific term or phrase should not be considered uncertain or unclear without a special definition, but should be understood in its ordinary meaning. When a trade name appears in this article, it is meant to refer to the corresponding commodity or active ingredient thereof.

The term "pharmaceutically acceptable" used here refers to those compounds, materials, compositions and/or dosage forms that are within the scope of reliable medical judgment and are suitable for use in contact with human and animal tissues, without excessive toxicity, irritation, allergic reactions or other problems or complications, which is commensurate with a reasonable benefit/risk ratio.

The term "pharmaceutically acceptable salt" refers to a salt of the compound of the present disclosure, which is prepared from a compound with specific substituents found in the present disclosure and a relatively non-toxic acid or base. When the compound of the present disclosure contains a relatively acidic functional group, a base addition salt can be obtained by contacting the compound with a sufficient amount of base in a pure solution or a suitable inert solvent. Pharmaceutically acceptable base addition salts include sodium, potassium, calcium, ammonium, organic amine, or magnesium salt, or similar salts. When the compound of the present disclosure contains a relatively basic functional group, the acid addition salt can be obtained by contacting the compound with a sufficient amount of acid in a pure solution or a suitable inert solvent. Examples of pharmaceutically acceptable acid addition salts include inorganic acid salts, the inorganic acid including for example, hydrochloric acid, hydrobromic acid, nitric acid, carbonic acid, bicarbonate radical, phosphoric acid, monohydrogen phosphate radical, dihydrogen phosphate radical, sulfuric acid, bisulfate radical, hydroiodic acid, phosphorous acid and the like; and organic acid salts, the organic acid including for example acetic acid, propionic acid, isobutyric acid, maleic acid, malonic acid, benzoic acid, succinic acid, octanedioic acid, fumaric acid, lactic acid, mandelic acid, phthalic acid, benzenesulfonic acid, p-toluenesulfonic acid, citric acid, tartaric acid and methanesulfonic acid and similar acids; and also salts of amino acids (such as arginine and so on); and salts of organic acids such as glucuronic acid. Certain compounds of the present disclosure contain basic and acidic functional groups, so that they can be converted into any base or acid addition salt.

The pharmaceutically acceptable salt of the present disclosure can be synthesized from the parent compound containing acid radical or basic group by conventional chemical methods. Generally, such salts are prepared by reacting these compounds in free acid or base form with stoichiometric amounts of appropriate bases or acids in water or organic solvents or a mixture of both.

The compounds of the present disclosure may exist in specific geometric or stereoisomeric forms. The present disclosure contemplates all such compounds, including cis and trans isomers, (−)- and (+)-enantiomers, (R)- and (S)-enantiomers, diastereomers, (D)-isomers, (L)-isomers, and their racemic mixtures and other mixtures, such as enantiomers or diastereomer enriched mixtures, all of these mixtures belong to the scope of the invention. Additional asymmetric carbon atoms may be present in substituents such as alkyl groups. All these isomers and their mixtures are included in the scope of the present disclosure.

Unless otherwise specified, the term "enantiomer" or "optical isomer" refers to stereoisomers that are mirror images of each other.

Unless otherwise specified, the term "cis-trans isomer" or "geometric isomer" is caused by the inability to rotate freely because of double bonds or single bonds of ring-forming carbon atoms.

Unless otherwise specified, the term "diastereomer" refers to a stereoisomer in which a molecule has two or more chiral centers and the molecules are in a non-mirror relationship.

Unless otherwise specified, "(+)" means right-handed, "(−)" means left-handed, and "(±)" means racemic.

Unless otherwise specified, the wedge-shaped solid line bond ( ▲ ) and the wedge-shaped dashed line bond ( ⋯ ) are used to indicate the absolute configuration of a stereogenic center, and the straight solid line bond ( ／ ) and the straight dashed line bond ( ⋯ ) are used to indicate the relative configuration of the stereogenic center. A wavy line ( ∿ ) is used to indicate a wedge-shaped solid line bond ( ▲ ) or a wedge-shaped dashed line bond ( ⋯ ), or a wavy line ( ∿ ) is used to indicate a straight solid line bond ( ／ ) and a straight dashed line bond ( ⋯ ).

Unless otherwise specified, when there is a double bond structure in the compound, such as carbon-carbon double bond, carbon-nitrogen double bond, and nitrogen-nitrogen double bond, and each atom on the double bond is connected to two different substituents (in a double bond including a nitrogen atom, a lone pair of electrons on the nitrogen atom is regarded as a substituent to which it is connected). If an atom on the double bond in the compound and its substituent are connected by a wavy line ( ∿ ), it means (Z) isomer of the compound, (E) isomer of the compound or a mixture of two isomers. For example, the following formula (A) means that the compound exists as a single isomer of formula (A-1) or formula (A-2), or in the form of a mixture of two isomers of formula (A-1) and formula (A-2). The following formula (B) means that the compound exists in the form of a single isomer of formula (B-1) or formula (B-2), or in the form of a mixture of two isomers of formula (B-1) and formula (B-2). The following formula (C) means that the compound exists as a single isomer of formula (C-1) or formula (C-2), or in the form of a mixture of two isomers of formula (C-1) and formula (C-2).

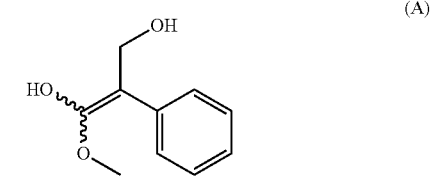

(A)

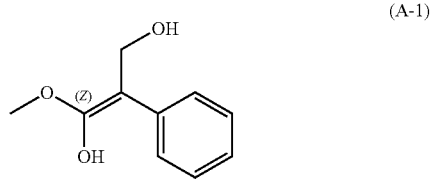

(A-1)

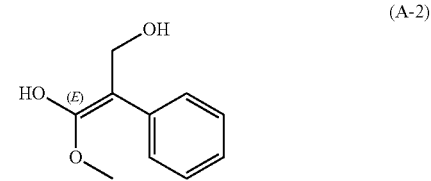

(A-2)

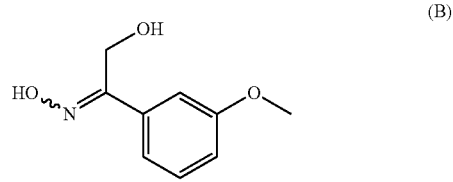

(B)

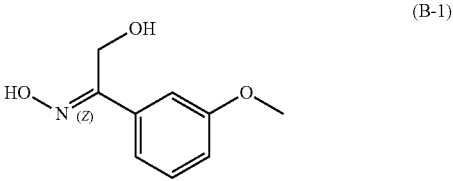

(B-1)

(B-2)

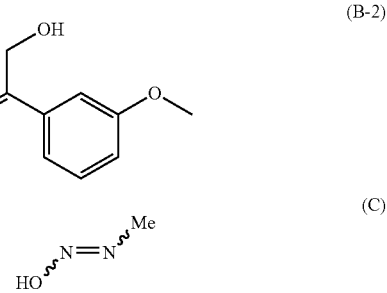

(C)

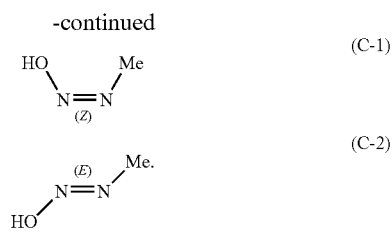

Unless otherwise specified, the term "tautomer" or "tautomeric form" means that at room temperature, the isomers of different functional groups are in dynamic equilibrium and can be transformed into each other quickly. If tautomers are possible (such as in solution), the chemical equilibrium of tautomers can be reached. For example, proton tautomer (also called prototropic tautomer) includes interconversion through proton migration, such as keto-enol isomerization and imine-enamine isomerization. Valence isomers include mutual conversion of reorganization of some bonding electrons. A specific example of keto-enol tautomerization is the tautomerization between two tautomers of pentane-2,4-dione and 4-hydroxypent-3-en-2-one.

Unless otherwise specified, the terms "rich in one isomer", "enriched in isomers", "rich in one enantiomer" or "enriched in enantiomers" mean that the content of one isomer or enantiomer is less than 100%, and the content of the isomer or enantiomer is greater than or equal to 60%, or greater than or equal to 70%, or greater than or equal to 80%, or greater than or equal to 90%, or greater than or equal to 95%, or greater than or equal to 96%, or greater than or equal to 97%, or greater than or equal to 98%, or greater than or equal to 99%, or greater than or equal to 99.5%, or greater than or equal to 99.6%, or greater than or equal to 99.7%, or greater than or equal to 99.8%, or greater than or equal to 99.9%.

Unless otherwise specified, the term "isomer excess" or "enantiomeric excess" refers to the difference between the relative percentages of two isomers or two enantiomers. For example, if the content of one isomer or enantiomer is 90% and the content of the other isomer or enantiomer is 10%, the isomer or enantiomer excess (ee value) is 80%.

The optically active (R)- and (S)-isomers and D and L isomers can be prepared by chiral synthesis or chiral reagents or other conventional techniques. If an enantiomer of a compound of the present disclosure is desired, it can be prepared by asymmetric synthesis or derivatization with chiral auxiliary agents, in which the resulting diastereomeric mixture is separated, and the auxiliary groups are cleaved to provide desired pure enantiomer. Alternatively, when the molecule contains a basic functional group (such as an amino group) or an acidic functional group (such as a carboxyl group), it forms a diastereomeric salt with a suitable optically active acid or base, and then diastereomer separation is carried out through a conventional method known in the art, and then the pure enantiomers are recovered. In addition, the separation of enantiomers and diastereomers is usually accomplished through the use of chromatography, which employs a chiral stationary phase and is optionally combined with chemical derivatization (for example, the formation of carbamates from amines).

The compounds of the present disclosure may contain unnatural proportions of atomic isotopes on one or more of the atoms constituting the compound. For example, compounds can be labeled with radioisotopes, such as tritium ($^3$H), iodine-125 ($^{125}$I) or C-14 ($^{14}$C). For another example, deuterated drugs can be formed by replacing hydrogen with deuterium. The bond between deuterium and carbon is stronger than that of ordinary hydrogen and carbon. Compared with non-deuterated drugs, deuterated drugs have the advantages of reducing toxic side effects, increasing drug stability, enhancing the efficacy, extending the biological half-life of drugs and the like. All changes in the isotopic composition of the compounds of the present disclosure, whether radioactive or not, are included in the scope of the present disclosure.

The term "optional" or "optionally" refers to the event or condition described later that may but not necessarily occur, and the description includes the situation in which the event or condition occurs and the situation in which the event or condition does not occur.

The term "substituted" means that any one or more hydrogen atoms on a specific atom are replaced by substituents, and may include deuterium and hydrogen variants, as long as the valence of the specific atom is normal and the substituted compound is stable. When the substituent is oxygen (that is =O), it means that two hydrogen atoms are replaced. Oxygen substitution does not occur on aromatic groups. The term "optionally substituted" means that it can be substituted or unsubstituted. Unless otherwise specified, the type and number of substituents can be arbitrary on the basis that they can be realized chemically.

When any variable (such as R) occurs more than once in the composition or structure of a compound, the definition thereof in each case is independent. Thus, for example, if a group is substituted by 0-2 R, the group can optionally be substituted by up to two R, and there are independent options for R in each case. In addition, combinations of substituents and/or variants thereof are only permitted if such combinations result in stable compounds.

When the number of a linking group is 0, such as —(CRR)$_0$—, it means that the linking group is a single bond.

When one of the variables is selected from a single bond, it means that the two groups connected are directly connected. For example, when L in A-L-Z represents a single bond, it means that the structure is actually A-Z.

When a substituent is vacant, it means that the substituent is absent. For example, when X in A-X is vacant, it means that the structure is actually A. When the listed substituents do not indicate which atom is connected to the substituted group, such substituents can be bonded via any atom. For example, as a substituent, a pyridyl group can be connected to the substituted group through any carbon atom on the pyridine ring.

When the linking group listed does not indicate the linking direction, the linking direction is arbitrary. For example, the linking group L in

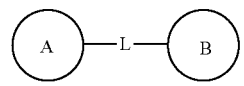

is -MW- and -MW- can connect ring A and ring B in the same direction as the reading order from left to right to form

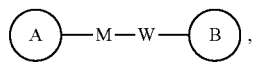, and also can connect ring A and ring B in the opposite direction as the reading order from left to right to form

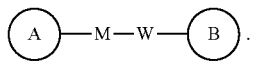

The combination of linking group, substituent and/or variants thereof is only allowed if such combination will produce stable compounds.

Unless otherwise specified, when a group has one or more connectable sites, any one or more sites of the group can be connected to other groups through chemical bonds. The chemical bond between the site and other groups can be represented by a straight solid bond

a straight dashed bond

or a wavy line

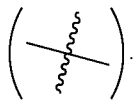

For example, the straight solid bond in —OCH₃ indicates that it is connected to other groups through the oxygen atom in the group; the straight dashed bond in

indicates that it is connected to other groups through the two ends of the nitrogen atom in the group; the wavy lines in

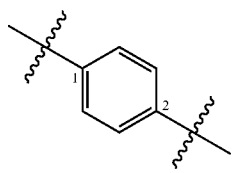 [SMILES: *c1ccc(*)cc1]

indicate that the phenyl group is connected to other groups through the 1 and 2-position carbon atoms.

Unless otherwise specified, the term "$C_{1-3}$ alkyl" is used to denote a linear or branched saturated hydrocarbon group composed of 1 to 3 carbon atoms. The $C_{1-3}$ alkyl includes $C_{1-2}$ and $C_{2-3}$ alkyl and the like; it can be monovalent (such as methyl), divalent (such as methylene) or multivalent (such as methine). Examples of $C_{1-3}$ alkyl groups include, but not limited to, methyl (Me), ethyl (Et), propyl (including n-propyl and isopropyl), and the like.

Unless otherwise specified, $C_{n-n+m}$ or $C_n$-$C_{n+m}$ includes any specific case of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$, and $C_{12}$, and includes any range from n to n+m, for example, $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, and $C_{9-12}$ and the like. In the same way, n-membered to n+m-membered means that the number of atoms in the ring is from n to n+m, for example, a 3-12-membered ring includes a 3-membered ring, 4-membered ring, 5-membered ring, 6-membered ring, 7-membered ring, 8-membered ring, 9-membered ring, 10-membered ring, 11-membered ring, and 12-membered ring, and includes any range from n to n+m, for example, 3-12 membered ring includes 3-6 membered ring, 3-9 membered ring, 5-6 membered ring, 5-7 membered ring, 6-7 membered ring, 6-8 membered ring, and 6-10 membered ring and the like.

The term "leaving group" refers to a functional group or atom that can be replaced by another functional group or atom through a substitution reaction (for example, a nucleophilic substitution reaction). For example, representative leaving groups include triflate; chlorine, bromine, iodine; sulfonate, such as mesylate, toluene sulfonate, p-bromobenzenesulfonate, p-toluene sulfonate and the like; acyloxy groups, such as acetoxy, trifluoroacetoxy and the like.

The term "protecting group" includes, but not limited to, "amino protecting group", "hydroxy protecting group" or "sulfydryl protecting group". The term "amino protecting group" refers to a protecting group suitable for preventing side reactions at the amino nitrogen position. Representative amino protecting groups include but not limited to: formyl; acyl, such as alkanoyl (such as acetyl, trichloroacetyl or trifluoroacetyl); alkoxycarbonyl, such as tert-butoxycarbonyl (Boc); arylmethyloxycarbonyl, such as benzyloxycarbonyl (Cbz) and 9-fluorenylmethyloxycarbonyl (Fmoc); arylmethyl, such as benzyl (Bn), trityl (Tr), 1,1-di-(4'-methoxyphenyl)methyl; silyl, such as trimethylsilyl (TMS) and tert-butyldimethylsilyl (TBS) and so on. The term "hydroxy protecting group" refers to a protecting group suitable for preventing side reactions of the hydroxyl group. Representative hydroxy protecting groups include, but not limited to: alkyl, such as methyl, ethyl and tert-butyl; acyl, such as alkanoyl groups (such as acetyl); arylmethyl, such as benzyl (Bn), p-methyloxybenzyl (PMB), 9-fluorenylmethyl (Fm) and diphenylmethyl (diphenylmethyl, DPM); silyl, such as trimethylsilyl (TMS) and tert-butyl dimethylsilyl (TBS) and so on.

The compounds of the present disclosure can be prepared by a variety of synthetic methods well known to those skilled in the art, including the specific embodiments listed below, the embodiments formed by their combination with other chemical synthesis methods and equivalent alternatives well known to the skilled in the art, preferred embodiments include but not limited to the examples of the present disclosure.

The solvent used in the present disclosure is commercially available. The present disclosure uses the following abbreviations: aq stands for water; HATU stands for O-(7-azabenzotriazol-1-yl)-N,N,N',N'-tetramethyluronium hexafluorophosphate; EDC stands for N-(3-dimethylaminopropyl)-N'-ethylcarbodiimide hydrochloride; m-CPBA stands for 3-chloroperoxybenzoic acid; eq stands for equivalent, equivalence; CDI stands for carbonyl diimidazole; DCM stands for dichloromethane; PE stands for petroleum ether; DIAD stands for diisopropyl azodicarboxylate; DMF stands for N,N-dimethylformamide; DMSO stands for dimethyl sulfoxide; EtOAc stands for ethyl acetate; EtOH stands for ethanol; MeOH stands for methanol; CBz stands for benzyloxycarbonyl, which is an amine protecting group; BOC stands for tert-butoxycarbonyl which is an amine protecting group; HOAc stands for acetic acid; NaCNBH$_3$ stands for sodium cyanoborohydride; r.t. stands for room temperature; O/N stands for overnight; THF stands for tetrahydrofuran; Boc$_2$O stands for di-tert-butyl dicarbonate; TFA stands for trifluoroacetic acid; DIPEA stands for diisopropylethylamine; SOCl$_2$ stands for thionyl chloride; CS$_2$ stands for carbon disulfide; TsOH stands for p-toluenesulfonic acid; NFSI stands for N-fluoro-N-(benzenesulfonyl)benzenesulfonamide; n-Bu$_4$NF stands for tetrabutylammonium fluoride; iPrOH stands for 2-propanol; mp stands for melting point; LDA stands for lithium diisopropylamide; Et represents ethyl.

The compounds are named according to the conventional naming principles in the field or using ChemDraw® software, and the commercially available compounds use the supplier catalog name.

DETAILED DESCRIPTION

The present disclosure will be described in detail through the following examples, but it is not meant to impose any disadvantageous restriction on the present disclosure. The present disclosure has been described in detail herein, and its specific embodiments are also disclosed. For those skilled in the art, it is obvious to make various changes and improvements to the specific embodiment of the invention without departing from the spirit and scope of the invention.

Reference Example 1: Fragments A-1, A-2

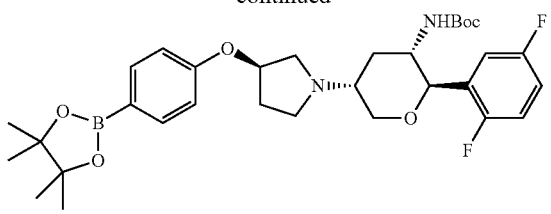

A-1

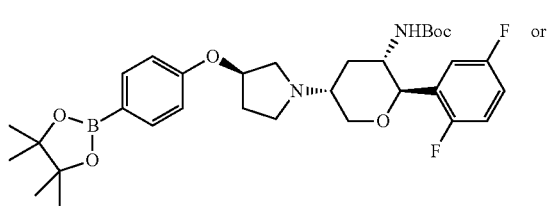

or

A-2

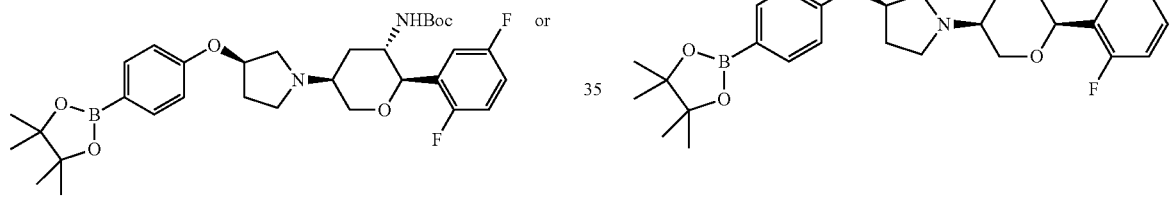

Synthetic Route:

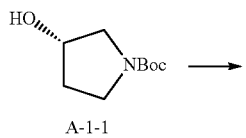

A-1-1

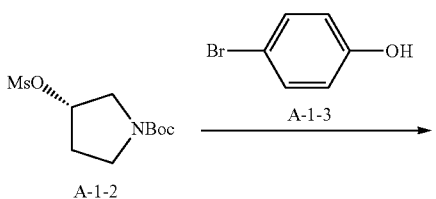

A-1-2    A-1-3

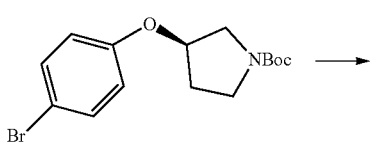

A-1-4

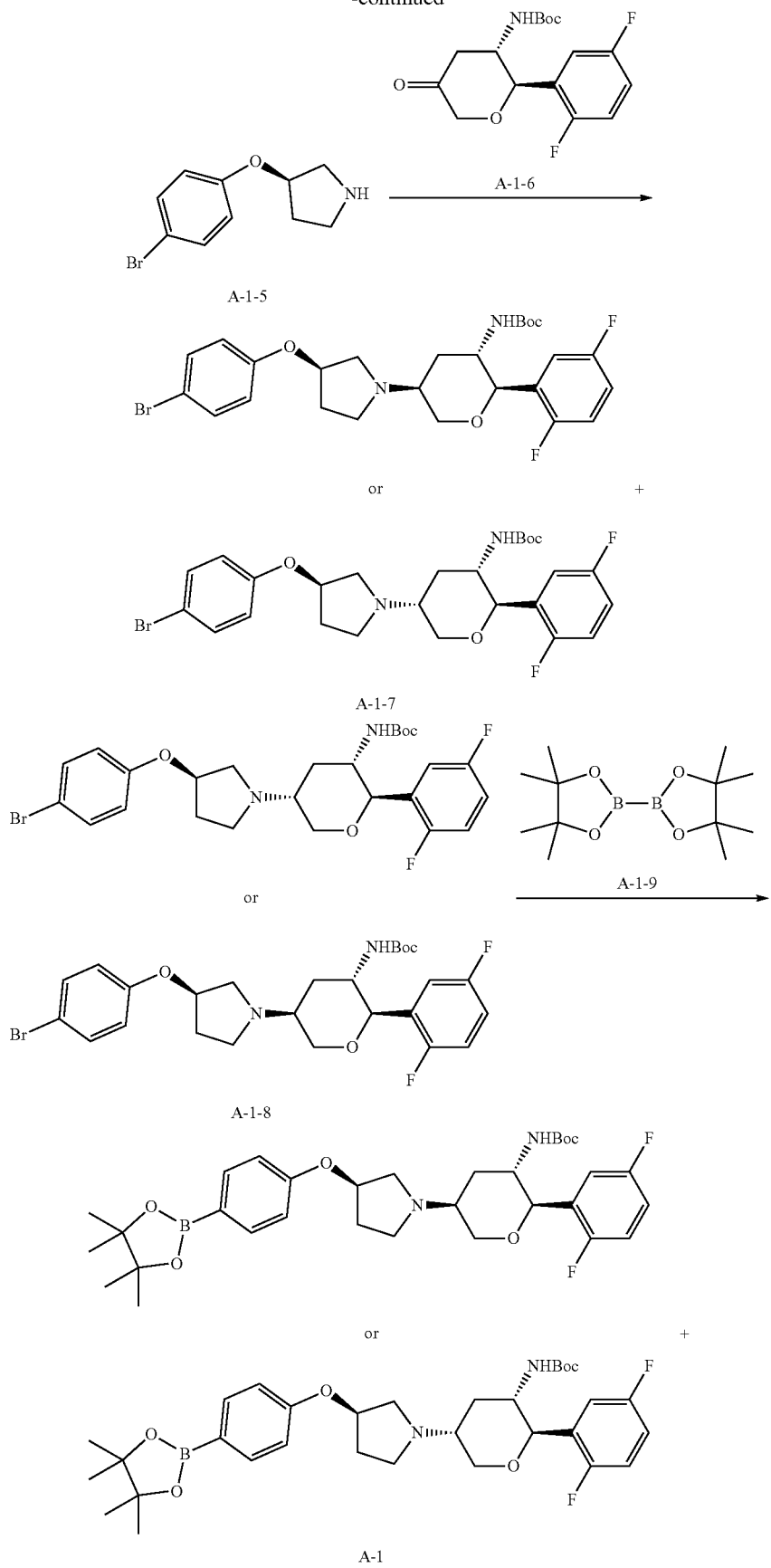

-continued

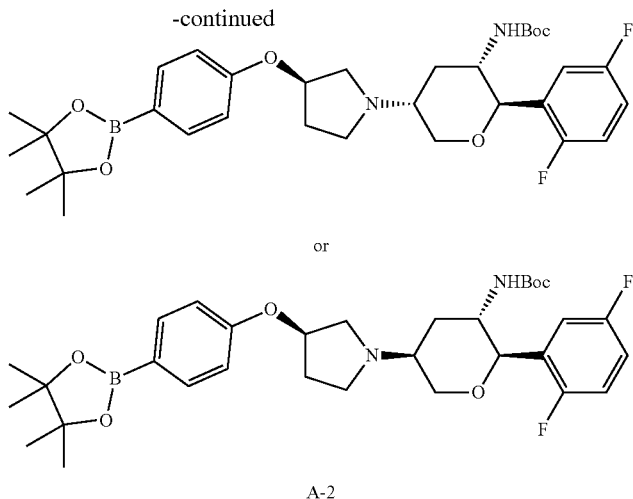

A-2

Step 1: Synthesis of Compound A-1-2.

Compound A-1-1 (25 g, 133.52 mmol, 1 eq) was dissolved in dichloromethane (110 mL), and added with triethylamine (27.02 g, 267.04 mmol, 37.17 mL, 2 eq). The reaction was cooled to 0° C., and methanesulfonyl chloride (15.30 g, 133.52 mmol, 10.33 mL, 1 eq) was added dropwise to the reaction at 0° C. After the addition was completed, the reaction temperature was raised to 15° C. and stirred at 15° C. for 3 hours. After the reaction was completed, the reaction was cooled to 0° C., and added slowly with water (100 mL) at 0° C. to quench the reaction. The mixture was extracted with dichloromethane (100 mL×2), the organic phase was combined and washed with saturated brine (100 mL), dried over anhydrous sodium sulfate and filtered, and the filtrate was concentrated under reduced pressure to obtain compound A-1-2.

Step 2: Synthesis of Compound A-1-4.

A mixture of Compound A-1-2 (6.00 g, 22.61 mmol, 1.00 eq), compound A-1-3 (3.91 g, 22.61 mmol, 1.00 eq), and cesium carbonate (14.73 g, 45.22 mmol, 2.00 eq) in N,N-dimethylformamide (10.00 mL) was heated to 80° C., and stirred at 80° C. for 3 hours. After the reaction was completed, the reaction was added with water (50 mL). The mixture was extracted with ethyl acetate (30 mL×3), and the organic phases were combined and washed with water (30 mL×3) and saturated brine (30 mL) sequentially, dried with anhydrous sodium sulfate and filtered, and the filtrate was concentrated under reduced pressure to obtain a crude product. The crude product was purified by column chromatography to obtain compound A-1-4. $^1$H NMR (400 MHz, CD$_3$OD) δ 7.41-7.34 (m, 2H), 6.78-6.74 (m, 2H), 4.15-4.12 (m, 1H), 3.64-3.52 (m, 4H), 2.18-2.07 (m, 2H), 1.157 (s, 9H).

Step 3: Synthesis of Compound A-1-5.

Compound A-1-4 (3.00 g, 8.77 mmol, 1.00 eq) was dissolved in a solution of hydrogen chloride in ethyl acetate (10 mL, 4M). The reaction system was reacted at 20° C. for 1 hour. After the reaction was completed, the reaction was diluted with water (30 mL), and the mixture was washed with ethyl acetate (20 mL). The aqueous phase was adjusted to pH=7 with saturated aqueous sodium bicarbonate solution. The aqueous phase was extracted with ethyl acetate (30 mL). The organic phase was washed with saturated brine (20 mL). The organic phase was dried over anhydrous sodium sulfate and concentrated under reduced pressure to obtain the crude product of compound A-1-5. $^1$H NMR (400 MHz, CD$_3$OD) δ 7.39-7.35 (m, 2H), 6.76-6.74 (m, 2H), 5.30 (m, 1H), 3.31-3.13 (m, 4H), 2.15-2.05 (m, 2H).

Step 4: Synthesis of Compounds A-1-7 and A-1-8.

Compound A-1-5 (2 g, 7.18 mmol, 1 eq), compound A-1-6 (2.58 g, 7.90 mmol, 1.1 eq) were dissolved in dichloromethane (20 mL) and methanol (4 mL). The reaction was added with acetic acid (43.11 mg, 717.95 μmol, 41.06 μL, 0.1 eq), followed by sodium triacetoxyborohydride (3.04 g, 14.36 mmol, 2 eq). The reaction was stirred at 15° C. for 2 hours. After the reaction was completed, the reaction was concentrated under reduced pressure, and the residue was diluted with water (50 mL) and extracted with dichloromethane (50 mL×2). The organic phases were combined and washed with saturated brine (30 mL). The organic phase was dried over anhydrous sodium sulfate and concentrated under reduced pressure to obtain a crude product. The crude product was purified by column chromatography (petroleum ether/ethyl acetate=3/1) to obtain compound A-1-7 (Rf=0.5) ($^1$H NMR (400 MHz, CDCl$_3$) δ 7.38 (d, J=9.2 Hz, 2H), 7.34-7.28 (m, 1H), 7.03-6.87 (m, 2H), 6.76 (d, J=8.8 Hz, 2H), 4.93-4.77 (m, 1H), 4.49-4.28 (m, 2H), 4.15 (br d, J=12.4 Hz, 1H), 4.10-3.97 (m, 1H), 3.59 (d, J=12.0 Hz, 1H), 3.50-3.35 (m, 1H), 3.08-2.89 (m, 1H), 2.76-2.56 (m, 2H), 2.50 (br s, 1H), 2.45-2.37 (m, 1H), 2.36-2.26 (m, 1H), 2.12-1.94 (m, 1H), 1.28 (br s, 9H)) and compound A-1-8 (Rf=0.4) respectively ($^1$H NMR (400 MHz, CDCl$_3$) δ 7.37 (d, J=8.8 Hz, 2H), 7.24-7.17 (m, 1H), 7.02-6.89 (m, 2H), 6.74 (d, J=8.8 Hz, 2H), 4.85-4.74 (m, 1H), 4.51-4.40 (m, 1H), 4.31-4.25 (m, 1H), 4.24-4.18 (m, 1H), 3.82-3.65 (m, 1H), 3.45-3.33 (m, 1H), 3.04-2.83 (m, 3H), 2.65-2.50 (m, 2H), 2.50-2.41 (m, 1H), 2.38-2.23 (m, 1H), 2.06-1.93 (m, 1H), 1.26 (br s, 9H)).

Step 5: Synthesis of Compound A-1.

Compound A-1-8 (15 g, 27.10 mmol, 1 eq), compound A-1-9 (13.77 g, 54.21 mmol, 2 eq), potassium acetate (7.98 g, 81.31 mmol, 3 eq), [1,1-bis(diphenylphosphorus)ferrocene]palladium dichloride (1.98 g, 2.71 mmol, 0.1 eq) were sequentially added to the anhydrous dioxane (20 mL), and reacted at 90° C. for 2 hours under protection of nitrogen. After the reaction was completed, the reaction was concentrated under reduced pressure, the residue was diluted with water (200 mL), and the mixture was extracted with dichloromethane (200 mL×2). The organic phases were combined and washed with saturated brine (100 mL×2), dried over anhydrous sodium sulfate and concentrated under reduced pressure to obtain a crude product. The crude product was purified by column chromatography to obtain compound A-1. ¹H NMR (400 MHz, CDCl₃) δ7.74 (d, J=8.8 Hz, 2H), 7.24-7.15 (m, 1H), 7.01-6.90 (m, 2H), 6.85 (d, J=8.8 Hz, 2H), 4.93-4.83 (m, 1H), 4.46 (br d, J=9.6 Hz, 1H), 4.27 (br d, J=9.6 Hz, 1H), 4.24-4.18 (m, 1H), 3.81-3.68 (m, 1H), 3.38 (br t, J=10.8 Hz, 1H), 3.05-2.96 (m, 1H), 2.93 (br d, J=3.2 Hz, 2H), 2.63-2.49 (m, 2H), 2.46 (br d, J=11.6 Hz, 1H), 2.39-2.27 (m, 1H), 2.05-1.95 (m, 1H), 1.51 (q, J=12.0 Hz, 1H), 1.34 (s, 12H), 1.26 (s, 9H).

Step 6: Synthesis of Compound A-2.

Compound A-1-7 (3.20 g, 5.78 mmol, 1 eq), compound A-1-9 (2.20 g, 8.67 mmol, 1.5 eq), potassium acetate (1.70 g, 17.35 mmol, 3 eq), [1,1-bis(diphenylphosphino)ferrocene]palladium(II)dichloride dichloromethane adduct (472.19 mg, 578.21p mol, 0.1 eq) were added to anhydrous dioxane (30 mL) and the mixture was stirred at 90° C. for 16 hours under nitrogen protection. After the reaction was completed, the reaction solution was diluted with water (50 mL), and the mixture was extracted with dichloromethane (50 mL×2). The organic phases were combined and washed with saturated brine (50 mL×2), dried over anhydrous sodium sulfate and concentrated under reduced pressure to obtain a crude product. The crude product was purified by column chromatography to obtain compound A-2. ¹HNMR (400 MHz, CDCl₃) δ 7.74 (d, J=8.4 Hz, 2H), 7.34-7.25 (m, 1H), 7.00-6.90 (m, 2H), 6.86 (d, J=8.4 Hz, 2H), 5.00-4.86 (m, 1H), 4.50-4.35 (m, 2H), 4.18-4.07 (m, 2H), 4.06-9.95 (m, 1H), 3.57 (br d, J=12.0 Hz, 1H), 3.54-3.44 (m, 1H), 3.08-2.93 (m, 1H), 2.72-2.63 (m, 1H), 2.62-2.54 (m, 1H), 2.43-2.36 (m, 1H), 2.35-2.26 (m, 1H), 2.04-1.96 (m, 1H), 1.33 (s, 12H), 1.23 (s, 9H).

Reference Example 2: Fragments A-3, A-4

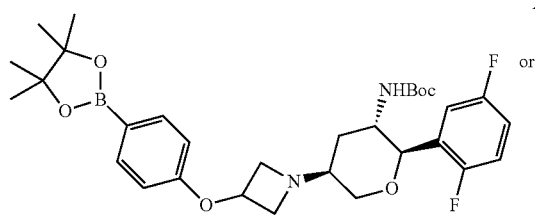

A-3

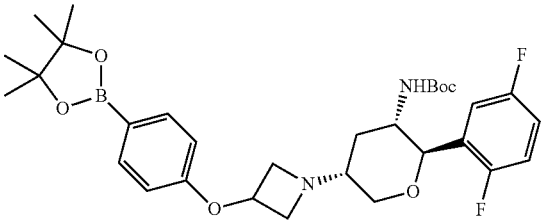

A-4

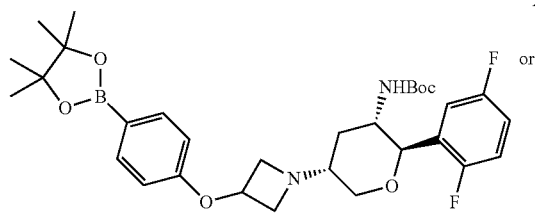

-continued

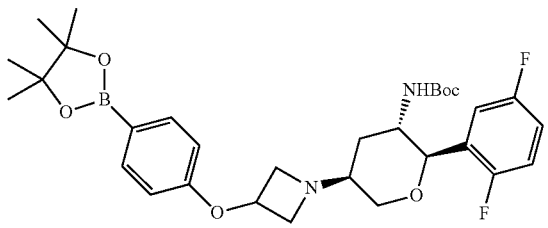

Synthetic Route:

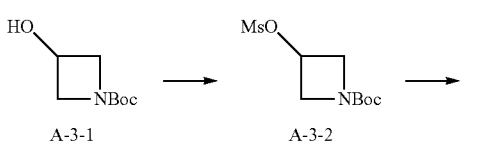

A-3-1  A-3-2

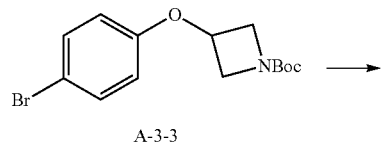

A-3-3

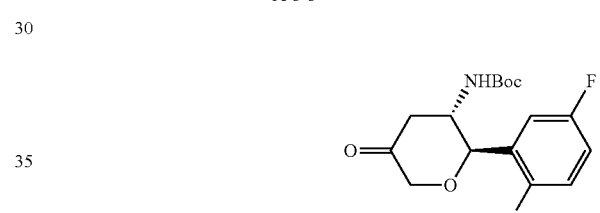

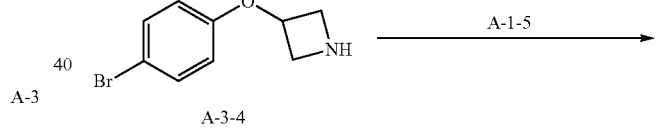

A-3-4

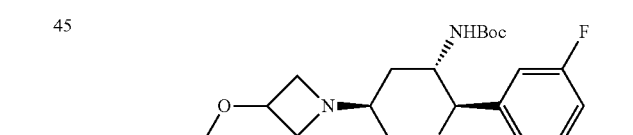

or

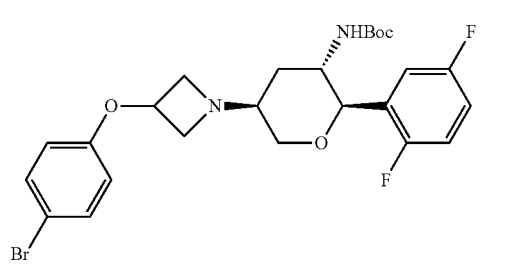

+

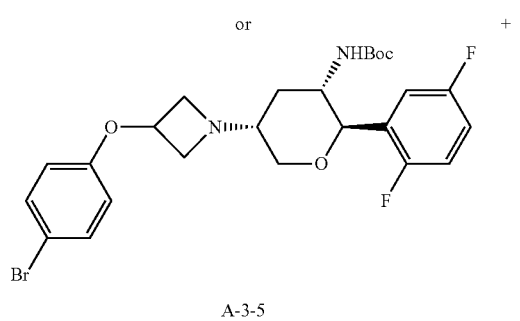

A-3-5

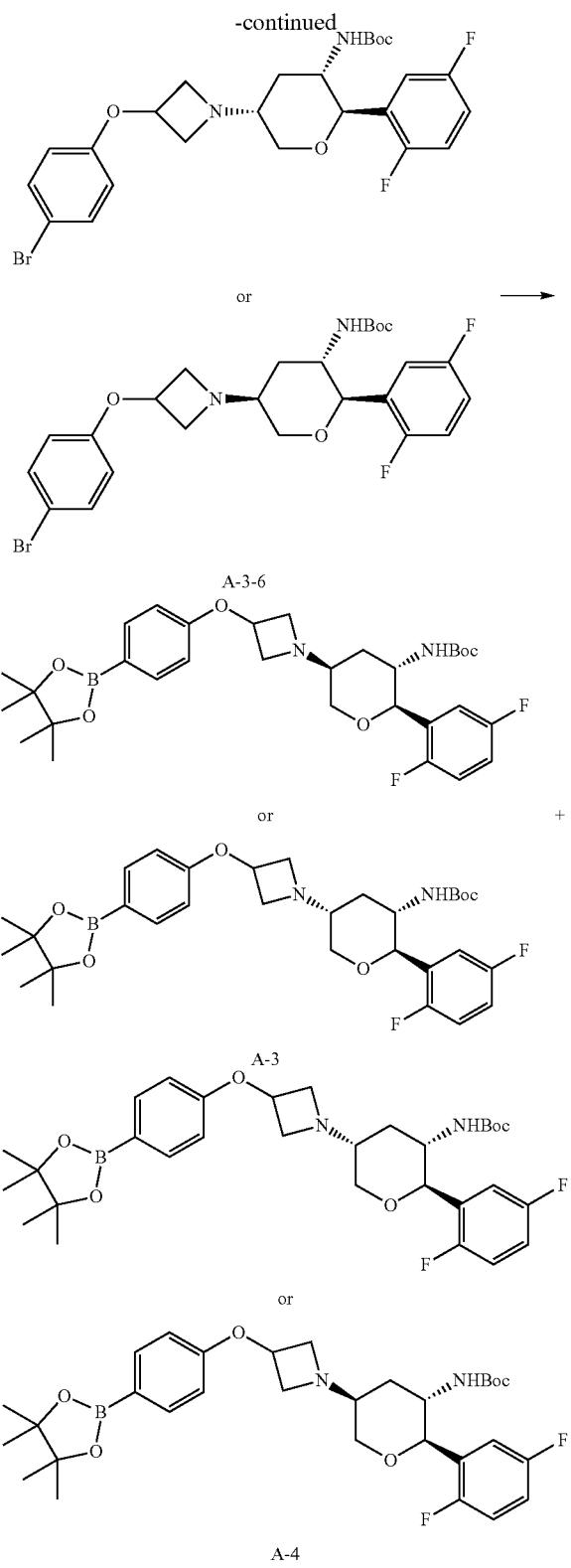

Step 1: Synthesis of Compound A-3-2.

Methanesulfonyl chloride (6.61 g, 57.73 mmol, 4.47 mL, 1.25 eq) was added to a mixture of compound A-3-1 (8 g, 46.19 mmol, 1 eq) and triethylamine (9.35 g, 92.37 mmol, 12.86 mL, 2 eq), in dichloromethane (120 mL), and stirred at 20° C. for 16 hours. After the reaction was completed, the mixture was slowly poured into 200 mL of ice water to quench the reaction. After reaction was quenched, the mixture was stirred for 10 minutes. The layers were separated by standing. The organic phase was separated and washed with water (50 mL), sodium hydroxide aqueous solution (1M, 50 mL), saturated brine (50 mL) sequentially, dried with anhydrous sodium sulfate and concentrated under reduced pressure to obtain the product compound A-3-2. $^1$H NMR (400 MHz, CDCl$_3$) δ 5.18 (tt, J=6.7, 4.1 Hz, 1H), 4.30-4.22 (m, 2H), 4.09 (dd, J=4.1, 0.9 Hz, 1H), 4.07 (dd, 1=4.1, 0.9 Hz, 1H), 3.05 (s, 3H), 1.38-1.47 (s, 9H).

Step 2: Synthesis of Compound A-3-3.

A mixture of 4-bromophenol (5.78 g, 33.43 mmol, 1.2 eq), A-3-2 (7 g, 27.86 mmol, 1 eq) and cesium carbonate (18.15 g, 55.71 mmol, 2 eq) in N, N-dimethyl formaldehyde (20 mL) was stirred at 80° C. for 16 hours. After the reaction was completed, the reaction was quenched by water (200 mL), and the mixture was extracted with ethyl acetate (100 mL×2). The organic phases were combined, washed with saturated brine (60 mL), dried over anhydrous sodium sulfate and concentrated under reduced pressure to obtain a crude product. Petroleum ether (60 mL) was added to the crude product, stirred at room temperature for 1 hour, and then filtered. The filtered cake was dissolved in dichloromethane and concentrated under reduced pressure to obtain compound A-3-3. $^1$H NMR (400 MHz, CDCl$_3$) δ 7.39 (d, J=8.5 Hz, 2H), 6.63 (d, J=8.8 Hz, 2H), 4.89-4.79 (m, 1H), 4.29 (dd, J=9.8, 6.3 Hz, 2H), 4.00 (d, J=4.0 Hz, 1H), 3.98 (d, J=4.0 Hz, 1H), 1.40-1.52 (s, 9H).

Step 3: Synthesis of Compound A-3-4.

Compound A-3-3 (11 g, 33.52 mmol, 1 eq) was added to a solution of hydrogen chloride in ethyl acetate (4M, 30 mL, 3.58 eq). The mixture was stirred at 20° C. for 16 hours. After the reaction was completed, the mixture was filtered. The filter cake was washed with ethyl acetate (30 mL) and then dissolved in dichloromethane (40 mL). The dichloromethane solution was concentrated under reduced pressure to obtain the hydrochloride salt of compound A-3-4.

Step 4: Synthesis of Compounds A-3-5 and A-3-6.

A mixture of the hydrochloride salt of compound A-3-4 (4.2 g, 15.88 mmol, 1 eq), compound A-1-5 (7.79 g, 23.81 mmol, 1.5 eq), magnesium sulfate (19.11 g, 158.76 mmol, 10 eq) and triethyl amine (1.61 g, 15.88 mmol, 2.21 mL, 1 eq) in N,N-dimethylacetamide (90 mL) was stirred at 20° C. for 1 hour, sodium cyanoborohydride (3.99 g, 63.50 mmol, 4 eq) was added and the reaction was continuously stirred for 15 hours. After the reaction was completed, the reaction was diluted with water (100 mL), and filtrated. The filter cake was washed with water (20 mL), dissolved with dichloromethane (20 mL). The organic phase was dried over anhydrous sodium sulfate and concentrated under reduced pressure to obtain crude product. The crude product was purified by column chromatography to obtain compound A-3-5 (petroleum ether:ethyl acetate=3:1, Rf=0.31) ($^1$H NMR (400 MHz, CDCl$_3$) δ 7.44-7.33 (m, 2H), 7.19 (m, 1H), 6.95 (m, 2H), 6.74-6.60 (m, 2H), 4.77 (br t, J=5.6 Hz, 1H), 4.45 (m, 1H), 4.25 (br d, J=10.0 Hz, 1H), 4.07-3.97 (m, 1H), 3.79 (m, 3H), 3.33-3.15 (m, 3H), 2.63 (m, J=10.8 Hz, 1H), 2.30 (br d, J=13.3 Hz, 1H), 1.34-1.21 (s, 9H)) and compound A-3-6 (petroleum ether:ethyl acetate=3:1, Rf=0.46) respectively ($^1$H NMR (400 MHz, CDCl$_3$) δ 7.38 (br d, J=9.0 Hz, 3H), 6.94 (m, 2H), 6.78-6.61 (m, 2H), 4.78 (m, 1H), 4.37 (m, 2H), 4.07-3.88 (m, 4H), 3.55 (br d, J=12.8 Hz, 1H), 3.07 (br s, 2H), 2.53 (br s, 1H), 2.17 (br d, J=11.5 Hz, 1H), 1.28 (s, 9H)).

Step 5: Synthesis of Compound A-3.

Compound A-3-5 (200 mg, 370.78 μmol, 1 eq), bis(pinacolato)diboron (235.39 mg, 926.94 μmol, 2.5 eq), [1,1-bis(diphenylphosphino)ferrocene]palladium(II)dichloride dichloromethane adduct (60.56 mg, 74.16 μmol, 0.2 eq) and potassium acetate (109.17 mg, 1.11 mmol, 3 eq) were added to anhydrous dioxane (5 mL) under nitrogen protection, and the mixture was reacted at 80° C. for 16 hours under nitrogen protection. After the reaction was completed, the reaction solution was quenched with water (10 mL), and extracted with dichloromethane (5 mL×2). The organic phases were combined and washed with water (5 mL) and concentrated under reduced pressure to obtain a crude product. The crude product was purified by column chromatography to obtain compound A-3. MS: 587.2 [M+1]$^+$.

Step 6: Synthesis of Compound A-4.

Compound A-3-6 (200 mg, 370.78 μmol, 1 eq), bis(pinacolato)diboron (112.99 mg, 444.93 μmol, 1.2 eq), [1,1-bis(diphenylphosphino)ferrocene]palladium(II)dichloride dichloromethane adduct (60.56 mg, 74.16 μmol, 0.2 eq), potassium acetate (72.78 mg, 741.55 μmol, 2 eq) were added to anhydrous dioxane (4 mL) under nitrogen protection, and the mixture was reacted at 80° C. for 16 hours under nitrogen protection. After the reaction was completed, the reaction was diluted with water (10 mL), and extracted with dichloromethane (10 mL×2). The organic phases were combined and washed with water (5 mL) and concentrated under reduced pressure to obtain a crude product. The crude product is purified by column chromatography to obtain compound A-4. MS: 587.1 [M+1]$^+$.

Reference Example 3: Fragment A-5

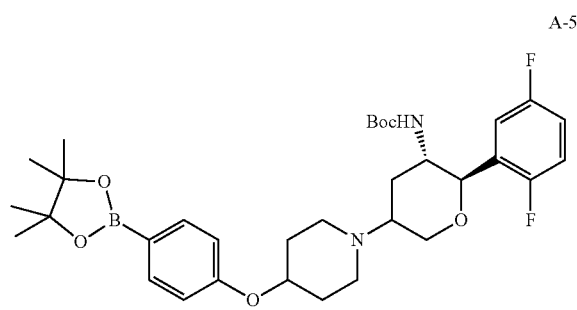 [SMILES: CC(C)(C)OC(=O)N[C@H]1CC(N2CCC(Oc3ccc(B4OC(C)(C)C(C)(C)O4)cc3)CC2)CO[C@@H]1c1cc(F)ccc1F]

A-5

Synthetic Route:

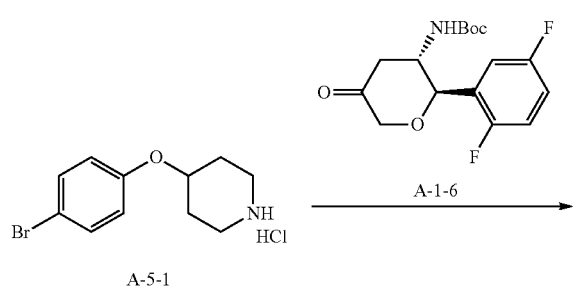

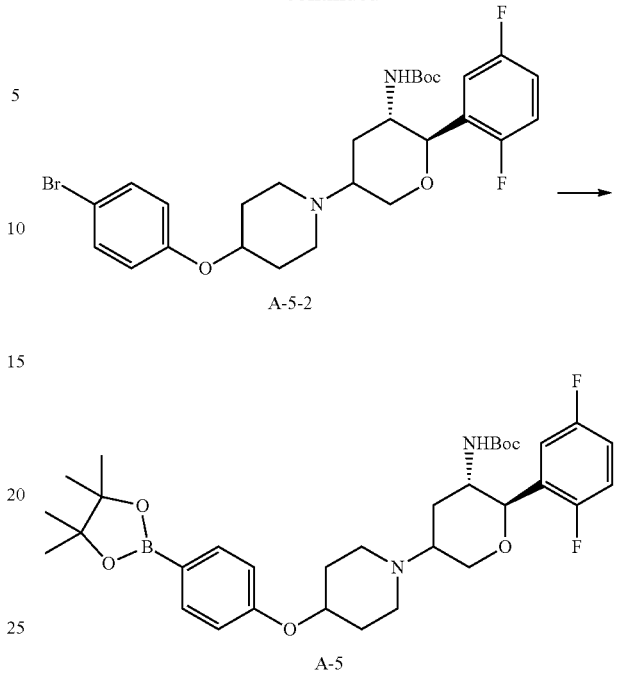

Step 1: Synthesis of Compound A-5-2.

A mixture of compound A-5-1 (4 g, 13.67 mmol, 1 eq), compound A-1-6 (6.71 g, 20.51 mmol, 1.5 eq), triethylamine (1.38 g, 13.67 mmol, 1.90 mL, 1 eq), and magnesium sulfate (16.46 g, 136.71 mmol, 10 eq) in N,N-dimethylacetamide (40 mL) was reacted at 20° C. for 1 hour, sodium cyanoborohydride (3.44 g, 54.68 mmol, 4 eq) was added to the reaction, and the reaction was continuously stirred for 15 hour. After the reaction was completed, the reaction was quenched with water (50 mL), and extracted with dichloromethane (20 mL×2). The organic phases were combined, washed with saturated brine (30 mL), dried over anhydrous sodium sulfate, and concentrated under reduced pressure to obtain crude product. The crude product was purified by column chromatography to obtain the product A-5-2, $^1$H NMR (400 MHz, CDCl$_3$) δ 7.40-7.22 (m, 2H), 7.21 (m, 1H), 7.02-6.89 (m, 2H), 6.83-6.76 (m, 2H), 4.48 (br d, J=8.8 Hz, 1H), 4.27 (br dd, J=7.3, 3.0 Hz, 2H), 4.24-4.18 (m, 1H), 3.70 (br d, J=8.0 Hz, 1H), 3.42 (t, J=10.9 Hz, 1H), 2.93-2.71 (m, 3H), 2.56-2.38 (m, 3H), 2.04-1.93 (m, 2H), 1.80 (m, 4.3 Hz, 2H), 1.70 (m, 1H), 1.50 (q, J=11.9 Hz, 1H), 1.32-1.18 (s, 9H).

Step 2: Synthesis of Compound A-5.

Compound A-5-2 (7 g, 12.34 mmol, 1 eq), bis(pinacolato)diboron (7.83 g, 30.84 mmol, 2.5 eq), potassium acetate (2.42 g, 24.67 mmol, 2 eq), and [1,1-bis(diphenylphosphino)ferrocene]palladium(II)dichloride dichloromethane adduct (2.01 g, 2.47 mmol, 0.2 eq) were added to anhydrous dioxane (40 mL), and the mixture was reacted at 80° C. for 16 hours under the protection of nitrogen. After the reaction was completed, the reaction solution was concentrated under reduced pressure, and the residue was dissolved in dichloromethane (20 mL), and washed with water (20 mL×3), dried over anhydrous sodium sulfate, and concentrated under reduced pressure to obtain a crude product. The crude product was purified by column chromatography to obtain the product A-5 MS: 615.3 [M+1]$^+$.

Reference Example 4: Fragments A-6, A-7
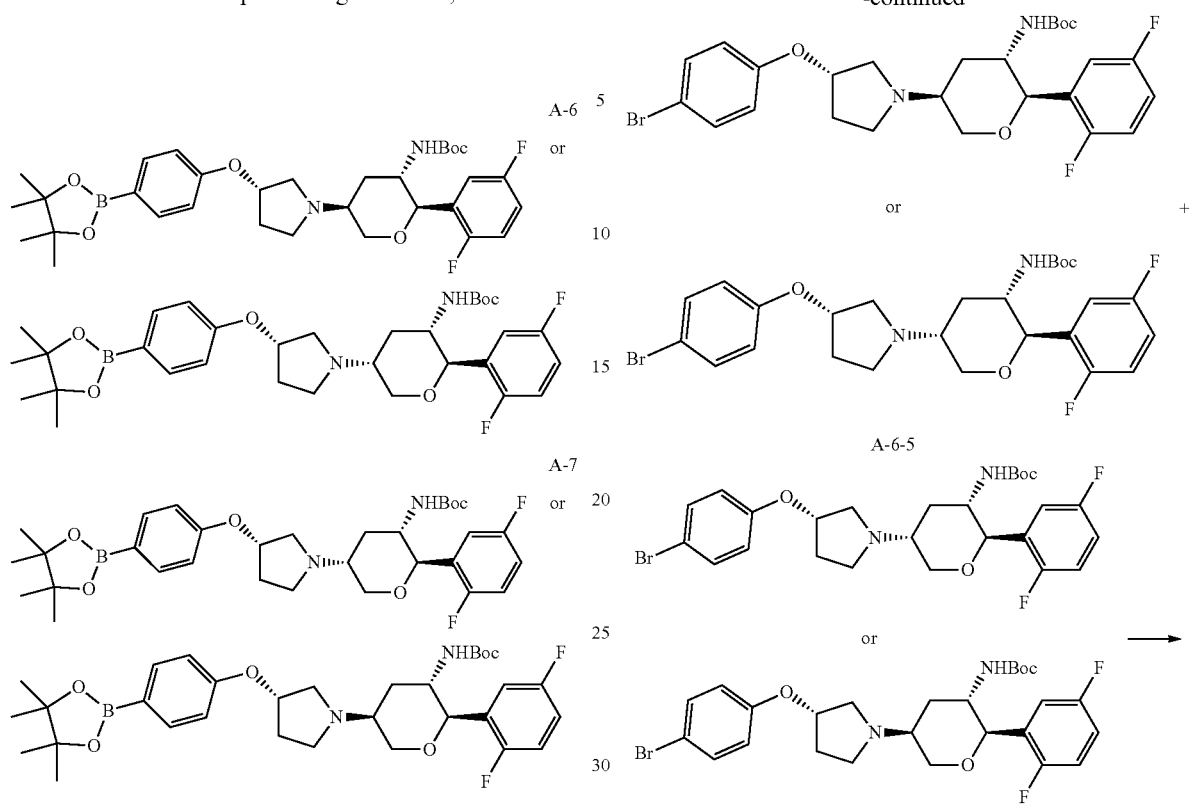
Synthetic Route:
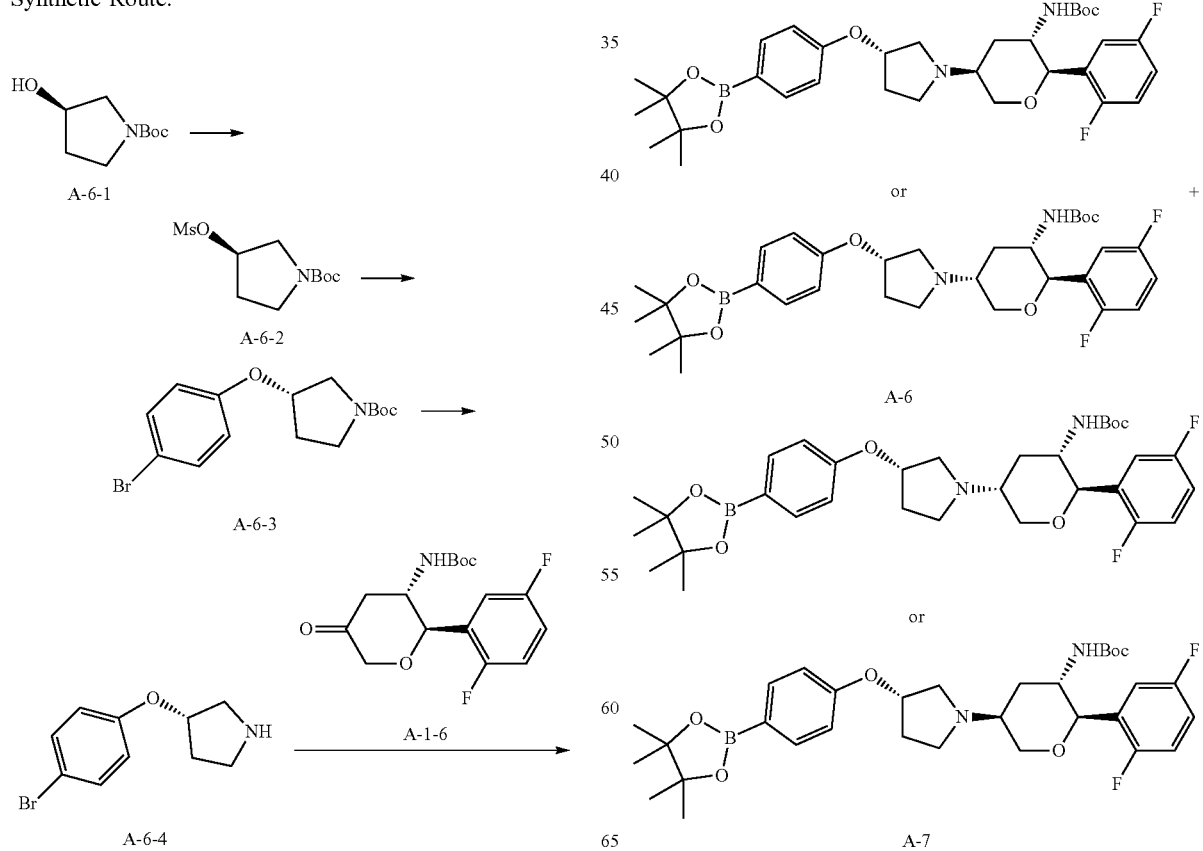

Step 1: Synthesis of Compound A-6-2.

Compound A-6-1 (10 g, 53.41 mmol, 1 eq) was dissolved in dichloromethane (100 mL), and then triethylamine (10.81 g, 106.82 mmol, 14.87 mL, 2 eq) was added to the solution. Methanesulfonyl chloride (6.12 g, 53.41 mmol, 4.13 mL, 1 eq) was added dropwise to the reaction at 0° C., and the reaction was stirred at 15° C. for 3 hours. After the reaction was completed, the reaction was quenched with water (20 mL) at 0° C., and then extracted with dichloromethane (30 mL×2). The organic phases were combined and washed with saturated brine (20 mL), dried with anhydrous sodium sulfate, and concentrated under reduced pressure to obtain A-6-2. $^1$H NMR (400 MHz, CDCl$_3$) δ 5.22-5.17 (m, 1H), 3.66-3.39 (m, 4H), 2.99 (s, 3H), 2.27-2.04 (m, 2H), 1.40 (s, 9H).

Step 2: Synthesis of Compound A-6-3.

Compound A-6-2 (6.5 g, 24.50 mmol, 1 eq), 4-bromophenol (5.09 g, 29.40 mmol, 1.2 eq), cesium carbonate (15.96 g, 49.00 mmol, 2 eq) were added to N, N-dimethyl formamide (70 mL). The mixture was stirred at 80° C. for 2 hours. After the reaction was completed, the mixture was added with water (500 mL), then extracted with ethyl acetate (500 mL×2). The organic phases were combined and washed with saturated brine (300 mL), dried over anhydrous sodium sulfate, filtered, the filter was concentrated under reduced pressure to obtain a crude product. The crude product was purified by column chromatography (petroleum ether:ethyl acetate=3:1) to obtain compound A-6-3. $^1$H NMR (400 MHz, CDCl$_3$) δ 7.37 (br t, J=8.2 Hz, 1H), 7.31-7.26 (m, 2H), 4.82 (br s, 1H), 3.63-3.43 (m, 4H), 2.21-2.05 (m, 2H), 1.47 (br d, J=3.3 Hz, 9H).

Step 3: Synthesis of Compound A-6-4.

A solution of hydrogen chloride in ethyl acetate (4M, 21.92 mL, 2 eq) was added to a solution of compound A-6-3 (15.00 g, 43.83 mmol, 1 eq) in ethyl acetate (100 mL), and the reaction was stirred at 15° C. for 2 hours. After the reaction was completed, the reaction was concentrated under reduced pressure. A mixed solution (petroleum ether:ethyl acetate=5:1, 100 mL) was added to the residue, and stirred for 2 hours. The mixture was filtered, and the filter cake was collected to obtain compound A-6-4. $^1$H NMR (400 MHz, CD$_3$OD) δ=7.48-7.44 (m, 2H), 6.98-6.93 (m, 2H), 5.21 (td, J=2.7, 5.8 Hz, 1H), 3.57-3.45 (m, 4H), 2.37-2.29 (m, 2H).

Step 4: Synthesis of Compound A-6-5 and A-6-6.

Acetic acid (86.23 mg, 1.44 mmol, 82.12 μL, 0.1 eq) was added to the solution of compound A-6-4 (4 g, 14.36 mmol, 1 eq), compound A-1-6 (5.17 g, 15.79 mmol, 1.1 eq) in dichloromethane (50 mL) and methanol (20 mL), followed by sodium triacetoxyborohydride (6.09 g, 28.72 mmol, 2 eq). The reaction was stirred at 15° C. for 2 hours. After the reaction was completed, the reaction solution was concentrated under reduced pressure. The residue was added with water (50 mL), and the mixture was extracted with dichloromethane (50 mL×2). The organic phases were combined and washed with saturated brine (30 mL), dried over anhydrous sodium sulfate and concentrated under reduced pressure to obtain a crude product. The crude product was purified by column chromatography (petroleum ether/ethyl acetate=3/1-2/1, containing one thousandth of triethylamine) to obtain compound A-6-5 (Rf=0.47)($^1$H NMR (400 MHz, DMSO) δ=7.44 (d, J=8.9 Hz, 2H), 7.21-7.07 (m, 3H), 6.91 (d, J=8.9 Hz, 2H), 6.83 (d, J=9.8 Hz, 1H), 4.94 (br s, 1H), 4.03 (q, J=7.1 Hz, 2H), 3.95-3.82 (m, 1H), 3.46 (br d, J=12.0 Hz, 1H), 3.00 (br dd, J=6.1, 10.0 Hz, 1H), 2.86-2.72 (m, 2H), 2.39-2.28 (m, 2H), 2.07 (br d, J=13.0 Hz, 1H), 1.91-1.82 (m, 1H), 1.77 (br t, J=11.7 Hz, 1H), 1.21-1.17 (m, 9H)) and compound A-6-6 (Rf=0.40) respectively ($^1$H NMR (400 MHz, DMSO) δ=7.43 (d, J=8.9 Hz, 2H), 7.20-7.12 (m, 3H), 6.95-6.85 (m, 3H), 4.84 (br s, 1H), 4.13-4.04 (m, 1H), 3.67-3.56 (m, 1H), 3.33 (d, J=9.5 Hz, 1H), 3.17 (br t, J=10.6 Hz, 1H), 2.88-2.81 (m, 1H), 2.81-2.72 (m, 1H), 2.81-2.71 (m, 1H), 2.48-2.36 (m, 2H), 2.30-2.20 (m, 1H), 2.13 (br d, J=11.9 Hz, 1H), 1.78-1.69 (m, 1H), 1.53 (q, J=11.9 Hz, 1H), 1.30-1.11 (m, 9H)).

Step 5: Synthesis of Compound A-6.

Compound A-6-5 (4.50 g, 8.13 mmol, 1 eq), bis(pinacolato)diboron (3.10 g, 12.20 mmol, 1.5 eq), potassium acetate (1.60 g, 16.26 mmol, 2 eq), and [1,1-bis(diphenylphosphorus)ferrocene]palladium dichloride (594.96 mg, 813.10 μmol, 0.1 eq) were added to anhydrous dioxane (50 mL) and the mixture was reacted at 90° C. for 2 hours under protection of nitrogen. After the reaction was completed, the reaction was concentrated under reduced pressure and the residue was diluted with water (50 mL), extracted with dichloromethane (50 mL×2). The organic phases were combined and washed with saturated brine (30 mL), dried over anhydrous sodium sulfate, filtered, and concentrated under reduced pressure to obtain a crude product. The crude product was purified by column chromatography (dichloromethane/methanol=20:1) to obtain compound A-6. $^1$H NMR (400 MHz, CDCl$_3$) δ=7.71-7.54 (m, 2H), 7.24 (br s, 1H), 6.86 (br s, 2H), 6.79 (br d, J=8.4 Hz, 2H), 5.23 (s, 1H), 4.86 (br s, 1H), 4.34 (br s, 2H), 4.09 (br d, J=12.1 Hz, 1H), 3.50 (br d, J=12.3 Hz, 1H), 2.84 (br s, 1H), 2.75-2.59 (m, 2H), 2.41 (br s, 1H), 2.36-2.11 (m, 3H), 1.98 (br d, J=7.3 Hz, 1H), 1.26 (s, 9H), 1.23-1.17 (m, 12H).

Step 6: Synthesis of Compound A-7.

Compound A-6-6 (3.40 g, 6.14 mmol, 1 eq), bis(pinacolato)diboron (2.34 g, 9.22 mmol, 1.5 eq), potassium acetate (1.21 g, 12.29 mmol, 2 eq) and [1,1-bis(diphenylphosphino)ferrocene]palladium(II)dichloride dichloromethane adduct (501.70 mg, 614.35 μmol, 0.1 eq) were added to anhydrous dioxane (50 mL), and the mixture was stirred at 90° C. for 2 hours under protection of nitrogen. After the reaction was completed, the reaction was concentrated under reduced pressure. The residue was diluted with water (50 mL), and extracted with dichloromethane (50 mL×2). The organic phases were combined and washed with saturated brine (30 mL), dried over anhydrous sodium sulfate and concentrated under reduced pressure to obtain a crude product. The crude product was purified by column chromatography (dichloromethane/methanol=20:1) to obtain compound A-7. $^1$H NMR (400 MHz, CDCl$_3$) δ=7.70-7.59 (m, 2H), 7.13 (br s, 1H), 6.87 (br s, 2H), 6.82-6.70 (m, 2H), 5.25-5.20 (m, 1H), 4.79 (br s, 1H), 4.39 (br d, J=8.9 Hz, 1H), 4.17 (br d, J=13.5 Hz, 1H), 3.66 (br d, J=8.3 Hz, 1H), 3.43-3.30 (m, 1H), 2.86 (br d, J=19.4 Hz, 3H), 2.51 (br s, 2H), 2.38 (br d, J=10.9 Hz, 1H), 2.24 (br d, J=6.6 Hz, 1H), 1.95 (br d, J=6.4 Hz, 1H), 1.26 (s, 9H), 1.18 (br s, 12H).

Reference Example 5: Fragment A-8, A-9
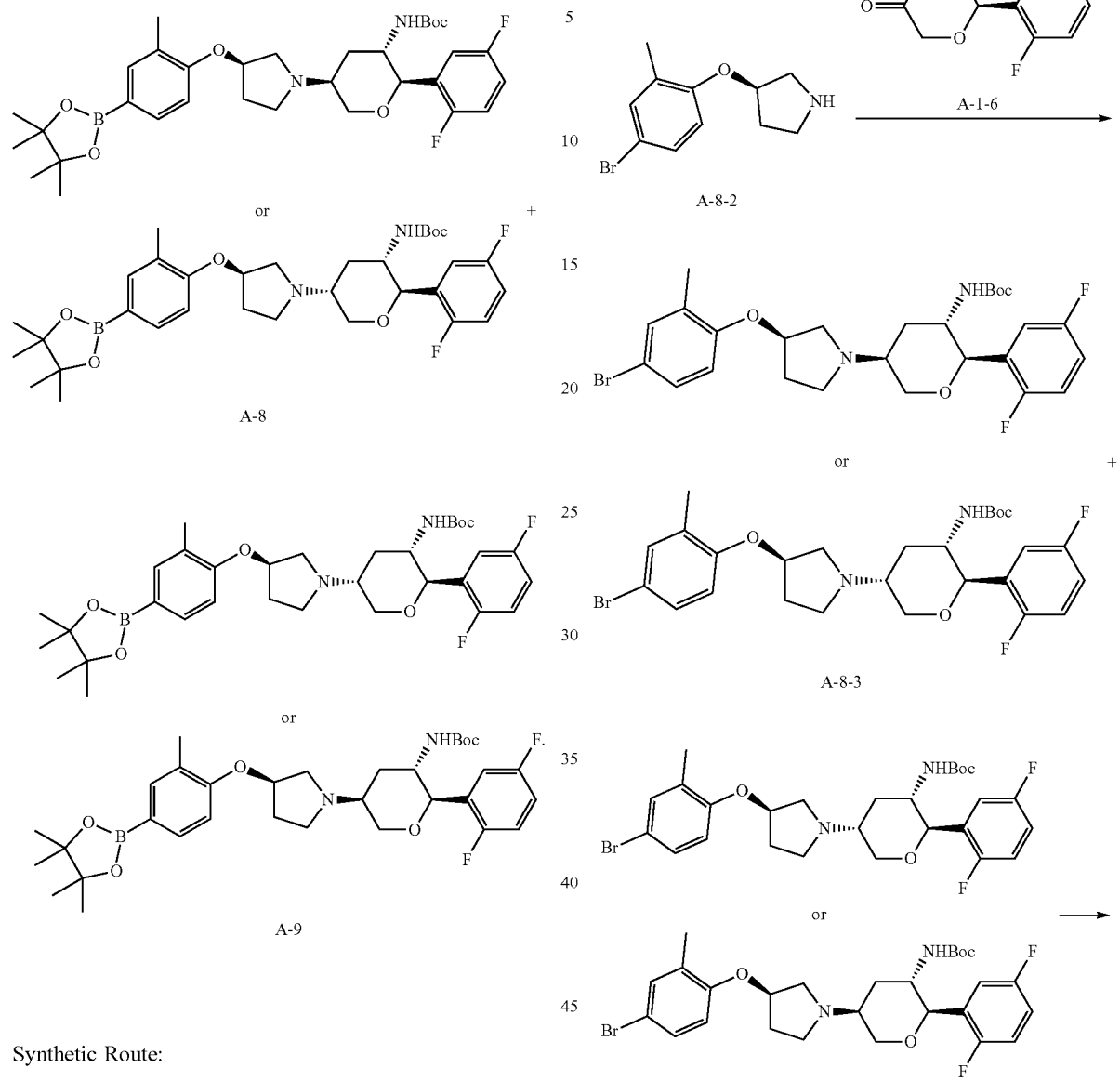
Synthetic Route:
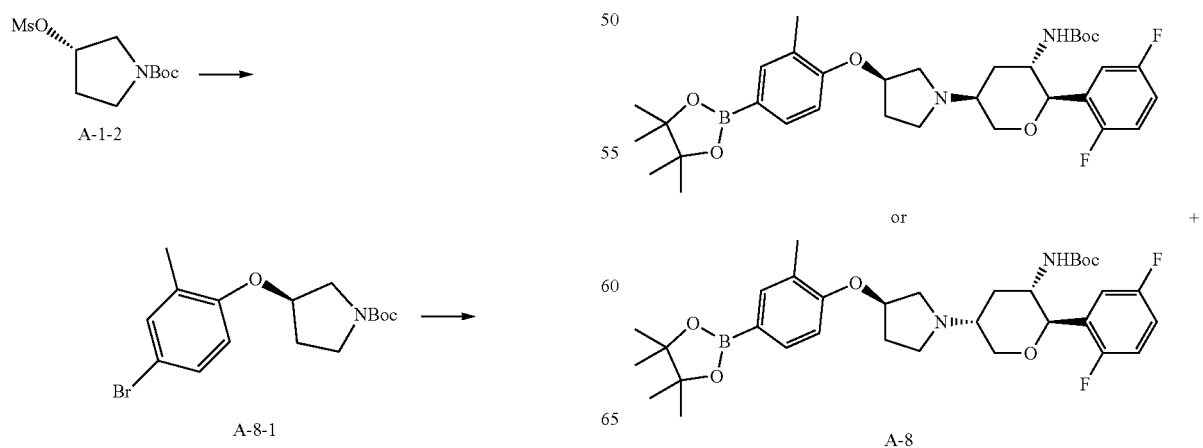

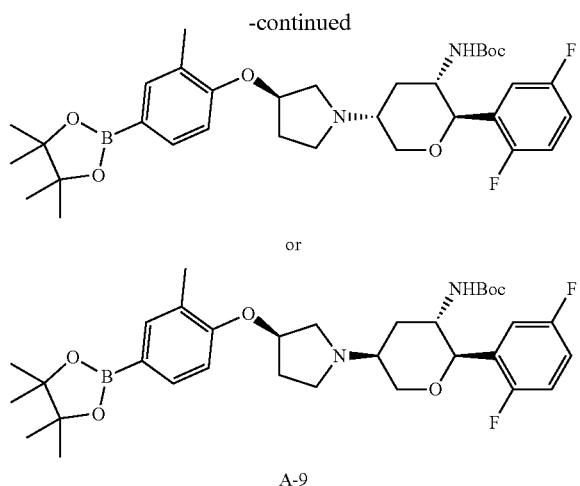

A-9

Step 1: Synthesis of Compound A-8-1.

Compound A-1-2 (11.5 g, 43.34 mmol, 1.00 eq), 2-methyl-4-bromophenol (8.11 g, 43.34 mmol, 1.00 eq) and potassium carbonate (11.98 g, 86.69 mmol, 2.00 eq) were added to N,N-dimethylformamide (100.00 mL). The reaction was stirred at 80° C. for 3 hours. After the reaction was completed, the mixture was added with water (500 mL), extracted with ethyl acetate (250 mL×2), and the organic phases were combine and washed with 1M aqueous sodium hydroxide solution (200 mL×2) and saturated brine (200 mL×2) sequentially, dried over anhydrous sodium sulfate and concentrated under reduced pressure to obtain a crude product. The crude product was purified by column chromatography to obtain compound A-8-1. $^1$H NMR (400 MHz, CDCl$_3$) δ 7.22-7.01 (m, 2H), 6.67-6.52 (m, 1H), 4.10-3.97 (m, 1H), 3.57-3.35 (m, 3H), 2.97 (s, 1H), 2.16-2.02 (m, 3H), 2.01-1.82 (m, 1H), 2.02-1.76 (m, 1H), 1.40 (s, 9H).

Step 2: Synthesis of Compound A-8-2.

Compound A-8-1 (14.8 g, 33.57 mmol, 1.00 eq) was dissolved in a solution of hydrogen chloride in ethyl acetate (50 mL, 4M), and the reaction was carried out at 15° C. for 3 hours. After the reaction was completed, the mixture was concentrated under reduced pressure. The residue was added with 10 mL of petroleum ether and 1 mL of ethyl acetate. The mixture was stirred for 1 hour, and then filtered. The filter cake was collected to obtain compound A-8-2. $^1$H NMR (400 MHz, DMSO-d6) δ 7.38-7.29 (m, 2H), 6.96 (d, J=8.8 Hz, 1H), 5.15 (s, 1H), 3.90 (br t, J=5.2 Hz, 1H), 3.44 (br s, 2H), 3.24 (br d, J=10.8 Hz, 1H), 2.24-2.17 (m, 1H), 2.15 (s, 3H), 2.14-2.08 (m, 1H).

Step 3: Synthesis of Compounds A-8-3 and A-8-4.

Acetic acid (20.5 mg, 341.76 μmol, 20 μL, 0.1 eq) and sodium triacetoxyborohydride (1.45 g, 6.84 mmol, 2 eq) were added sequentially to a solution of compound A-8-2 (1 g, 3.42 mmol, 1 eq) and compound A-1-6 (1.23 g, 3.76 mmol, 1.1 eq) in dichloromethane (20 mL) and methanol (4 mL). The reaction was stirred at 15° C. for 16 hours. After the reaction was completed, the reaction was concentrated under reduced pressure. The residue was diluted with water (20 mL), and extracted with dichloromethane (15 mL×2). The organic phases were combined and washed with saturated brine (15 mL), dried over anhydrous sodium sulfate, filtered, and concentrated under reduced pressure to obtain a crude product. The crude product was purified by column chromatography (dichloromethane/ethyl acetate=10/1) to obtain compound A-8-3 (Rf=0.1) ($^1$H NMR (400 MHz, CDCl$_3$) δ=7.19-7.18 (m, 1H), 7.15 (br dd, J=2.4, 8.4 Hz, 2H), 6.87 (br s, 2H), 6.50 (d, J=8.4 Hz, 1H), 4.70 (br t, J=6.8 Hz, 1H), 4.43-4.33 (m, 1H), 4.22-4.12 (m, 2H), 4.08-4.02 (m, 1H), 3.74-3.65 (m, 1H), 3.06-2.99 (m, 1H), 2.84-2.71 (m, 2H), 2.62-2.50 (m, 2H), 2.38 (br d, J=12.8 Hz, 1H), 2.25-2.17 (m, 1H), 2.11 (s, 3H), 1.67-1.53 (m, 1H), 1.45-1.37 (m, 1H), 1.19 (s, 9H)) and compound A-8-4 (Rf=0.4) ($^1$H NMR (400 MHz, CDCl$_3$) δ=7.19 (br d, J=2.4 Hz, 1H), 7.17-7.13 (m, 1H), 7.19-7.12 (m, 1H), 6.89-6.85 (m, 2H), 6.51 (d, J=8.8 Hz, 1H), 4.70 (br t, J=6.8 Hz, 1H), 4.44-4.33 (m, 1H), 4.24-4.18 (m, 1H), 4.14 (td, J=2.4, 8.8 Hz, 1H), 3.70-3.63 (m, 1H), 3.30 (br t, J=10.8 Hz, 1H), 3.07-3.00 (m, 1H), 2.85-2.71 (m, 2H), 2.55 (br d, J=11.6 Hz, 2H), 2.39 (br d, J=13.8 Hz, 1H), 2.25-2.16 (m, 1H), 2.11 (s, 3H), 1.60 (br s, 1H), 1.43 (br d, J=11.2 Hz, 1H), 1.19 (s, 9H)) respectively.

Step 4: Synthesis of Compound A-8.

Compound A-8-4 (600 mg, 1.06 mmol, 1 eq), bis(pinacolato)diboron (403 mg, 1.59 mmol, 1.5 eq), potassium acetate (156 mg, 1.59 mmol, 1.5 eq) and [1,1-bis(diphenylphosphorus)ferrocene]palladium dichloride (173 mg, 0.211 mmol, 0.2 eq) were added to anhydrous dioxane (10 mL), and the mixture was reacted at 80° C. for 18 hours under protection of nitrogen. After the reaction was completed, the mixture was filtered. The filtrate was diluted with water (15 mL) and then extracted with dichloromethane (20 mL×2). The organic phases were combined and washed with saturated brine (20 mL), dried over anhydrous sodium sulfate, filtered, and concentrated under reduced pressure to obtain a crude product. The crude product was purified by column chromatography to obtain compound A-8. $^1$H NMR (400 MHz, CDCl$_3$) δ=7.56-7.52 (m, 2H), 7.13 (br s, 1H), 6.87 (br s, 2H), 6.63 (d, J=8.4 Hz, 1H), 4.79 (br t, J=6.8 Hz, 1H), 4.40 (br d, J=9.2 Hz, 1H), 4.25-4.09 (m, 1H), 4.05 (q, J=7.2 Hz, 2H), 4.08-4.02 (m, 1H), 3.29 (br t, J=10.8 Hz, 1H), 3.06-3.00 (m, 1H), 2.83-2.74 (m, 2H), 2.60-2.51 (m, 2H), 2.38 (br d, J=13.3 Hz, 1H), 2.42-2.34 (m, 1H), 2.27-2.20 (m, 1H), 2.13 (s, 3H), 1.26 (s, 12H), 1.19 (s, 9H).

Step 5: Synthesis of Compound A-9.

Compound A-8-3 (300 mg, 528.67 μmol, 1 eq), bis(pinacolato)diboron (201.4 mg, 793.01 μmol, 1.5 eq) were dissolved in anhydrous DMF (5 mL), and potassium acetate (77.8 mg, 793.01 μmol, 1.5 eq), [1,1-bis(diphenylphosphino)ferrocene]palladium(II)dichloride dichloromethane adduct (86.4 mg, 105.73 umol, 0.2 eq) were added sequentially under protection of nitrogen. The reaction was stirred at 90° C. for 16 hours under protection of nitrogen. After the reaction was completed, the reaction was diluted with water (15 mL), and the mixture was extracted with ethyl acetate (20 mL×2). The organic phases were combined and washed with saturated brine (20 mL), dried over anhydrous sodium sulfate and concentrated under reduced pressure to obtain a crude product. The crude product was purified by column chromatography to obtain compound A-9. (MS:615.5[M+1]$^+$)

Reference Example 6: Fragment B-1

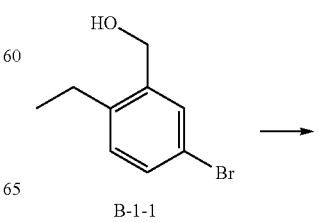

B-1-1

-continued

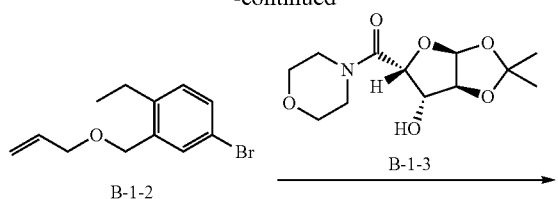

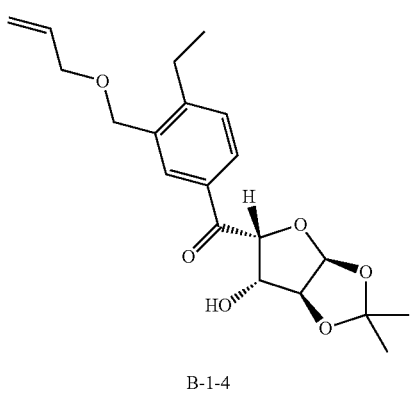

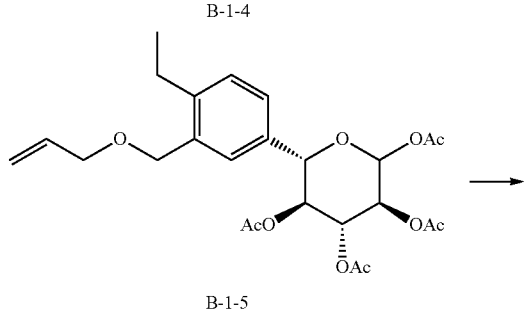

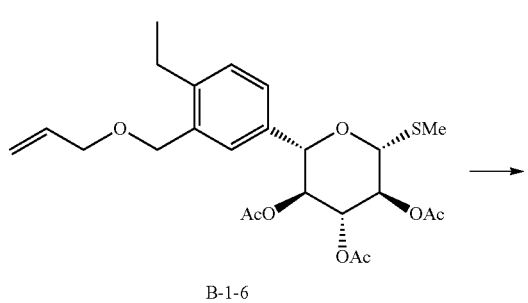

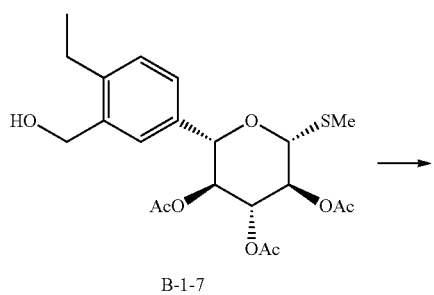

-continued

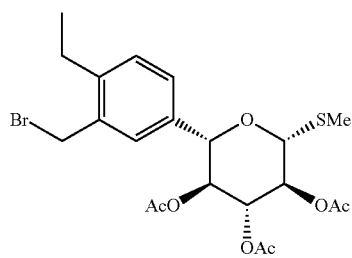

Synthetic Route:

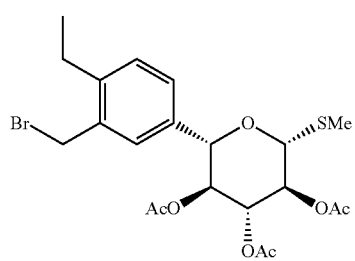

Step 1: Synthesis of Compound B-1-2.

Toluene (1200 mL), compound B-1-1 (200 g, 929.86 mmol, 1 eq), and tetrabutylammonium bromide (20.00 g, 62.04 mmol, 6.67% eq) were added sequentially to a solution of sodium hydroxide (200.00 g, 5.00 mol, 5.38 eq) in water (400 mL) and the mixture was stirred for 0.5 hour. Allyl bromide (157.49 g, 1.30 mol, 112.49 mL, 1.4 eq) was slowly added to the mixture. The reaction temperature was raised to 45-50° C. and stirred for 15 hours. After the reaction was completed, the reaction was cooled and the mixture was left to stand and layered. The aqueous phase was separated and extracted with toluene (300 mL). The organic phases were combined, washed with saturated brine (300 mL×3), and concentrated under reduced pressure. The residue was concentrated under reduced pressure twice with toluene (200 mL) to obtain compound B-1-2. $^1$H NMR (CDCl$_3$) δ 7.52 (d, J=2.0 Hz, 1H), 7.37 (dd, J=2.4, 8.4 Hz, 1H), 7.08 (d, J=8.4 Hz, 1H), 6.05-5.87 (m, 1H), 5.42-5.17 (m, 2H), 4.57-4.43 (m, 2H), 4.06 (d, J=5.6 Hz, 2H), 2.72-2.57 (m, 2H), 1.21 (t, J=7.6 Hz, 3H).

Step 2: Synthesis of Compound B-1-4.

A solution of n-butyllithium (2.5M, 4.31 mL, 1.1 eq) was added to a solution of compound B-1-2 (2.5 g, 9.80 mmol, 1 eq) in anhydrous tetrahydrofuran (40 mL) at −78° C. under protection of nitrogen, and the mixture was stirred for 0.5 hours to obtain solution A. A solution of Tert-butyl magnesium chloride (LM, 12.74) mL, 1.3 eq) was added to a solution of compound B-1-3 (3.21 g, 11.76 mmol, 1.2 eq) in anhydrous tetrahydrofuran (30 mL) at 0° C. under protection of nitrogen, and the mixture was stirred for 0.5 hours to obtain solution B. Solution B was added to solution A at −78° C., and the mixture was stirred and reacted at −78° C. for 0.5 hour. The reaction temperature was raised to 25° C. and stirred for 2 hours. After the reaction was completed, the reaction solution was slowly added to a saturated aqueous solution of ammonium chloride solution (5 mL) to quench the reaction, followed by addition of saturated brine (5 mL). The organic phase was separated after standing. The aqueous phase was extracted with ethyl acetate (10 mL×3). The organic phases were combined, dried over anhydrous sodium sulfate and concentrated under reduced pressure to obtain a crude product. The crude product was added with n-heptane (10 mL) and stirred for 1 hour and filtered, and the filter cake was collected to obtain compound B-1-4. MS:363.2[M+1]$^+$ Step 3: Synthesis of Compound B-1-5.

Cerium trichloride heptahydrate (3.39 g, 9.11 mmol, 865.45 µL, 1 eq) was added to a solution of compound B-1-4 (3.3 g, 9.11 mmol, 1 eq) in methanol (50 mL). Sodium borohydride (1.38 g, 36.42 mmol, 4 eq) was added to the reaction at 0° C. and stirred for 0.5 hour. The reaction temperature was raised to 25° C. and stirred for 1.5 hours. After the reaction was completed, saturated aqueous solution of ammonium chloride (10 mL) was added to the reaction at 0° C., and the mixture was stirred for 1 hour and concentrated under reduced pressure. The residue was added with ethyl acetate (30 mL), water (3 mL), and anhydrous magnesium sulfate (3 g), and the mixture was stirred for 0.5 hours and filtered. The filtrate was collected, and the filter cake was extracted with ethyl acetate (15 mL×3). The organic phases were combined, washed with water (10 mL×2) and saturated brine (10 mL×2) sequentially, dried over anhydrous sodium sulfate, filtered, and concentrated under reduced pressure to obtain a crude product. 2.8 g of the crude product was dissolved in acetic acid (14 mL) and water (14 mL), and the reaction was heated to 95-100° C. and stirred for 16 hours. After the reaction was completed, the reaction was concentrated under reduced pressure. The residue was added with toluene (10 mL) and concentrated under reduced pressure. After repeating twice, a crude product was obtained. 2.5 g of the crude product was dissolved in pyridine (12 mL), and acetic anhydride (6.29 g, 61.66 mmol, 5.77 mL, 8 eq) was added at 0° C. The reaction was stirred at 10-20° C. for 16 hours. After the reaction was completed, water (5 mL) was added to the reaction to quench the reaction in ice bath. The mixture was concentrated under reduced pressure. The residue was added with 1M aqueous hydrochloric acid (5 mL) to neutralize the remaining pyridine, and extracted with ethyl acetate (30 mL×2). The organic phases were combined and washed with saturated brine (25 mL) and dried over anhydrous sodium sulfate, filtered and concentrated under reduced pressure to obtain crude product. The crude product was purified by column chromatography to obtain compound B-1-5. $^1$H NMR (CDCl$_3$) δ 7.33 (s, 1H), 7.30-7.20 (m, 1H), 7.20-7.15 (m, 1H), 6.05-5.90 (m, 1H), 5.40-5.05 (m, 5H), 4.65-4.55 (m, 1H), 4.52 (s, 2H), 4.13 (q, J=7.2 Hz, 1H), 4.05-4.00 (m, 2H), 2.66 (q, J=7.6 Hz, 2H), 2.15-1.95 (m, 9H), 1.83 (d, J=12.4 Hz, 3H), 1.19 (t, J=7.2 Hz, 3H).

Step 4: Synthesis of Compound B-1-6.

Compound B-1-5 (1.4 g, 2.84 mmol, 1 eq), thiourea (757.32 mg, 9.95 mmol, 3.5 eq) were dissolved in dioxane (14 mL), and trimethylsilyl trifluoromethanesulfonate (2.53 g, 11.37 mmol, 2.05 mL, 4 eq) was added slowly to the reaction at 25° C. The reaction was heated to 60° C. and stirred for 1.5 hours. The reaction was cooled to 0° C. Diisopropylethylamine (2.94 g, 22.74 mmol, 3.96 mL, 8 eq) and methyl iodide (2.02 g, 14.21 mmol, 884.80 µL, 5 eq) were added to the reaction. The reaction was heated to 25° C. and stirred for 17 hours. After the reaction was completed, water (10 mL) was added to quench the reaction, and the mixture was extracted with ethyl acetate (15 mL×2). The organic phases were combined, dried with anhydrous sodium sulfate and filtered, and the filtrate was concentrated under reduced pressure to obtain a crude product. The crude product was purified by column chromatography to obtain compound B-1-6. MS:503.1[M+23]$^+$ Step 5: Synthesis of Compound B-1-7.

A mixture of compound B-1-6 (9.48 g, 19.73 mmol, 1 eq), barbituric acid (5.05 g, 39.45 mmol, 2 eq), and tetrakistriphenylphosphine palladium (2.28 g, 1.97 mmol, 0.1 eq) in ethanol (95 mL) was heated to 65° C. and stirred for 16 hours under the protection of nitrogen. After the reaction was completed, the reaction was quenched by water (100 mL). The mixture was concentrated under reduced pressure. The residue was extracted with ethyl acetate (100 mL×3). The organic phases were combined, dried with anhydrous sodium sulfate and filtered, and the filtrate was concentrated under reduced pressure to obtain the crude product. The crude product was purified by column chromatography to obtain compound B-1-7. MS: 463.2 [M+23]$^+$ Step 6: Synthesis of Compound B-1.

Phosphorus tribromide (4.40 g, 16.27 mmol, 1.54 mL, 0.5 eq) was added dropwise to a solution of compound B-1-7 (14.33 g, 32.53 mmol, 1 eq) in anhydrous tetrahydrofuran (145 mL) at 0° C. under the protection of nitrogen. The reaction was stirred at 20° C. for 16 hours. After the reaction was completed, 2M potassium carbonate aqueous solution (75 mL) was added dropwise to the mixture to quench the reaction at 0° C., and after stirring for 10 minutes, the mixture was left to stand and layered. The organic phase was separated and the aqueous phase was extracted with ethyl acetate (200 mL). The organic phases were combined, washed with saturated brine (100 mL), dried over anhydrous sodium sulfate and filtered. The filtrate was concentrated under reduced pressure to obtain a crude product. Methyl tert-butyl ether (40 mL) and n-hexane (60 mL) were added to the crude product, and the mixture was stirred at 25° C. for 16 hours and then filtered. The filter cake was washed with a mixed solvent (methyl tert-butyl ether:n-hexane=2:3, 50 mL) and dried to obtain compound B-1 (15 g, 27.10 mmol, 1 eq) $^1$H NMR (CDCl$_3$-d) δ 7.32-7.28 (m, 1H), 7.28-7.23 (m, 1H), 7.23-7.18 (m, 1H), 5.41-5.29 (m, 1H), 5.22 (t, J=10.0 Hz, 1H), 5.11 (t, J=10.0 Hz, 1H), 4.59-4.47 (m, 3H), 4.43 (br d, J=9.6 Hz, 1H), 2.75 (q, J=7.2 Hz, 2H), 2.20 (s, 3H), 2.10 (s, 3H), 2.02 (s, 3H), 1.84 (s, 3H), 1.27 (t, J=7.6 Hz, 3H).

Referring to the synthesis method of steps 1 to 6 in Reference Example 6, the fragments B-2, B-3, and B-4 in Table 1 were synthesized.

TABLE 1
Reference Examples 2-4
| Reference Example | Fragment | Structure | Confirmation |
|---|---|---|---|
| 2 | B-2 | 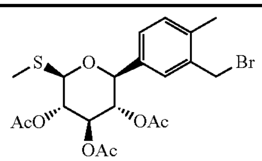 | $^1$H NMR (400 MHz, CDCl$_3$) δ 7.26–7.22 (m, 2 H), 7.19–7.15 (m, 1 H), 5.34 (q, J = 9.9 Hz, 1 H), 5.22 (t, J = 9.5 Hz, 1 H), 5.10 (t, J = 9.7 Hz, 1 H), 4.55 (d, J = 9.8 Hz, 1 H), 4.53–4.45 (m, 2 H), 4.42 (d, J = 9.8 Hz, 1 H), 2.39 (s, 3 H), 2.21 (s, 3 H), 2.10 (s, 3 H), 2.02 (s, 3 H), 1.84 (s, 3 H). |
| 3 | B-3 | 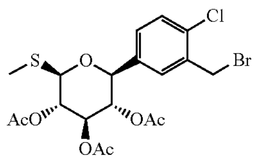 [SMILES: CS[C@H]1O[C@@H](c2ccc(Cl)c(CBr)c2)[C@H](OC(C)=O)[C@@H](OC(C)=O)[C@@H]1OC(C)=O] | $^1$H NMR (400 MHz, CDCl$_3$) δ 7.43–7.36 (m, 2 H), 7.29 (dd, J = 8.3, 2.0 Hz, 1 H) 5.44–5.33 (m, 1 H), 5.28–5.17 (m, 1 H), 5.07 (t, J = 9.7 Hz, 1 H), 4.66–4.49 (m, 3 H), 4.44 (d, J = 10.0 Hz, 1 H), 2.21 (s, 3 H), 2.11 (s, 3 H), 2.02 (s, 3 H), 1.87 (s, 3 H). |
| 4 | B-4 | 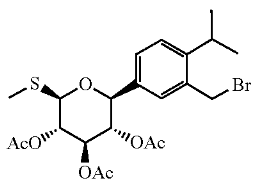 | MS: 540.8 [M + 23]$^+$ |
Example 1: WXD001
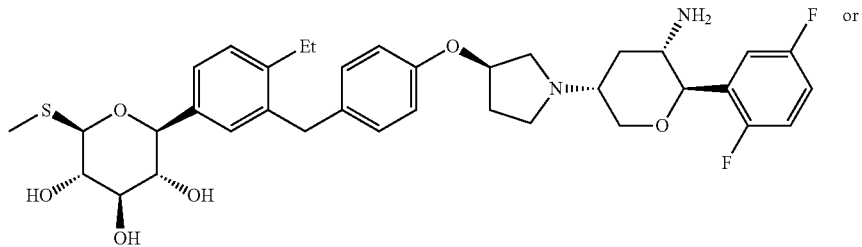
or
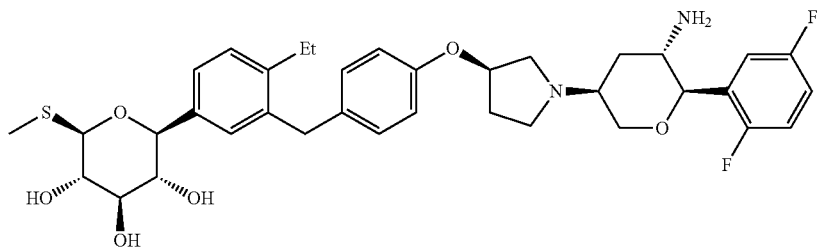
Synthetic Route:
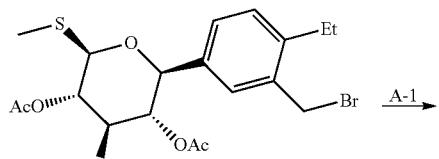
A-1

-continued
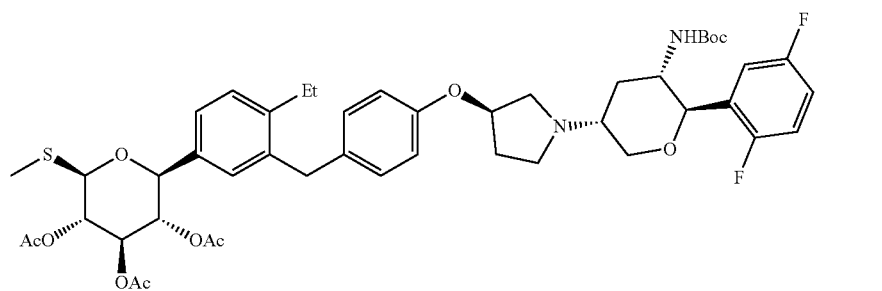
or
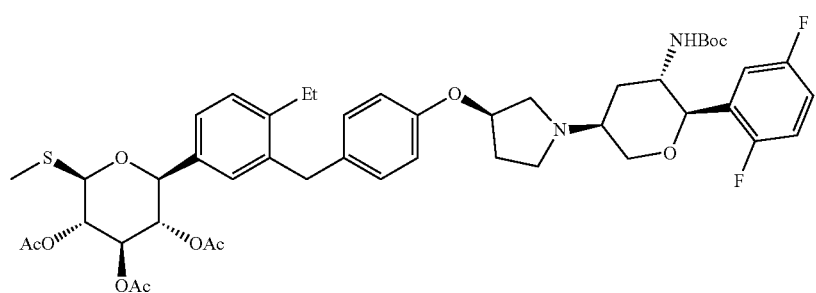
WXD001-1
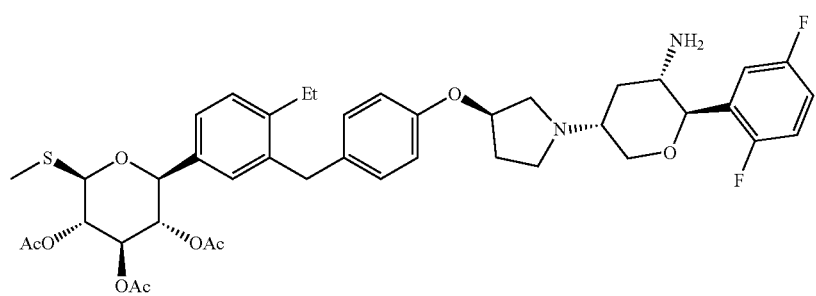
or
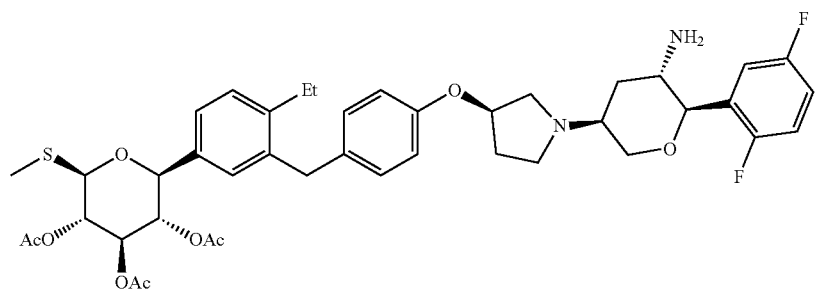
WXD001-2

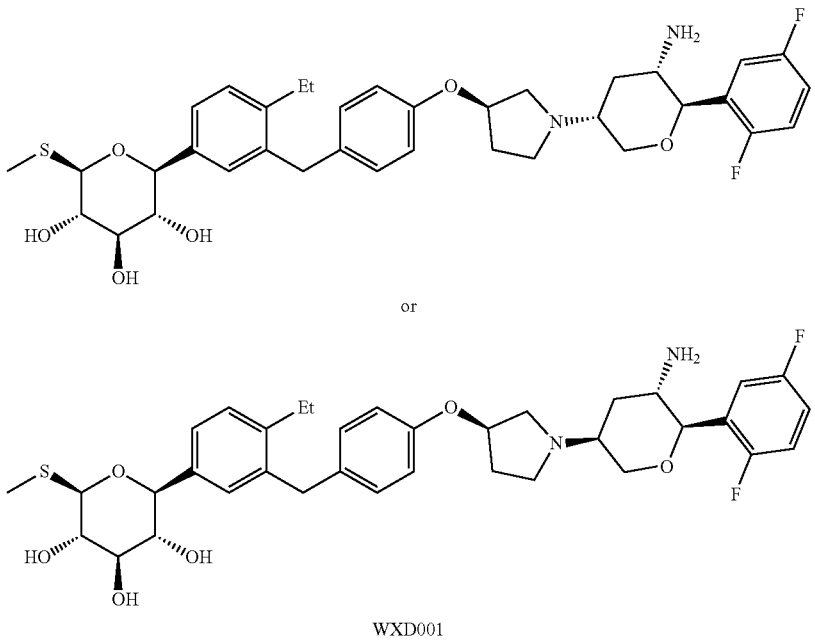

WXD001

Step 1: Synthesis of Compound WXD001-1

Compound A-1 (3 g, 5.96 mmol, 1 eq), compound B-1 (4.29 g, 7.15 mmol, 1.2 eq), sodium carbonate (1.26 g, 11.92 mmol, 2 eq) and tetrakistriphenylphosphonium palladium (1.38 g, 1.19 mmol, 0.2 eq) were suspended in a mixed solvent of toluene (86 mL), ethanol (21.5 mL) and water (21.5 mL). The reaction was stirred at 50° C. for 16 hours under protection of nitrogen. After the reaction was completed, the reaction was concentrated under reduced pressure, and the residue was diluted with dichloromethane (200 mL) and washed with water (100 mL×3). The organic phase was dried over anhydrous sodium sulfate and concentrated under reduced pressure to obtain a crude product. Ethanol (80 mL) was added to the crude product and stirred for 30 minutes and then filtered. The filter cake was washed with ethanol (10 mL×3) and dried to obtain compound WXD001-1.

Step 2: Synthesis of Compound WXD001-2

Compound WXD001-1 (3.3 g, 3.68 mmol, 1 eq) was dissolved in ethyl acetate (66 mL), and added with a solution of hydrogen chloride in ethyl acetate (4M, 66.00 mL, 71.76 eq). The reaction was stirred at 15° C. for 16 hours. After the reaction was completed, the reaction was concentrated under reduced pressure to obtain compound WXD001-2.

Step 3: Synthesis of Compound WXD001

Lithium hydroxide monohydrate (1.02 g, 24.39 mmol, 27 eq) and water (6 mL) were added to a mixture of compound WXD001-2 (760 mg, 0.91 mmol, 1 eq), methanol (6 mL) and tetrahydrofuran (3 mL). The mixture was stirred at 25° C. for 16 hours. After the reaction was completed, the reaction was diluted with water (10 mL) and extracted with ethyl acetate (10 mL×3). The organic phases were combined and washed with saturated brine (30 mL), dried over anhydrous sodium sulfate and filtered. The filtrate was concentrated under reduced pressure to obtain a crude product. The crude product was purified by preparative high performance liquid chromatography to obtain the target compound WXD001. $^1$H NMR (400 MHz, CDCl$_3$) δ 7.21 (s, 2H), 7.17-7.11 (m, 1H), 7.08-6.94 (m, 5H), 6.77 (d, J=8.8 Hz, 2H), 4.87-4.79 (m, 1H), 4.37 (d, J=9.6 Hz, 1H), 4.25-4.09 (m, 3H), 3.95 (s, 2H), 3.68-3.61 (m, 1H), 3.55-3.46 (m, 2H), 3.37 (br t, J=10.0 Hz, 1H), 3.10 (br dd, J=10.0 Hz, J=6.0 Hz, 1H), 2.88 (q, J=7.6 Hz, 1H), 2.75 (br d, J=7.6 Hz, 2H), 2.69-2.51 (m, 4H), 2.40 (br d, J=11.6 Hz, 1H), 2.27 (br dd, J=14.0 Hz, J=7.2 Hz, 1H), 2.18 (s, 3H), 2.07-1.95 (m, 1H), 1.42 (q, J=12.0 Hz, 1H), 1.15 (t, J=7.6 Hz, 3H).

Referring to the synthesis method of steps 1 to 3 in Example 1, each of Examples 2-12 in Table 2 below was synthesized. The structures in Table 2 also represent possible isomers.

TABLE 2
Each isomer of Examples 2-12
| Examples | Fragment A | Fragment B | Compound | Structure |
|---|---|---|---|---|
| 2 | A-2 | 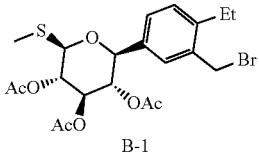 B-1 | WXD002 | 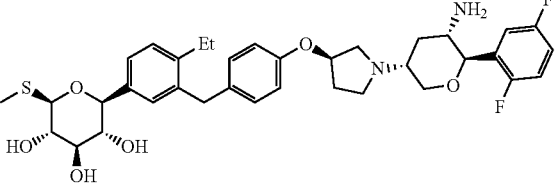 or |
| 3 | A-1 | 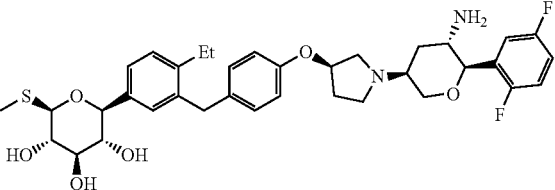 B-2 | WXD003 | 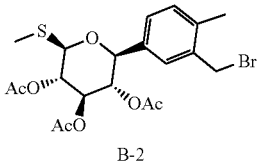 or 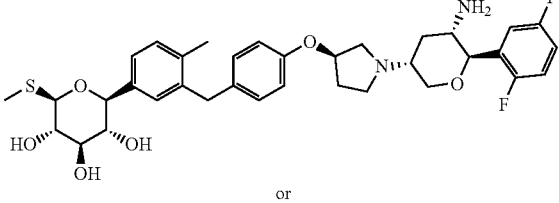 |
| 4 | A-1 | 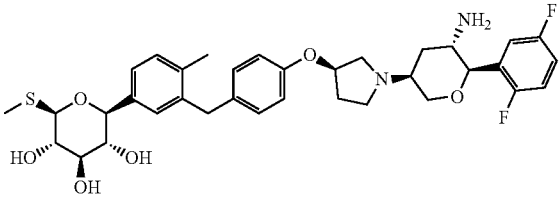 B-3 | WXD004 | 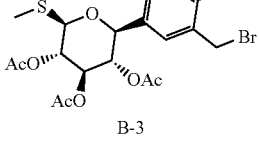 or 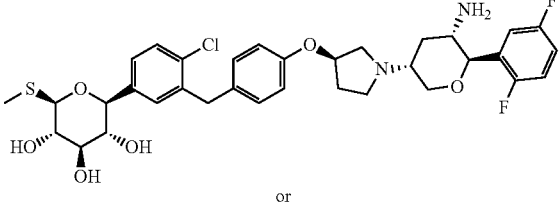 |

TABLE 2-continued

Each isomer of Examples 2-12

| Examples | Fragment A | Fragment B | Compound | Structure |
|---|---|---|---|---|
| 5 | A-3 | B-3 | WXD005 | |
| 6 | A-4 | B-3 | WXD006 | |
| 7 | A-5 | B-1 | WXD007 | 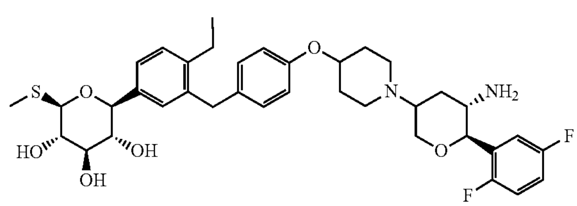 [SMILES: CCc1ccc([C@@H]2O[C@H](SC)[C@@H](O)[C@H](O)[C@H]2O)cc1Cc1ccc(OC2CCN(C3CO[C@H](c4cc(F)ccc4F)[C@@H](N)C3)CC2)cc1] |
| 8 | A-6 | B-1 | WXD008 | |

TABLE 2-continued
Each isomer of Examples 2-12
| Examples | Fragment A | Fragment B | Compound | Structure |
|---|---|---|---|---|
| 9 | A-7 | 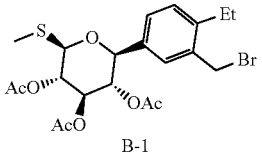 B-1 | WXD009 | 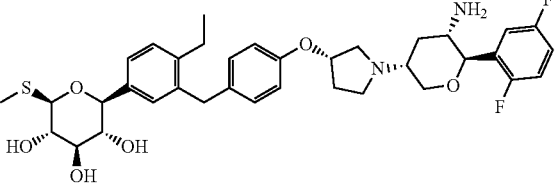 or |
| 10 | A-8 | 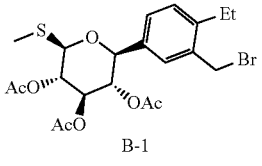 B-1 | WXD010 | 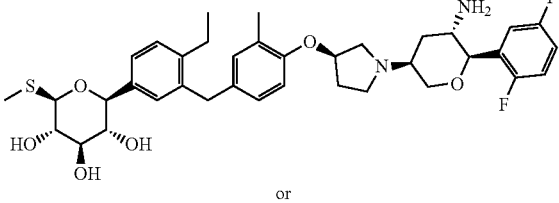 or |
| 11 | A-9 | 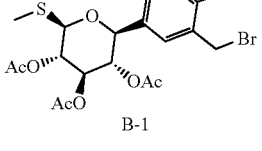 B-1 | WXD011 | 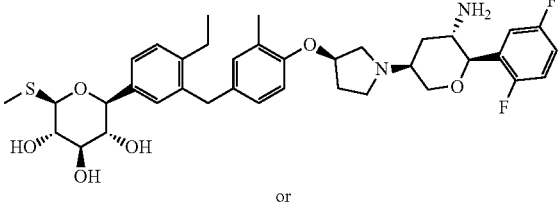 or 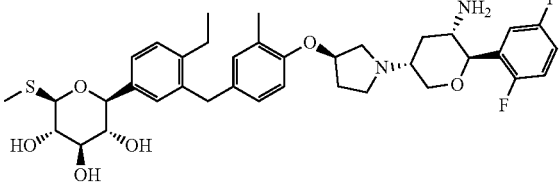 |

TABLE 2-continued

Each isomer of Examples 2-12

| Examples | Fragment A | Fragment B | Compound | Structure |
|---|---|---|---|---|
| 12 | A-1 | B-4 | WXD012 | |

The hydrogen spectrum and mass spectrum data of each example are shown in Table 3.

TABLE 3

Proton spectrum and mass spectrum data of each example

| Example | Compound | $^1$H NMR | MS m/z |
|---|---|---|---|
| 1 | WXD001 | $^1$H NMR (400 MHz, CDCl$_3$) δ 7.21 (s, 2H), 7.17-7.11 (m, 1H), 7.08-6.94 (m, 5H), 6.77 (d, J = 8.8 Hz, 2H), 4.87-4.79 (m, 1H), 4.37 (d, J = 9.6 Hz, 1H), 4.25-4.09 (m, 3H), 3.95 (s, 2H), 3.68-3.61 (m, 1H), 3.55-3.46 (m, 2H), 3.37 (br t, J = 10.0 Hz, 1H) 3.10 (br dd, J = 10.0 Hz, J = 6.0 Hz, 1H), 2.88 (q, J = 7.6 Hz, 1H), 2.75 (br d, J = 7.6 Hz, 2H), 2.69-2.51 (m, 4H), 2.40 (br d, J = 11.6 Hz, 1H), 2.27 (br dd, J = 14.0 Hz, J = 7.2 Hz, 1H), 2.18 (s, 3H), 2.07-1.95 (m, 1H), 1.42 (q, J = 12.0 Hz, 1H), 1.15 (t, J = 7.6 Hz, 3H). | 671.1 [M + 1]$^+$ |
| 2 | WXD002 | $^1$H NMR (400 MHz,CD$_3$OD) δ 1.09 (br s, 3H), 1.66 (br s, 1H), 2.04 (br s, 1H), 2.14 (br s, 3H), 2.36 (br d, J = 12.55 Hz, 2H), 2.45 (br s, 1H), 2.61 (br d, J = 7.03 Hz, 2H), 2.72 (br s, 1H), 2.86 (br d, J = 10.29 Hz, 1H), 2.93 (br s, 1H), 3.16 (br s, 2H), 3.37-3.50 (m, 3H), 3.62 (br d, J = 11.54 Hz, 1H), 3.96 (br s, 2H), 4.06-4.25 (m, 2H), 4.37 (br t, J = 11.17 Hz, 2H), 6.79 (br d, J = 7.78 Hz, 2H), 7.03-7.23 (m, 7H), 7.50 (br s, 1H). | 671.3 [M + 1]$^+$ |
| 3 | WXD003 | $^1$H NMR (400 MHz, CDCl$_3$) δ 7.17 (s, 2H), 7.15-7.11 (m, 1H), 7.08-6.94 (m, 5H), 6.78 (br d, J = 8.0 Hz, 2H), 4.84 (br s, 1H), 4.38 (br d, J = 9.6 Hz, 1H), 4.25-4.12 (m, 3H), 3.92 (s, 2H), 3.70-3.66 (t, J = 8.8 Hz, 1H), 3.51 (dd, J = 15.6 Hz, J = 8.8 Hz, 2H), 3.38 (t, J = 10.8 Hz, 1H), 3.12 (dd, J = 10.0 Hz, J = 6.0 Hz, 1H), 2.93-2.85 (m, 1H), 2.81-2.73 (m, 2H), 2.72-2.64 (m, 1H), 2.63-2.53 (br s, 1H), 2.40 (br d, J = 11.6 Hz, 1H), 2.33-2.28 (m, 1H), 2.27 (s, 3H), 2.19 (s, 3H), 2.03-2.00 (m, 1H), 1.44 (q, J = 12.0 Hz, 1H), | 657.1 [M + 1]$^+$ |
| 4 | WXD004 | $^1$H NMR (400 MHz, DMSO-d$_6$) δ 8.20 (s, 2H), 7.38 (d, J = 8.4 Hz, 1H), 7.28 (s, 1H), 7.27-7.18 (m, 4H), 7.10 (br d, J = 8.8 Hz, 2H), 6.80 (br d, J = 8.5 Hz, 2H), 4.587-4.76 (m, 1H), 4.34 (br d, J = 9.6 Hz, 1H), 4.19 (br d, J = 9.6 Hz, 1H), 4.09 (br d, J = 9.6 Hz, 1H), 4.06-4.03 (m, 1H), 3.98 (br s, 2H), 3.27 (br d, J = 8.4 Hz, 1H), 3.18 (dt, J = 18.0, 9.2 Hz, 4H), 3.00-2.88 (m, 3H), 2.82-2.75 (m, 1H), 2.68 (br d, J = 8.0 Hz, 1H), 2.35-2.17 (m, 2H), 2.03 (s, 3H), 1.78-1.69 (m, 1H), 1.39 (q, J = 11.6 Hz, 1H). | 677.2 [M + 1]$^+$ |
| 5 | WXD005 | $^1$H NMR (400 MHz, CD$_3$OD) δ 7.36 (d, J = 8.0 Hz, 1H), 7.31-7.23 (m, 3H), 7.22-7.16 (m, 2H), 7.13 (br d, J = 8.3 Hz, 2H), 6.74 (br d, J = 8.3 Hz, 2H), 4.87-4.80 (m, 1H), 4.51 (br d, J = 8.5 Hz, 1H), 4.39 (d, J = 9.5 Hz, 1H), 4.14 (d, J = 9.5 Hz, 1H), 4.01-4.11 (m, 3H), 3.87 (m, 2H), 3.42-3.48 (m, 1H), 3.40-3.32 (m, 4H), 3.24 (br t, J = 10.8 Hz, 1H), 2.77 (m, 1H), 2.37 (m, 1H), 2.13 (s, 3H), 1.44 (m, 1H). | 663.1 [M + 1]$^+$ |
| 6 | WXD006 | $^1$H NMR (400 MHz, CDCl$_3$) δ 7.64-7.51 (m, 1H), 7.40 (br d, J = 7.5 Hz, 1H), 7.34-7.26(m, 2H), 7.25-7.12 (m, 4H), 6.81 (br d, J = 8.3 Hz, 2H), 4.64 (br d, J = 9.8 Hz, 1H), 4.43 (br d, J = 9.5 Hz, 1H), 4.18 (br d, J = 9.8 Hz, 1H), 4.06 (m, 5H), 3.71 (br d, J = 12.3 Hz, 1H), 3.57 (m, 1H), 3.53-3.46 (m, 1H), 3.44-3.37 (m, 3H), | 663.1 [M + 1]$^+$ |

TABLE 3-continued

Proton spectrum and mass spectrum data of each example

| Example | Compound | ¹H NMR | MS m/z |
|---|---|---|---|
| | | 2.81 (br s, 1H), 2.85-2.76 (m, 1H), 2.32 (br d, J = 11.8 Hz, 1H), 2.17 (s, 3H), 1.99-1.85 (m, 1H). | |
| 7 | WXD007 | ¹H NMR (400 MHz, CD₃OD) δ 7.32-7.25 (m, 1H), 7.24-7.13 (m, 5H), 7.05 (d, J = 8.5 Hz, 2H), 6.83 (d, J = 8.5 Hz, 2H), 4.48 (d, J = 9.8 Hz, 1H), 4.39 (d, J = 9.5 Hz, 2H), 4.26 (br d, J = 8.3 Hz, 1H), 4.13 (d, J = 9.0 Hz, 1H), 3.97 (s, 2H), 3.55 (t, J = 10.9 Hz, 1H), 3.50-3.34 (m, 4H), 2.96 (m, 3H), 2.73-2.56 (m, 4H), 2.49 (br d, J = 12.8 Hz, 1H), 2.14 (s, 3H), 2.02 (m, 2H), 1.82 (m, 2H), 1.72 (q, J = 12.3 Hz, 1H), 1.09 (t, J = 7.5 Hz, 3H). | 685.3 [M + 1]⁺ |
| 8 | WXD008 | ¹H NMR (400 MHz, CD₃OD) δ 7.46 (m, 1H), 7.27-7.13 (m, 5H), 7.07 (d, J = 8.5 Hz, 2H), 6.82 (d, J = 8.5 Hz, 2H), 4.96 (m, 1H), 4.66 (br d, J = 8.8 Hz, 1H), 4.38 (d, J = 9.5 Hz, 1H), 4.25 (br d = 13.1 Hz, 1H), 4.12 (d, J = 9.0 Hz, 1H), 3.97 (s, 2H), 3.72 (m, 2H), 3.49-3.32 (m, 3H), 3.18 (m, 1H), 3.05 (br s, 2H), 2.85 (m, 1H), 2.69 (m, 1H), 2.61 (q, J = 7.5 Hz, 2H), 2.51 (br d, J = 10.3 Hz, 1H), 2.40 (dq, J = 13.8, 7.1 Hz, 1H), 2.14 (s, 3H), 2.10 (m, 1H), 1.96 (m, 1H), 1.09 (t, J = 7.5 Hz, 3H). | 671.3 [M + 1]⁺ |
| 9 | WXD009 | ¹H NMR CD₃OD) δ 7.34-7.11 (m, 8H), 6.90 (d, J = 8.4 Hz, 2H), 5.21 (br s, 1H), 4.71 (d, J = 10.0 Hz, 1H), 4.50 (br d, J = 6.0 Hz, 1H), 4.41 (d, J = 9.6 Hz, 1H), 4.15 (d, J = 9.2 Hz, 1H), 4.05-3.95 (m, 2H), 3.85-3.58 (m, 7H), 3.51-3.36 (m, 3H), 2.82 (br d, J = 9.6 Hz, 1H), 2.62 (q, J = 7.6 Hz, 2H), 2.49 (br s, 1H), 2.55-2.43 (m, 1H), 2.40-2.29 (m, 1H), 2.16 (s, 3H), 1.11 (t, J = 7.6 Hz, 3H). | 671.1 [M + 1]⁺ |
| 10 | WXD010 | ¹H NMR (400 MHz, DMSO) δ = 7.28-7.04 (m, 6), 6.95-6.82 (m, 2H), 6.95-6.81 (m, 1H), 5.30-5.05 (m, 2H), 4.92-4.73 (m, 2H), 4.32 (br d, J = 9.3 Hz, 1H), 4.12-3.99 (m, 3H), 3.86 (br s, 2H), 3.27-3.14 (m, 2H), 3.02-2.95 (m, 1H), 2.75 (br d, J = 8.0 Hz, 2), 2.66-2.51 (m, 6H), 2.42 (br s, 2H), 2.26-2.14 (m, 2H), 2.11-1.98 (m, 6H), 1.76 (br s, 1H), 1.41-1.21 (m, 2H), 1.06 (br t, J = 7.3 Hz, 4H). | 685.4 [M + 1]⁺ |
| 11 | WXD011 | ¹H NMR (400 MHz, CD₃OD) δ = 7.52-7.34 (m, 2H), 7.25-7.12 (m, 1H), 7.22-7.09 (m, 3H), 6.97-6.85 (m, 2H), 6.76 (d, J = 8.4 Hz, 1H), 4.94 (br d, J = 6.8 Hz, 2H), 4.49 (d, J = 9.6 Hz, 1H), 4.40 (d, J = 9.6 Hz, 1H), 4.23 (br d, J = 12.8 Hz, 1H), 4.16-4.11 (m, 1H), 3.94 (s, 2H), 3.68 (br d, J = 11.6 Hz, 1H), 3.54-3.36 (m, 5H), 3.24 (br dd, J = 6.0, 10.8 Hz, 1H), 3.00 (q, J = 7.2 Hz, 1H), 2.90 (br d, J = 10.4 Hz, 1H), 2.84-2.76 (m, 1H), 2.63 (q, J = 7.6 Hz, 2H), 2.55 (br s, 1H), 2.50-2.32 (m, 2H), 2.16 (s, 6H), 2.14-2.14 (m, 1H), 1.84-1.74 (m, 1H), 1.48 (br d, J = 6.4 Hz, 1H), 1.36-1.19 (m, 1H), 1.12 (t, J = 7.6 Hz, 3H). | 685.5 [M + 1]⁺ |
| 12 | WXD012 | ¹H NMR (400 MHz, CD₃OD) δ 7.29-7.13 (m, 6H) 7.04 (d, J = 8.5 Hz, 2H) 6.78 (d, J = 8.5 Hz, 2H) 4.62 (br s, 1H) 4.46 (d, J = 9.8 Hz, 1H) 4.40 (d, J = 9.5 Hz, 1H) 4.24 (br dd, J = 11.04, 2.8 Hz, 1H) 4.13 (d, J = 9.0 Hz, 1H) 3.99 (s, 2H) 3.52-3.34 (m, 4H) 3.28-3.10 (m, 2H) 3.07-2.91 (m, 3H) 2.75-2.58 (m, 2H) 2.49 (br d, J = 10.0 Hz, 1H) 2.37-2.26 (m, 1H) 2.15 (s, 3H) 2.06-1.87 (m, 1H) 1.64 (q, J = 11.8 Hz, 1H) 1.09 (dd, J = 6.78, 3.0 Hz, 6H). | 685.3 [M + 1]⁺ |

Example 1. Cell Activity Test In Vitro

Experimental Steps and Methods:

Biological activity experiment 1: SGLT1 glucose transport test

1. Experimental Purpose:

The effect of the compound on the glucose transport activity of the SGLT1 transporter was detected through measuring the amount of [$^{14}$C]-labeled glucose entering the cells with high expression of Human-SGLT1.

2. Experimental Method 2.1. Cell Preparation

The cells stably expressing Human-SGLT1 used in the experiment were constructed by Shanghai WuXi AppTec. The SGLT1 cells were plated on a Cytostar-T (PerkinElmer) 96-well cell culture plate, and cultured overnight at 5% $CO_2$ at 37° C.

2.2. SGLT1 Glucose Transport Test

1) Experimental buffer: 10 mM 4-hydroxyethylpiperazine ethanesulfonic acid (HEPES), 1.2 mM magnesium chloride ($MgCl_2$), 4.7 mM potassium chloride (KCl), 2.2 mM calcium chloride ($CaCl_2$) and 120 mM sodium chloride (NaCl).

2) The compound was diluted with 100% dimethyl sulfoxide (DMSO) with 1 mM as the starting concentration and 8 points of 5-fold serial dilutions.

3) 3 μM [$^{14}$C]-labeled methyl α-D-glucopyranoside was prepared with experimental buffer.

4) The cells were treated with 49 μL of experimental buffer, 1 μL of the compound which was gradient diluted, and 50 μL of 3 μM [$^{14}$C] isotope-labeled sugar solution at 37° C. for 2 hours.

5) The isotope detector (Micro beta Reader) was used to read.

6) The data was calculated by GraphPad Prism 5.0 software: log(inhibitor) vs. response—Variable slope to obtain the $IC_{50}$ value of the test compound. The experimental results were shown in Table 3.

Biological activity experiment 2: SGLT2 glucose transport test

1. Experimental Purpose:

The effect of the compound on the glucose transport activity of the SGLT2 transporter was detected through measuring the amount of [$^{14}$C]-labeled glucose entering the cells with high expression of Human-SGLT2.

2. Experimental Method 2.1. Cell Preparation

The cells stably expressing Human-SGLT2 used in the experiment were constructed by Shanghai WuXi AppTec. The SGLT2 cells were plated on a 96-well cell culture plate (Greiner) and cultured overnight at 5% $CO_2$ at 37° C.

2.2. SGLT2 Glucose Transport Test

1) Experimental buffer: 10 mM 4-hydroxyethylpiperazine ethanesulfonic acid (HEPES), 1.2 mM magnesium chloride ($MgCl_2$), 4.7 mM potassium chloride (KCl), 2.2 mM calcium chloride ($CaCl_2$)) and 120 mM sodium chloride (NaCl).

2) Termination buffer: 10 mM 4-hydroxyethylpiperazine ethanesulfonic acid (HEPES), 1.2 mM magnesium chloride ($MgCl_2$), 4.7 mM potassium chloride (KCl), 2.2 mM calcium chloride ($CaCl_2$), 120 mM sodium chloride (NaCl) and 1 μM LX4211.

3) The compound was diluted with 100% dimethyl sulfoxide (DMSO) with a starting concentration of 10 μM and 8 points of 5-fold serial dilution.

4) 6 μM [$^{14}$C]-labeled methyl α-D-glucopyranoside was prepared with experimental buffer.

5) The cells were treated with 49 μL of experimental buffer, 1 μL of gradient diluted compound, and 50 μL of 6 μM [$^{14}$C]isotope-labeled sugar solution at 37° C. for 2 hours.

6) The liquid in the well was aspirated and the cells were rinsed 3 times with termination buffer.

7) The cells were lysed with 50 μL of 10% sodium hydroxide solution, the cell lysate was aspirated into the scintillation tube, and 2 mL of scintillation fluid was added.

8) An isotope detector (Tricarb) was used to read.

9) The data was calculated by GraphPad Prism 5.0 software: log(inhibitor) vs. response—Variable slope to obtain the $IC_{50}$ value of the test compound. The experimental results were shown in Table 3.

Biological activity experiment 3: rhDPP4 inhibitor screening experiment

1. Experimental Purpose:

The inhibitory activity of the compounds on recombinant human dipeptidyl peptidase 4 (rhDPP4) was evaluated by measuring the median inhibitory concentration ($IC_{50}$) value of the compounds. In this experiment, rhDPP4 was used to catalyze a substrate to produce luciferin, and reacted with luciferase to produce light signals, wherein the substrate is the luminescent precursor glycine-proline-aminofluorescein (Gly-Pro-aminoluciferin). The intensity of the light signal is directly proportional to the enzyme activity.

2. Experimental Method 1) 250 nL of gradient diluted compound (4 times dilution, 10 detection concentrations) was transferred to a 384-well plate (PerkingElmer-6007299) using a non-contact nano-upgraded acoustic pipetting system (ECHO). The concentration of dimethylsulfoxide (DMSO) concentration was 0.5% in the final reaction system. Blank control wells (containing DMSO, substrate and 10 mM of tris(hydroxymethyl)aminomethane hydrochlorid (Tris-HCl)) and positive control wells (containing DMSO, substrate and rhDPP4) were set.

2) The pre-packed frozen buffer containing luciferase was taken out and restored to room temperature, and then added with substrate to prepare a working solution with a substrate concentration of 20 μM. The rhDPP4 was prepared as a 0.2 ng/mL working solution with 10 mM Tris-HCl (pH8.0) aqueous solution.

3) 25 μL of working solution containing 20 μM substrate and 25 μL of working solution containing 0.2 ng/mL rhDPP4 were added to the 384-well plate with the compound added already. The plate was centrifuged at 1000 rpm for 30 s. The plate was sealed with aluminum foil sealing film and incubated at room temperature for 1 hour.

4) The light signal intensity was detected with a multi-function enzyme label detector EnVision. The raw data was used to calculate the inhibition activity of the compounds on rhDPP4.

Inhibitory activity %=100−(compound well signal value-blank control well signal value)/(positive control well signal value-blank control well signal value)*100; the inhibition percentage was imported into GraphPad Prism software for data processing to obtain the corresponding dose-effect curve and the $IC_{50}$ value of the test compound was obtained. The experimental results were shown in Table 4:

TABLE 4

In vitro cell viability test results

| Compound | Human-SGLT1 $IC_{50}$ (nM) | Human-SGLT2 $IC_{50}$ (nM) | rhDPP4 $IC_{50}$ (nM) |
|---|---|---|---|
| WXD001 | 3.46 | 2.0 | 34.88 |
| WXD002 | 1.22 | 0.76 | 4217 |
| WXD003 | 44.05 | 2.9 | 24.52 |
| WXD004 | 137.5 | 3.9 | 44.8 |
| WXD005 | 70.73 | 0.66 | 111.7 |
| WXD006 | 13.63 | 1.41 | NA |
| WXD007 | 3.37 | 1.44 | 510.5 |
| WXD008 | 8.13 | 1.21 | NA |
| WXD009 | 25.94 | 1.90 | 295.7 |
| WXD010 | 144.4 | 21.17 | 164.5 |
| WXD011 | 44.93 | 10.29 | NA |
| WXD012 | 11.16 | 6.14 | 317.1 |

Note:
NA means no relevant data.

Note: NA means no relevant data.

Conclusion: The compound of the present disclosure exhibits excellent inhibitory activity on Human-SGLT1, Human-SGLT2 and rhDPP4 in vitro.

Example 2: DMPK Study In Vivo

Experimental purpose: Male C57 mice were used as test animals to determine the blood concentration of the compound and evaluate the pharmacokinetic behavior after a single administration.

Experimental operation: 6 healthy adult male C57 mice were selected, 3 for the intravenous injection group and 3 for the oral group. The test compound was mixed with an appropriate amount of solvent[#] of the intravenous injection group, and the mixture was vortexed and sonicated to prepare 1 mg/mL of a clear solution, which was filtered with a microporous membrane for later use. For oral group, the test compound was mixed with the solvent, and the mixture was vortexed and sonicated to prepare 1 mg/mL of a clear solution. After intravenous administration of 1 mg/kg or oral administration of 10 mg/kg to mice, whole blood was collected for a certain period of time, and plasma was prepared. The drug concentration was analyzed by LC-MS/MS method, and the pharmacokineties parameters were calculated by Phoenix WinNonlin software (Pharsight, USA).

The experimental results are shown in Table 5:

TABLE 5

PK test results of the compounds

| Compound | $C_{max}$ (nM) | F % | Oral DNAUC (nM·h/mpk) | $Vd_{ss}$ (L/kg) | Cl (mL/min/kg) | $T_{1/2}$ (h) |
|---|---|---|---|---|---|---|
| WXD001 | 225 | 18.2 | 109 | 17.8 | 42.0 | 8.99 |
| WXD004 | 171 | 10.2 | 113 | 13.2 | 20.7 | 13.4 |

Remarks:
Cmax is the maximum concentration;
F % is the oral bioavailability;
Oral DNAUC = $AUC_{PO}$/Dose, $AUC_{PO}$ is the oral exposure, Dose is the drug dose;
$Vd_{ss}$ is the volume of distribution;
Cl is the clearance rate;
$T_{1/2}$ is the half-life.
"#": The solvent used in WXD001 was 10% N-methylpyrrolidone/10% polyethylene glycol-15 hydroxystearate/80% H2O;

The solvent used in WXD004 was 20% polyethylene glycol 400/10% polyethylene glycol-15 hydroxystearate/70% $H_2O$.

Conclusion: The compound of the present disclosure showed certain oral exposure and bioavailability in mice.

Example 3. Drug Efficacy Study of Rat Oral Glucose Tolerance Test (OGTT) In Vivo Experiment Summary 1. Animal:

| Animal | Category Weeks/weight | SD rat ~8 weeks/250 g | Gender | Male Shanghai Slack Supplier |
|---|---|---|---|---|
| animal feed: | | Common rat and mice feed | | |

2. Experiment Grouping:

| Group | Compound grouping | Dosage | Frequency of administration | Mode of administration | No. of amimal per group |
|---|---|---|---|---|---|
| 1 | Solvent control group | 0 | Single administration | Gavage | 5 |
| 2 | Positive compound (Soagliflozin) | 10 mg/kg | Single administration | Gavage | 5 |
| 3 | Test compound | 10 mg/kg | Single administration | Gavage | 5 |

Experiment Process:
1. Animal Adaptation and Preparation:
The experimental animals needed to be acclimatized in the animal room for 1 week after arriving at the facility.
2. Fasting and Administration
The animals were fasted for 18 h in the metabolic cage, and drugs or solvents (2 mL/kg) were given according to the above table, and then 50% glucose solution (2 g/kg, 4 mL/kg) was administrated immediately.
3. Urine and Blood Sugar Test
Two hours after the animals were given sugar, they resumed eating. The time points of 0 min, 15 min, 30 min, 45 min, 60 min and 120 min were collected for blood glucose determination; urine during 0-24 h was used for urine sugar (mg/200 g) and urine volume test respectively.

4. Data Analysis:
All values will be expressed as average values. Statistical analysis was evaluated using Graphpad Prism 6 one-way analysis of variance Tukey's multiple comparison test. P value of less than 0.05 was considered of statistically significant.
The experimental results are shown in Table 6:

TABLE 6

Experimental results of glucose tolerance in rats

| Compound | Solvent control group | Positive compound (Soagliflozin) | WXD001 |
|---|---|---|---|
| OGTT glucose level $AUC_{0-2\ hr}$ (mol/L × min) | 1079 | 917**** | 670**** |
| Urine sugar level (mg/200 g BW) | 0.4 | 2913**** | 16.2 |
| Urine volume (mL/200 g BW) | 16.8 | 32.2**** | 11.2 |

*means p < 0.5,
**means p < 0.01,
***means p < 0.001,
****means p < 0.0001 vs. solvent control group.
Remarks: 200 g BW is 200 g average weight.
Conclusion: Compared with the solvent control group, the compound of the present disclosure can significantly reduce the blood glucose AUC level of the animal within 2 hours; the 24-hour urine glucose excretion level of the animals is lower than that of the positive compound.

The invention claimed is:
1. A compound of formula (I), an isomer or a pharmaceutically acceptable salt thereof,

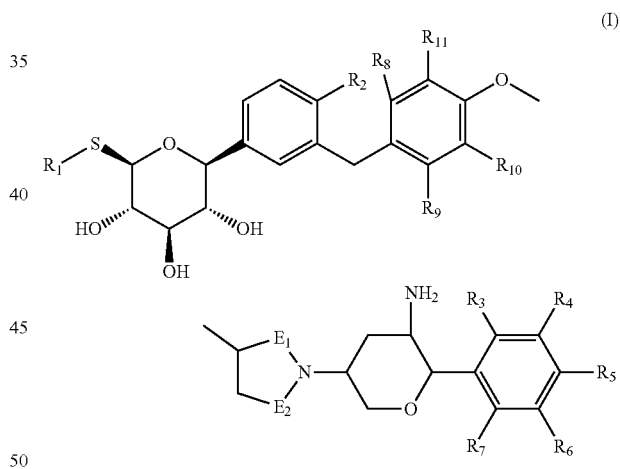

wherein,
R$_1$ is selected from C$_{1-3}$ alkyl, wherein the C$_{1-3}$ alkyl is optionally substituted by 1, 2 or 3 R$_a$;
R$_2$ is selected from Cl, Br, I, OH, NH$_2$ and C$_{1-3}$ alkyl, wherein the C$_{1-3}$ alkyl is optionally substituted by 1, 2 or 3 R$_b$;
R$_3$, R$_4$, R$_5$, R$_6$ and R$_7$ are each independently selected from H, F, Cl, Br, I, OH, NH$_2$ and C$_{1-3}$ alkyl, wherein the C$_{1-3}$ alkyl is optionally substituted by 1, 2 or 3 R$_c$;
R$_8$, R$_9$, R$_{10}$ and R$_{11}$ are each independently selected from H, F, Cl, Br, I, OH, NH$_2$ and C$_{1-3}$ alkyl, wherein the C$_{1-3}$ alkyl is optionally substituted by 1, 2 or 3 R$_d$;
E$_1$ is —(CH$_2$)$_m$—;
E$_2$ is —(CH$_2$)$_n$—;
m is 0, 1 or 2;
n is 0, 1 or 2;

$R_a$, $R_b$, $R_c$ and $R_d$ are each independently selected from F, Cl, Br, I, OH and $NH_2$.

2. The compound, the isomer or the pharmaceutically acceptable salt thereof according to claim 1, wherein $R_1$ is selected from $CH_3$ and Et, and the $CH_3$ and Et are optionally substituted by 1, 2 or 3 $R_a$.

3. The compound, the isomer or the pharmaceutically acceptable salt thereof according to claim 2, wherein $R_1$ is selected from $CH_3$.

4. The compound, the isomer or the pharmaceutically acceptable salt thereof according to claim 1, wherein $R_2$ is selected from Cl, Br, I, OH, $NH_2$, $CH_3$, Et and

wherein the $CH_3$, Et and

are optionally substituted by 1, 2 or 3 $R_b$.

5. The compound, the isomer or the pharmaceutically acceptable salt thereof according to claim 4, wherein $R_2$ is selected from Cl, Br, I, OH, $NH_2$, $CH_3$, Et and

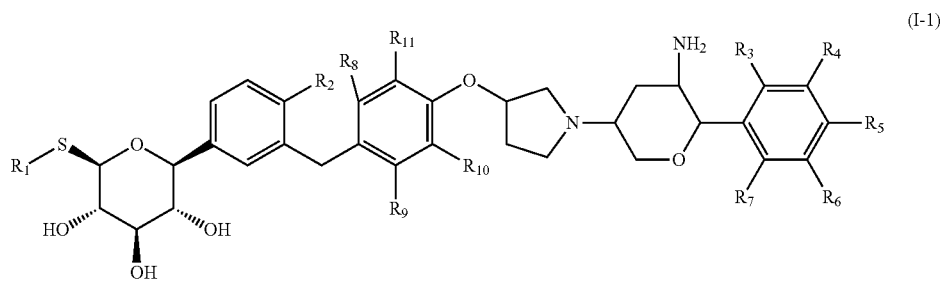

6. The compound, the isomer or the pharmaceutically acceptable salt thereof according to claim 1, wherein $R_3$, $R_4$, $R_5$, $R_6$ and $R_7$ are each independently selected from H, F, Cl, Br, I, OH, $NH_2$, $CH_3$ and Et, wherein the $CH_3$ and Et are optionally substituted by 1, 2 or 3 $R_c$.

7. The compound, the isomer or the pharmaceutically acceptable salt thereof according to claim 6, wherein $R_3$, $R_4$, $R_5$, $R_6$ and $R_7$ are each independently selected from H, F, Cl, Br, I, OH and $NH_2$.

8. The compound, the isomer or the pharmaceutically acceptable salt thereof according to claim 1, wherein $R_8$, $R_9$, $R_{10}$ and $R_{11}$ are each independently selected from H, F, Cl, Br, I, OH, $NH_2$, $CH_3$ and Et, wherein the $CH_3$ and Et are optionally substituted by 1, 2 or 3 $R_d$.

9. The compound, the isomer or the pharmaceutically acceptable salt thereof according to claim 8, wherein $R_8$, $R_9$, $R_{10}$ and $R_{11}$ are each independently selected from H, F, Cl, Br, I, OH, $NH_2$, $CH_3$ and Et.

10. The compound, the isomer or the pharmaceutically acceptable salt thereof according to claim 1, wherein $E_1$ is —$CH_2$— or —$CH_2$—$CH_2$—.

11. The compound, the isomer or the pharmaceutically acceptable salt thereof according to claim 1, wherein $E_2$ is a single bond or —$CH_2$—.

12. The compound, the isomer or the pharmaceutically acceptable salt thereof according to claim 1, wherein the compound is selected from

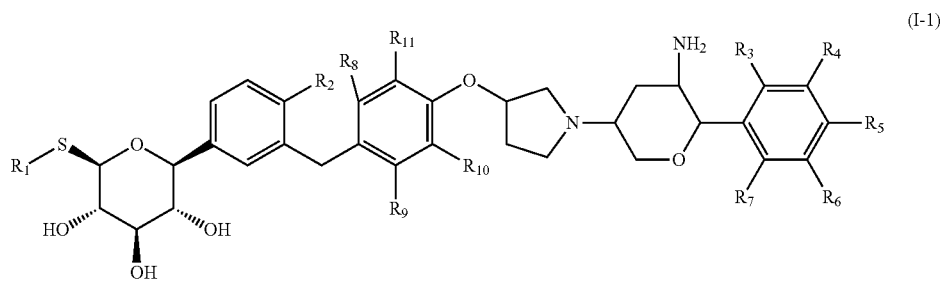

(I-1)

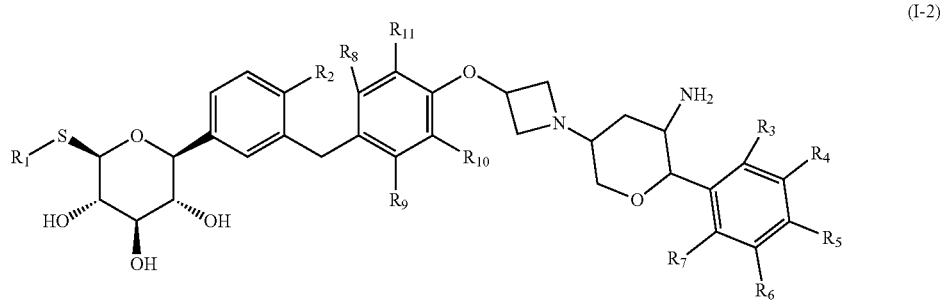

(I-2)

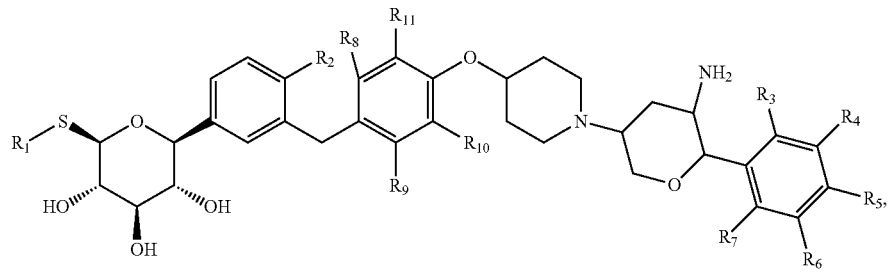

(I-3)

wherein,
$R_1$ is as defined in claim 1;
$R_2$ is as defined in claim 1;
$R_3$, $R_4$, $R_5$, $R_6$ and $R_7$ are as defined in claim 1;
$R_8$, $R_9$, $R_{10}$, and $R_{11}$ are as defined in claim 1.

13. The compound, the isomer or the pharmaceutically acceptable salt thereof according to claim 12, which is selected from

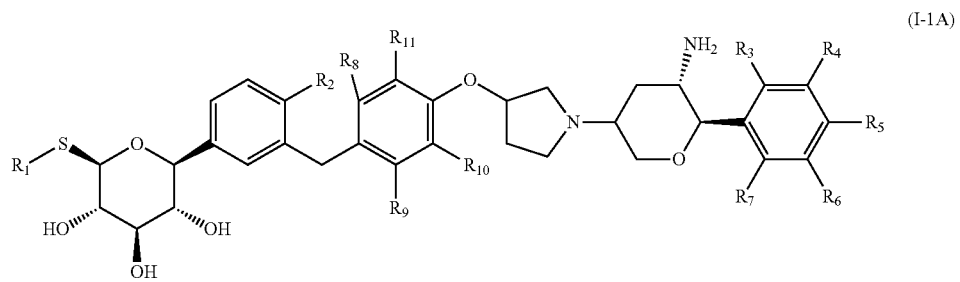

(I-1A)

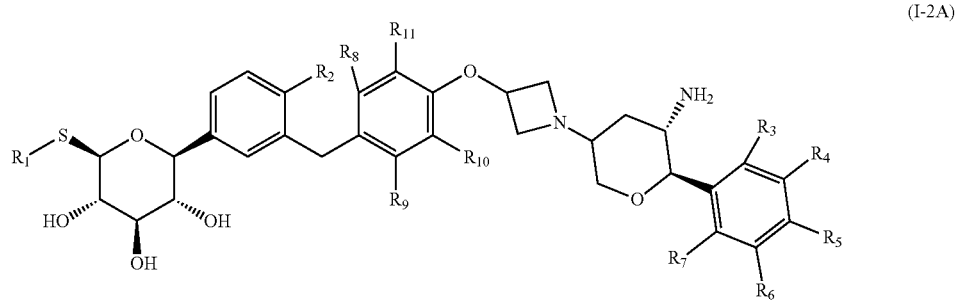

(I-2A)

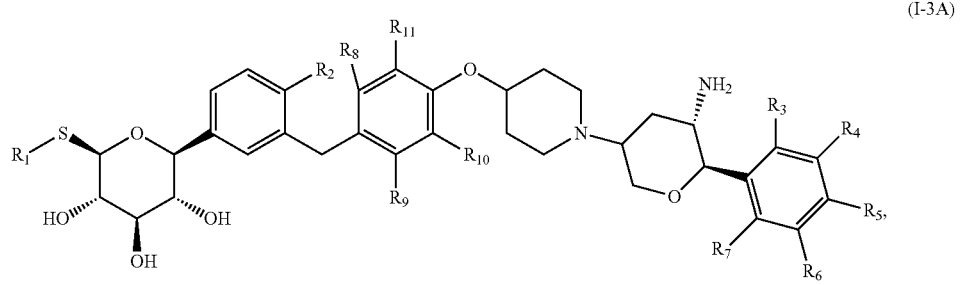

(I-3A)

wherein,
$R_1$ is as defined in claim 12;
$R_2$ is as defined in claim 12;
$R_3$, $R_4$, $R_5$, $R_6$ and $R_7$ are as defined in claim 12;
$R_8$, $R_9$, $R_{10}$, and $R_{11}$ are as defined in claim 12.

14. The following compound, an isomer or a pharmaceutically acceptable salt thereof,
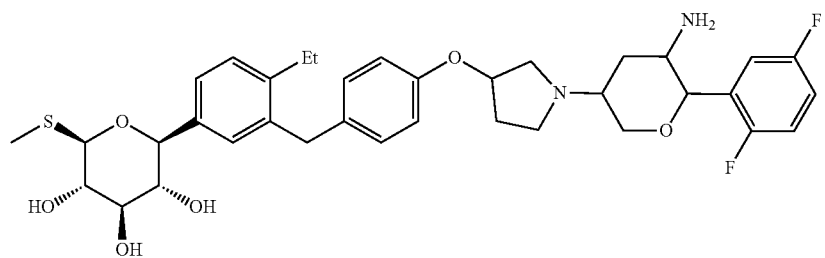
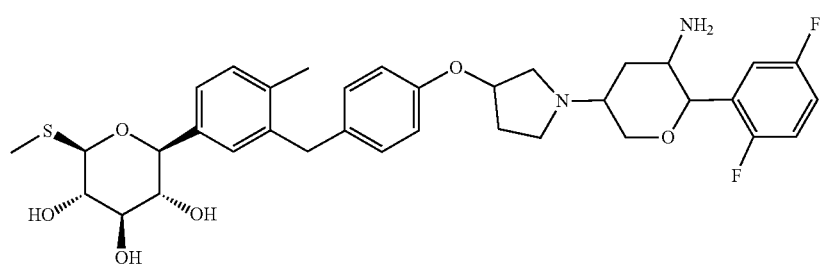
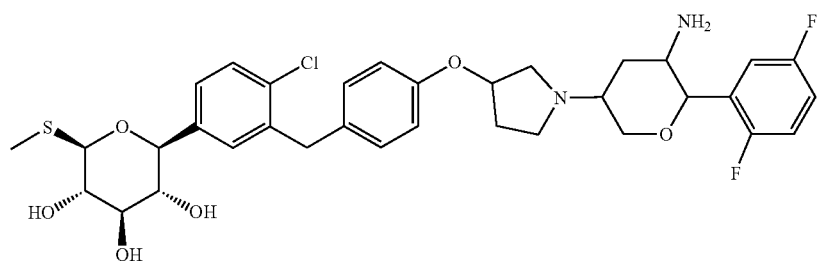
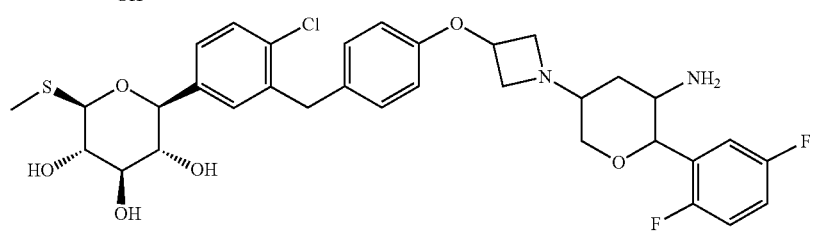
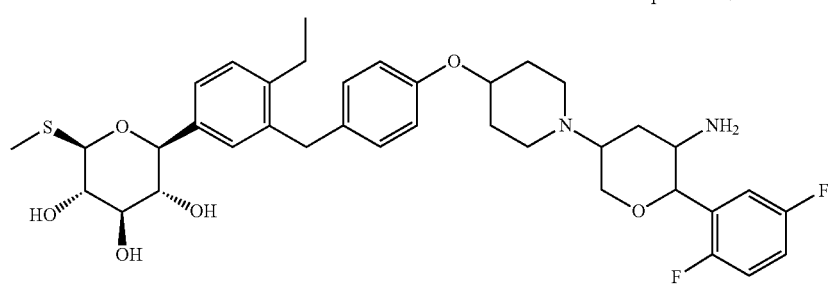
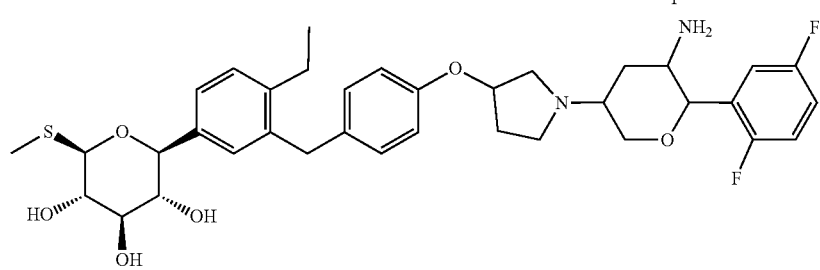

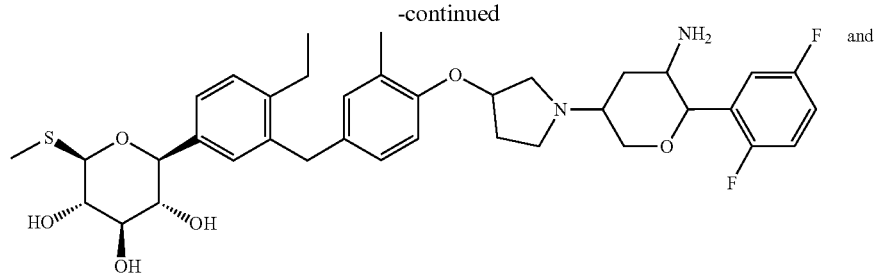
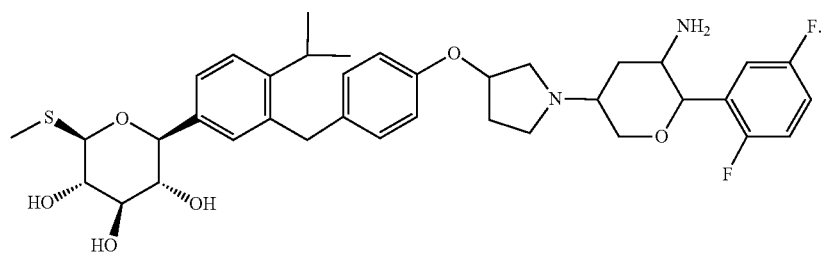
25
15. The compound, the isomer or the pharmaceutically acceptable salt thereof according to claim 14, which is selected from
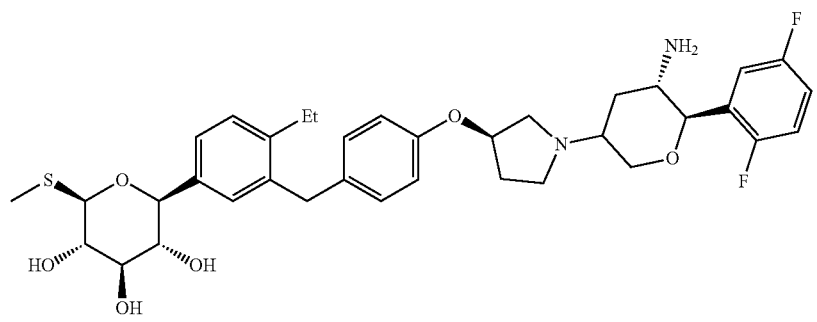
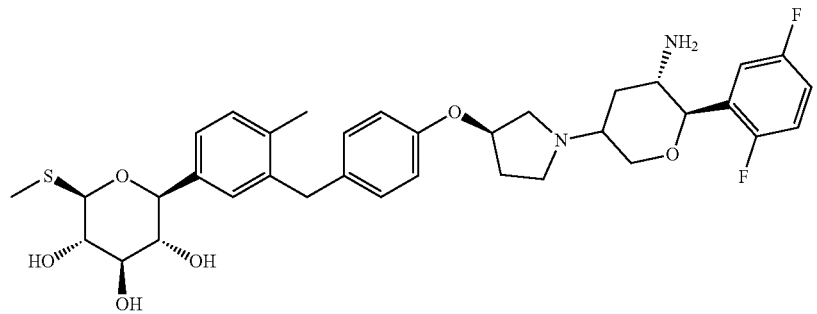
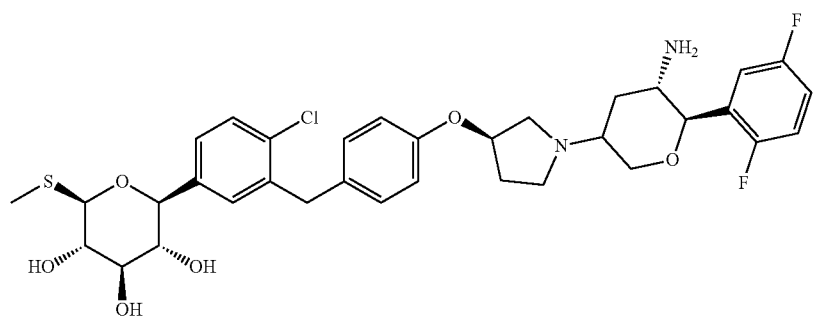

-continued
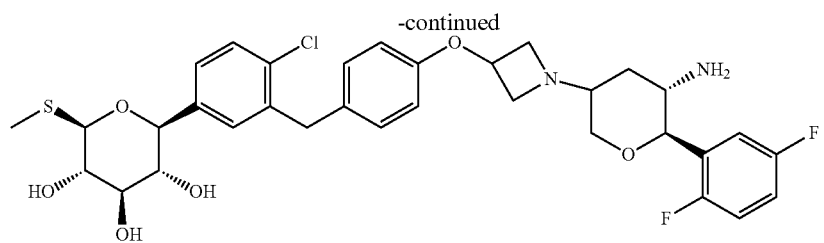
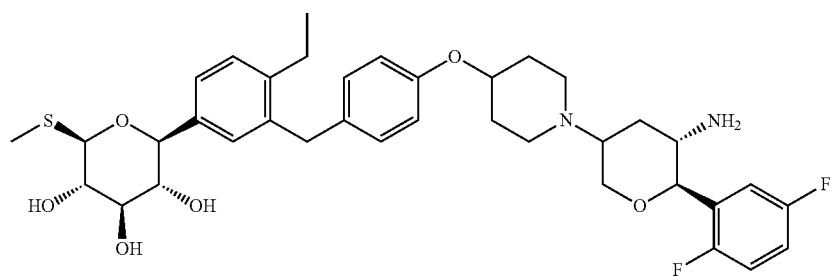
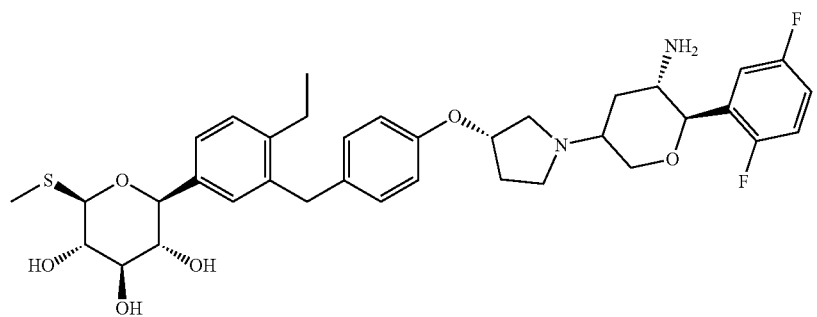
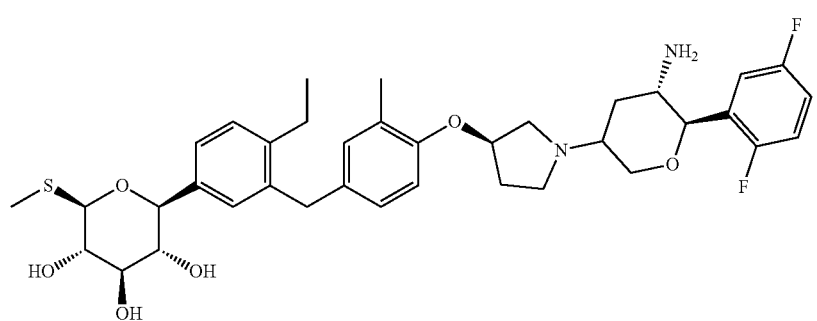
and
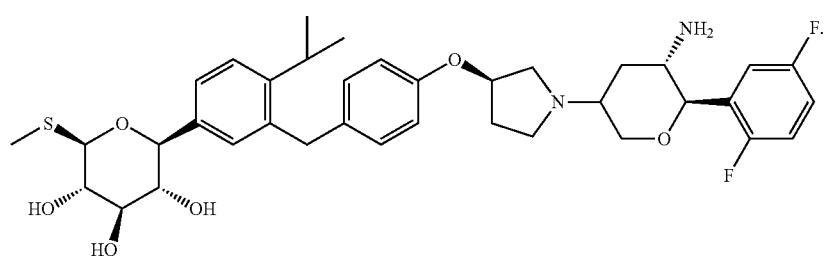

16. The compound, the isomer or the pharmaceutically acceptable salt thereof according to claim 15, which is selected from
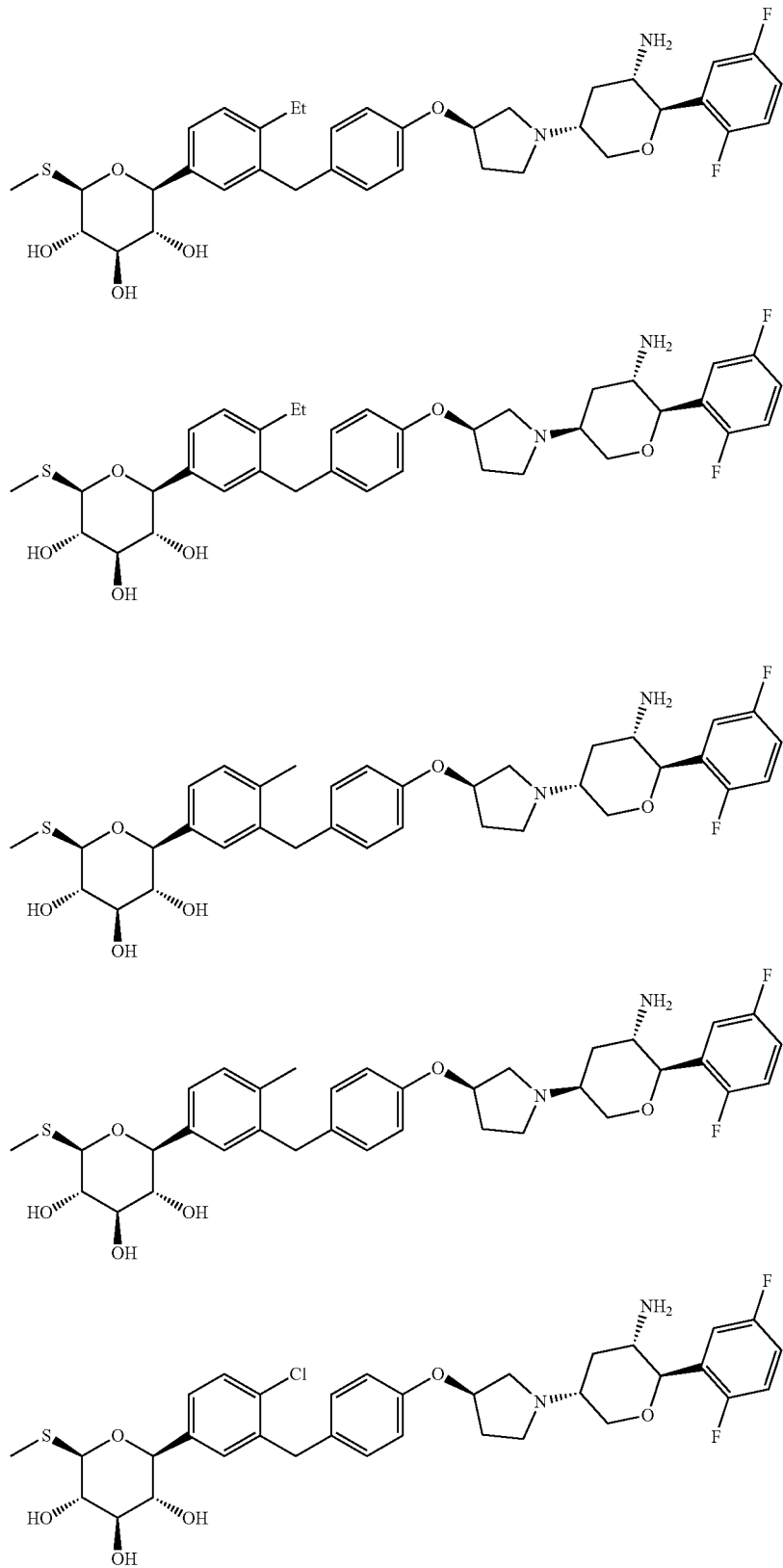

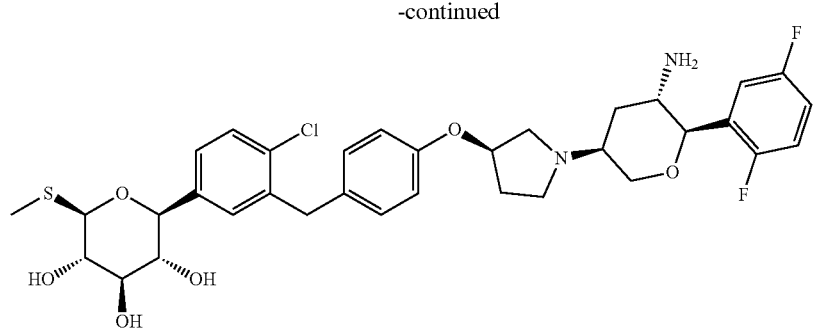
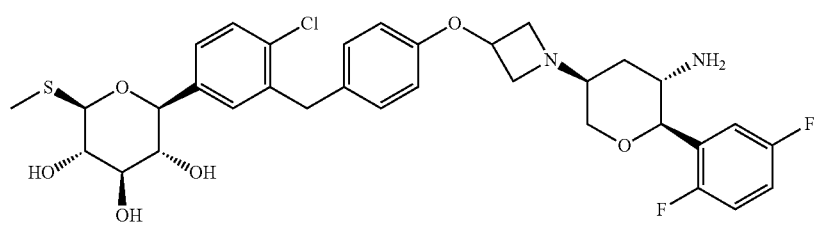
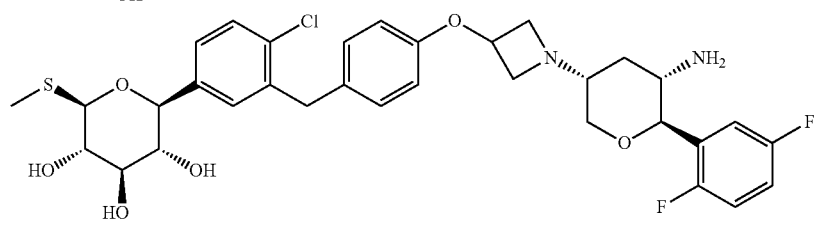
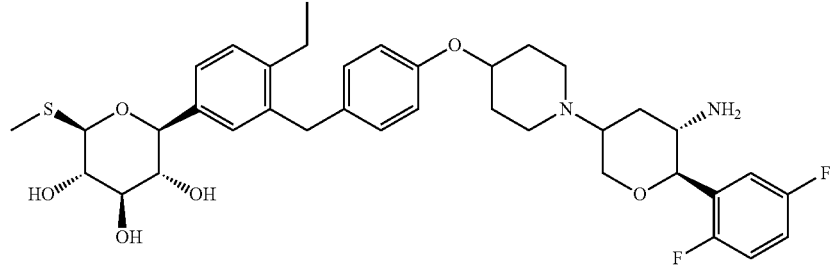
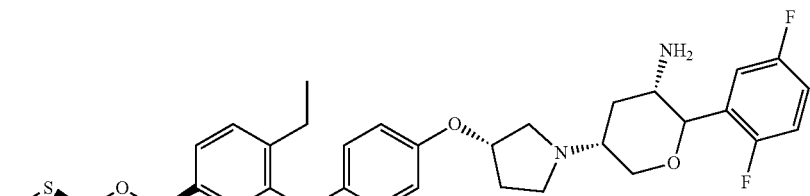
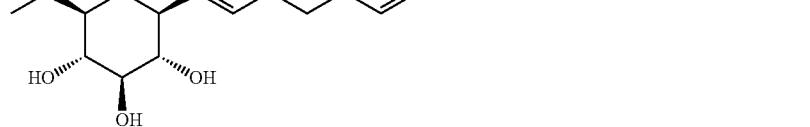
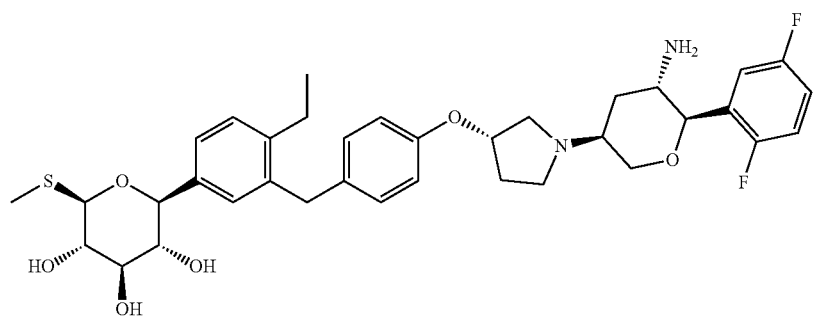

-continued
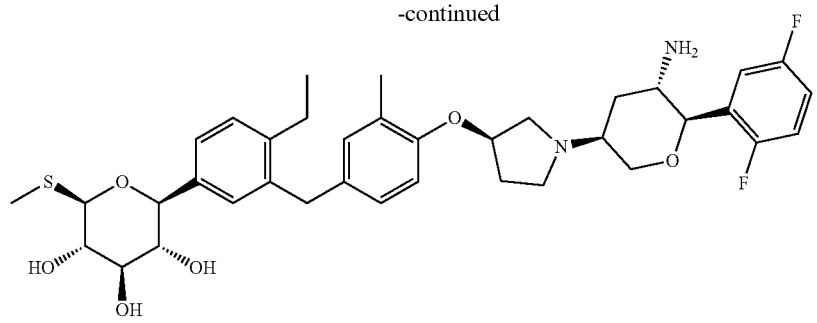
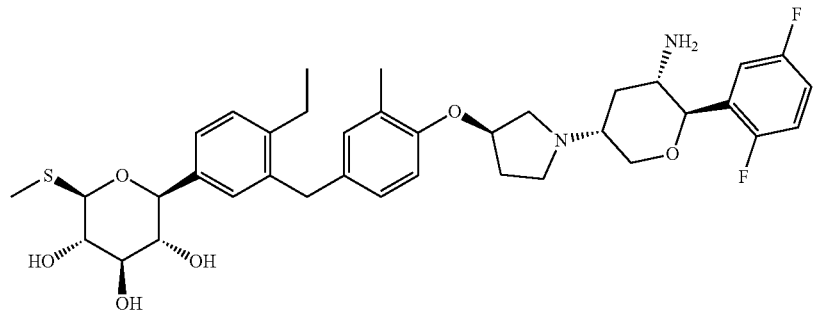
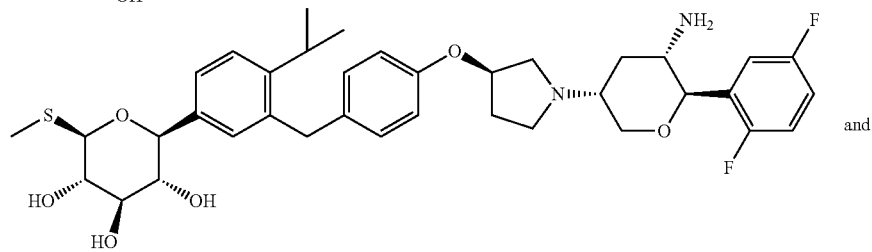
and
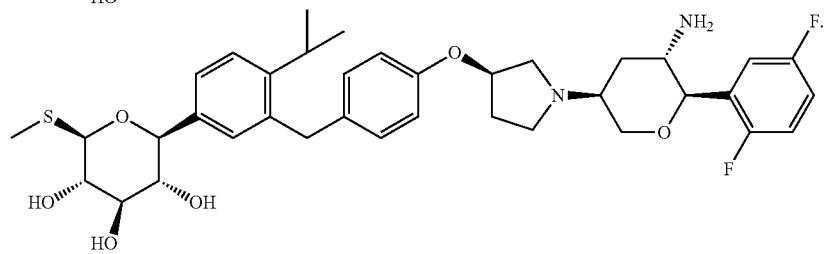
17. A method for triple inhibition of SGLT1/SGLT2/DPP4, comprising administering a therapeutically effective amount of the compound or the pharmaceutically acceptable salt thereof according to claim 1 to a subject in need thereof.
* * * * *